US010689395B2

(12) United States Patent
Vadivelu et al.

(10) Patent No.: US 10,689,395 B2
(45) Date of Patent: Jun. 23, 2020

(54) TRICYCLIC FUSED PYRIDIN-2-ONE DERIVATIVES AND THEIR USE AS BRD4 INHIBITORS

(71) Applicant: JUBILANT BIOSYS LIMITED, Karnataka (IN)

(72) Inventors: Saravanan Vadivelu, Bangalore (IN); Sridharan Rajagopal, Bangalore (IN); Manjunatha M. Ramaiah, Bangalore (IN); Pavan Kumar Gondrala, Bangalore (IN); Murugan Chinnapattu, Bangalore (IN); Dhanalakshmi Sivanandhan, Bangalore (IN); Payal Kiran Parikh, Bangalore (IN); Chandrika Mulakala, Bangalore (IN)

(73) Assignee: JUBILANT BIOSYS LIMITED, Karnataka (IN)

( * ) Notice: Subject to any disclaimer, the term of this patent is extended or adjusted under 35 U.S.C. 154(b) by 0 days.

(21) Appl. No.: 15/754,292

(22) PCT Filed: Sep. 8, 2016

(86) PCT No.: PCT/IN2016/050300
§ 371 (c)(1),
(2) Date: Feb. 21, 2018

(87) PCT Pub. No.: WO2017/042834
PCT Pub. Date: Mar. 16, 2017

(65) Prior Publication Data
US 2018/0237453 A1 Aug. 23, 2018

(30) Foreign Application Priority Data

Sep. 9, 2015 (IN) .......................... 4781/CHE/2015

(51) Int. Cl.
| A61K 31/4353 | (2006.01) |
| A61P 35/00 | (2006.01) |
| C07D 471/04 | (2006.01) |
| C07D 471/14 | (2006.01) |
| C07D 491/044 | (2006.01) |
| C07D 491/14 | (2006.01) |
| C07D 495/14 | (2006.01) |
| C07D 513/14 | (2006.01) |
| C07D 493/14 | (2006.01) |
| A61K 45/06 | (2006.01) |

(52) U.S. Cl.
CPC ............ *C07D 495/14* (2013.01); *A61P 35/00* (2018.01); *C07D 471/14* (2013.01); *C07D 491/14* (2013.01); *C07D 493/14* (2013.01); *C07D 513/14* (2013.01); *A61K 45/06* (2013.01); *A61K 2300/00* (2013.01)

(58) Field of Classification Search
CPC ... A61K 31/4353; A61P 35/00; C07D 471/04; C07D 471/14; C07D 491/044; C07D 491/14; C07D 495/14
See application file for complete search history.

(56) References Cited

U.S. PATENT DOCUMENTS

| 2011/0076291 A1 | 3/2011 | Blaquiere et al. |
| 2015/0148337 A1 | 5/2015 | Albrecht et al. |
| 2018/0282345 A1* | 10/2018 | Vadivelu .............. C07D 471/04 |

FOREIGN PATENT DOCUMENTS

| EA | 201492216 | 3/2015 |
| RU | 2012117394 A | 11/2013 |
| WO | WO 2008/133288 A1 | 11/2008 |
| WO | WO 2012/075383 A2 | 6/2012 |
| WO | WO 2016/157221 A1 | 10/2016 |

OTHER PUBLICATIONS

Manzottie et al., Inhibition of BET Proteins and Histone Deacetylase (HDACs): Crossing Roads in Cancer Therapy; Cancers, vol. 11, No. 3, 304, Mar. 2019.*
Filippakopoulos et al., "Targeting Bromodomains: Epigenetic Readers of Lysine Acetylation," *Nat. Rev. Drug Discovery*, vol. 13, No. 5, pp. 337-356 (2014) [Abstract].
French et al., "BRD4-NUT Fusion Oncogene: A Novel Mechanism in Aggressive Carcinoma," *Cancer Research*, vol. 63, pp. 304-307 (Jan. 2003).
French et al., "BRD-NUT oncoproteins: a family of closely related nuclear proteins that block epithelial differentiation and maintain the growth of carcinoma cells," *Oncogene*, vol. 27, pp. 2237-2242 (2008).
French et al., "Midline Carcinoma of Children and Young Adults with NUT Rearrangement," *Journ. of Clinical Oncology*, vol. 22, pp. 4135-4139 (2004).
Griebenow, et al., "Identification of 4H,6H-[2]benzoxepino[4,5-c][1,2]oxazoles as novel squalene synthase inhibitors," *Bioorg. Med. Chem. Lett.*, vol. 21, pp. 3648-3653 (2011) [Abstract].
Hargreaves, et al., "Control of Inducible Gene Expression by Signal-Dependent Transcriptional Elongation," *Cell*, vol. 138, No. 1, pp. 129-145 (Jul. 2009).
Ichikawa et al., "Discovery of DF-461, a Potent Squalene Synthase Inhibitor," *ACS Medicinal Chemistry Letters*, vol. 4, pp. 932-936 (2013).

(Continued)

Primary Examiner — Brenda L Coleman
(74) Attorney, Agent, or Firm — Foley & Lardner LLP

(57) ABSTRACT

The present disclosure describes heterocyclic compounds of Formula I or, its stereoisomers, pharmaceutically acceptable salts, complexes, hydrates, solvates, tautomers, polymorphs, racemic mixtures, optically active forms and pharmaceutically active derivatives thereof and pharmaceutical compositions containing them as the active ingredient. The present disclosure also describes the synthesis and characterization of aforementioned compounds to exhibit high anticancer activity. The compounds of the present disclosure are useful as medicaments and their use in the manufacture of medicaments for treatment, prevention, or suppression of diseases, and conditions mediated by one or more BET family of bromodomains.

10 Claims, No Drawings

(56) References Cited

OTHER PUBLICATIONS

LeRoy et al., "The double bromodomain proteins Brd2 and Brd3 couple histone acetylation to transcription," *Mol. Cell.*, vol. 30, No. 1, pp. 51-60 (Apr. 2008).
International Search Report and Written Opinion issued in related International Patent Application No. PCT/IN2016/050300, completed Dec. 9, 2016.
Foreign Action issued in co-pending Russian Patent Application No. 2018112015, dated Jul. 31, 2019.

* cited by examiner

TRICYCLIC FUSED PYRIDIN-2-ONE DERIVATIVES AND THEIR USE AS BRD4 INHIBITORS

CROSS-REFERENCE TO RELATED APPLICATIONS

This application is the National Stage of International Patent Application No. PCT/IN2016/050300, filed Sep. 8, 2016, which claims priority from India Patent Application No. 4781/CHE/2015, filed Sep. 9, 2015. The contents of these applications are incorporated herein by reference in their entirety.

The present disclosure relates to the field of medicinal chemistry and more particularly to the development of compounds as inhibitors of one or more BET family of bromodomains. The present disclosure relates to heterocyclic compounds of the Formula (I) or its pharmaceutically acceptable salts thereof and pharmaceutical compositions containing them as the active ingredient.

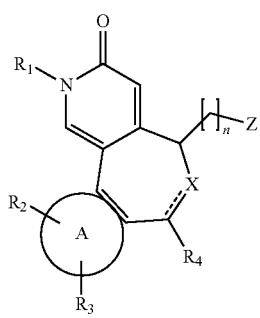

(I)

The present disclosure further relates to the synthesis and characterization of aforementioned compounds and a study of their anticancer activity. The compounds of the present disclosure are useful as medicaments and their use in the manufacture of medicaments for treatment, prevention or suppression of diseases, and conditions mediated by one or more BET family of bromodomains.

BACKGROUND

Transcriptional regulation is a major event in cell differentiation, proliferation and apoptosis. Transcriptional activation of a set of genes determines cellular function and is tightly regulated by a variety of factors. One of the regulatory mechanisms involved in this process is an alteration in the tertiary structure of DNA, which affects transcription factors to their target DNA regiments. Nucleosomal integrity is regulated by the acetylation status of the core histone, with the result being permissiveness to transcription. The regulations of transcription factor are thought to involve changes in the structure of chromatin. Changing the affinity of histone proteins for coiled DNA in the nucleosome alters the structure of chromatin. Hypoacetylated histones are believed to have greater affinity to the DNA and form a tightly bound DNA-histone complex and render the DNA inaccessible to transcriptional regulation. The acetylation status of the histone is governed by the balanced activities of the histone acetyl transferase (HAT) and histone deacetylase (HDAC). The bromodomain and extraterminal family of proteins called BET proteins are readers of the acetyl status of histone and change the chromatin structure and gene expression.

The BET family of bromodomain containing proteins comprises four proteins, namely BRD2, BRD3, BRD4 and BRDT, which are widely expressed in various tissues, except BRDT which is localized in the testes. Each of the BRD proteins contains tandem bromodomains capable of binding to acetylated lysine residues in histones H3 and H4. It has been reported that BRD2 and BRD3 are associated with histones along actively transcribed genes and involved in facilitating transcriptional elongation (Leroy et al, Mol. Cell. 2008 30(1):51-60), while BRD4 appears to be involved in the recruitment of the pTEF-[beta] complex to nucleosomes, which results in phosphorylation of RNA polymerase II and increases the transcriptional elongation of neighboring genes. (Hargreaves et al, Cell, 2009 138(1): 129-145).

BRD4 or BRD3 may fuse with NUT (nuclear protein in testes) forming novel fusion oncogenes, BRD4-NUT or BRD3-NUT, in a highly malignant form of epithelial neoplasia (French et al. Cancer Research, 2003, 63, 304-307 and French et al. Journal of Clinical Oncology, 2004, 22 (20), 4135-4139). Data suggests that BRD-NUT fusion proteins contribute to carcinogenesis (Oncogene, 2008, 27, 2237-2242). A BET protein which includes BRD4 has been shown to be an important regulator of gene expression profiles in numerous diseases such as cancer, diabetes, obesity, cardiovascular, and renal disorders. Currently several BRD4 inhibitors are in various stages of clinical trials for cancer, such as IBET-762, JQ1, OTX-015 and RVX-2135 (P. Filippakopoulos, et. al., Nature Review Drug Discovery, 13, 2014, 337-356, M. Brand, et. al., ACS Chem. Biol, 10, 2015, 22-39).

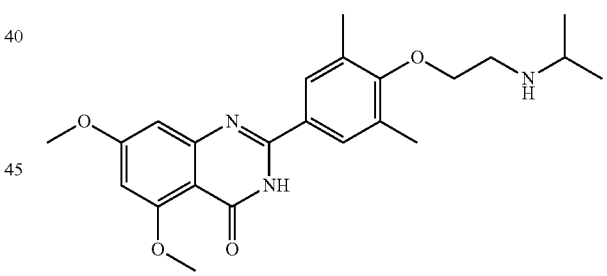

RVX-2135, Phase 1

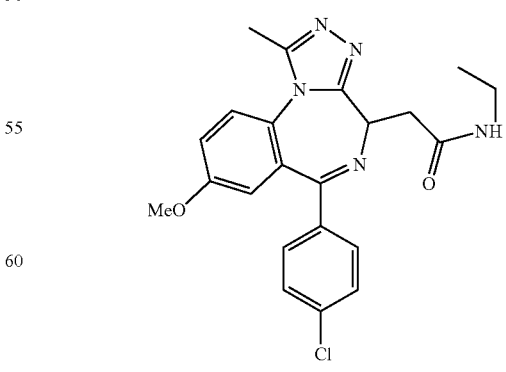

iBET-762-Phase 1

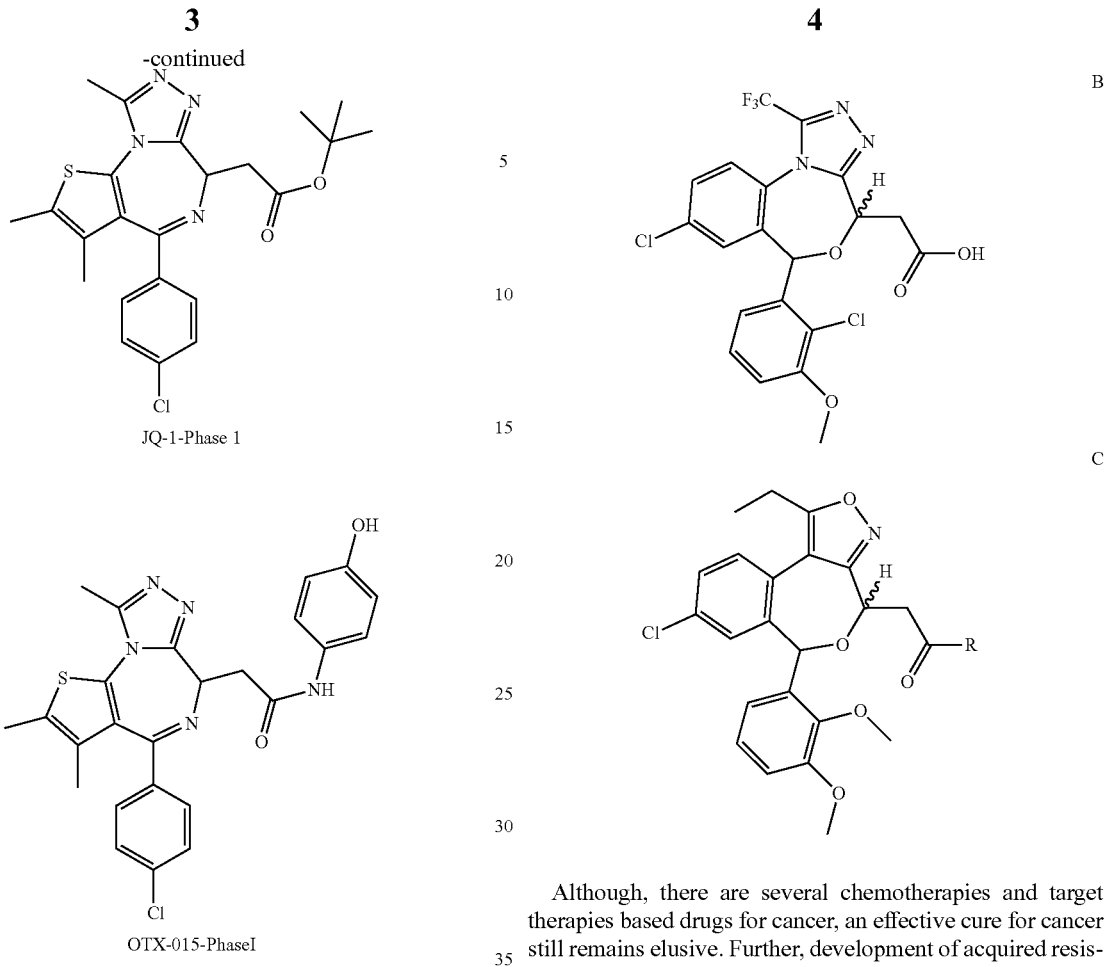

Although, there are several chemotherapies and target therapies based drugs for cancer, an effective cure for cancer still remains elusive. Further, development of acquired resistance and disease relapse are major issues that still need to be addressed. Even though several bromodomain inhibitors are known in the clinic as well as in the preclinic, there still remains a need for finding potent bromodomain inhibitors having desirable drug like properties.

Therefore, the present invention provides novel and drug like molecules having good potency as BRD4 inhibitors which can inhibit the binding of acetylated lysine residue of histone for controlling gene expressions in various diseases.

A tricyclic aryl compound as squalene synthase inhibitor has been disclosed in WO2008133288 for the treatment of hypercholesterolemia, hypertriglyceridemia and hypo-HDL cholesterolemia and/or arteriosclerosis.

SUMMARY

The present disclosure is based on the development of compounds of Formula I (see below) exhibiting advantageous anti-cancer properties. Thus, the present disclosure provides a compound of Formula I

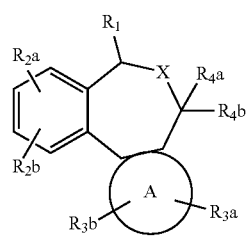

Masanori Ichikawa et. al published a paper (*ACS Med. Chem. Lett.*, 2013, 932-936) describing the squalene synthase inhibitor DF4611 (B). Nils Griebenow, et. al. have also reported a (*Bioorg. Med. Chem. Lett.* 21, 2011, 3648-3653) synthesis of novel 4H,6H-[2]benzoxepino[4,5-c][1,2]oxazoles (C) as squalene synthase inhibitors.

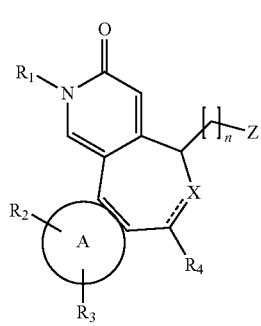

Formula I or its pharmaceutically acceptable salts thereof; wherein; ---- is absent or a single bond; X is selected from —O—, —N—, or —S—; n is 0-6; $R_1$ is selected from the group consisting of hydrogen, halogen, $C_{1-6}$ alkyl, $C_{1-6}$ alkoxy, $C_{1-6}$ haloalkyl, $C_{3-8}$ cycloalkyl, $C_{5-6}$ aryl, $C_{1-6}$ heteroaryl, $C_{1-6}$ alkoxyalkyl with heteroatoms selected from N, O, S; wherein $C_{1-6}$ alkyl, $C_{3-8}$ cycloalkyl, $C_{5-6}$ aryl, $C_{1-6}$ heteroaryl, is optionally substituted with one or more of the groups selected from hydrogen, $C_{1-6}$ alkyl, halogen, OH; $R_2$ and $R_3$ are independently selected from hydrogen, halogen, hydroxy, nitro, cyano, azido, nitroso, oxo (=O), thioxo (=S), —SO$_2$—, amino, hydrazino, formyl, $C_{1-6}$ alkyl, haloalkyl, $C_{1-6}$ alkoxy, $C_{1-6}$ haloalkoxy; arylalkoxy; $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —COOR$_a$, —C(O)R$_b$, —C(S) R$_a$, —C(O)NR$_a$R$_b$, —C(S)NR$_a$R$_b$, —NR$^a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O) OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ or —SO$_2$R$_a$, wherein R$_a$, R$_b$ and R$_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{2-6}$ heteroarylalkyl; $R_4$ is selected from the group consisting of hydrogen, $C_{1-6}$ alkyl, $C_{1-6}$ haloalkyl, $C_{3-8}$ cycloalkyl, $C_{5-6}$ aryl, $C_{1-6}$ heteroaryl, $C_{1-6}$ alkoxyalkyl with heteroatoms selected from N, O, S; wherein $C_{1-6}$ alkyl, $C_{3-8}$ cycloalkyl, $C_{5-6}$ aryl, $C_{2-6}$ heteroaryl, is optionally substituted with one or more of the groups selected from hydrogen, $C_{1-6}$ alkyl, $C_{3-8}$ cycloalkyl, halogen, OH and cyano; ring A is selected from the group consisting of $C_{1-6}$ heteroaryl, $C_{3-8}$ cycloalkyl, $C_{3-10}$ cycloaryl, $C_{4-6}$ heterocycloalkyl, and $C_{4-10}$ heterocycloaryl with heteroatoms selected from N, O, S; Z is selected from —CH$_2$OR$_5$, —COOR$_5$ or —CONR$_5$R$_6$, —NR$_5$R$_6$, —NR$_5$CO—OR$_6$, —NR$_5$CO—NR$_6$R$_7$, —NR$_5$COR$_6$, —NSO$_2$R$_6$ or —O—CO—NR$_5$R$_6$; $R_5$, $R_6$ and $R_7$ are independently selected from hydrogen or substituted or unsubstituted $C_{5-6}$ aryl, $C_{1-6}$ heteroaryl, $C_{3-8}$ cycloalkyl and $C_{1-6}$ alkyl; wherein when, $R_5$, $R_6$ and $R_7$ are substituted, the one or more substituents are selected from hydrogen, halogen, hydroxy, nitro, cyano, azido, nitroso, oxo (=O), thioxo (=S), —SO$_2$—, amino, hydrazino, formyl, $C_{1-6}$ alkyl, haloalkyl, $C_{1-6}$ alkoxy, $C_{1-6}$ haloalkoxy; $C_{5-6}$ arylalkoxy, $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —COOR$_a$, —C(O)R$_b$, —(S)R$_a$, —C(O)NR$_a$R$_b$, —C(S)NR$_a$R$_b$, —NR$^a$C(O) NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S) R$_b$—, —SONR$_a$R$_b$—, —SO$_2$NR$_a$R$_b$—, —OR$_a$, —R$_a$C(O) OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ or —SO$_2$R$_a$, wherein R$_a$, R$_b$ and R$_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl.

The present disclosure relates to a composition comprising a compound of Formula (I) or its pharmaceutically acceptable salts, together with a carrier.

The present disclosure relates to a pharmaceutical composition comprising a compound of Formula I or its pharmaceutically acceptable salts, together with a pharmaceutically acceptable carrier, optionally in combination with one or more other pharmaceutical compositions.

The present disclosure further relates to a method of preventing or treating proliferative diseases by administering a therapeutically effective amount of novel compound of the Formula (I) or a pharmaceutically acceptable salt and/or prodrug.

The present disclosure relates to a process of preparation of compound of Formula (I) or its pharmaceutically acceptable salts.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art.

The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

In the structural formulae given herein and throughout the present disclosure, the following terms have been indicated meaning, unless specifically stated otherwise.

The term "alkyl" refers to straight or branched aliphatic hydrocarbon chain having the 1-6 carbon atoms. This term is exemplified by groups such as n-butyl, iso-butyl, t-butyl, n-hexyl and the like. The groups may be optionally substituted.

The term "aryl" refers to aromatic radicals having 5 to 10 carbon atoms having a single ring (e.g. phenyl) or multiple rings (e.g. biphenyl), or multiple condensed (fused) rings (e.g. naphthyl or anthranyl), which may be optionally substituted by one or more substituents.

Preferred aryl groups, without limitation, include phenyl, naphthyl, indanyl, biphenyl and the like.

The term "arylalkyl" refers to an aryl group directly bonded to an alkyl group, which may be optionally substituted by one or more substituents. Preferred arylalkyl groups, without limitation, include —CH$_2$C$_6$H$_5$, —C$_2$H$_4$C$_6$H$_5$ and the like.

The term "heterocyclyl" refers to a heterocyclic ring radical which may be optionally substituted by one or more substituents. The heterocyclyl ring radical may be attached to the main structure at any heteroatom or carbon atom that results in the creation of a stable structure.

Furthermore the term "heterocyclyl" refers to a stable 2 to 6 membered rings radical, which consists of carbon atoms and from one to five heteroatom's selected from nitrogen, phosphorus, oxygen and sulfur. For purposes of this invention the heterocyclic ring radical may be monocyclic, bicyclic or tricyclic ring systems, and the nitrogen, phosphorus, carbon, oxygen, or sulfur atoms in the heterocyclic ring radical may be optionally oxidized to various oxidation states. In addition, the nitrogen atom may be optionally quaternized; and the ring radical may be partially or fully saturated. Preferred heterocyclyl groups, without limitation, include azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyrazolyl, pyridyl, pteridinyl, purinyl, quinazolinyl, qunioxalinyl, quinolinyl, isoquinolinyl, tetrazolyl, imidazolyl, tetrahydroisoquinolinyl, piperidinyl, piperazinyl, homopiperazinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, triazolyl, indanyl, isoxazolyl, isoxazolidinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, thienyl, morpholinyl, thiomorpholinyl, thiamorpholinyl sulfoxide, furyl, tetrahydrofuryl, tetrahydropyranyl, chromanyl and isochromanyl.

The term "heteroaryl" refers to a heteroaromatic carbocyclic group of 1 to 6 carbon atoms having a single ring (e.g. pyridine) or multiple rings (e.g. isoquinoline), or multiple condensed (fused) rings. Preferred heteroaryls include thiophene, pyrazole, thiazole, pyridine and the like. The groups may be optionally substituted.

The term "heteroarylalkyl" refers to a heteroaryl group directly bonded to an alkyl group, which may be optionally substituted by one or more substituents. Preferred heteroarylalkyl groups, without limitation, include-CH$_2$-pyridinyl, —C$_2$H4-furyl and the like.

The term "cycloalkyl" refers to non-aromatic mono or polycyclic ring system of about 3 to 12 carbon atoms, which may be optionally substituted by one or more substituent's. The polycyclic ring denotes hydrocarbon systems containing two or more ring systems with one or more ring carbon atoms in common, i.e., a spiro, fused or bridged structures. Preferred cycloalkyl groups include, without limitation, cyclopropyl, cyclobutyl, cyclopentyl, cyclohexyl, cyclooctanyl, perhydronaphthyl, adamantyl, noradamantyl and norbornyl groups, bridged cyclic groups or spirobicyclic groups e.g. spiro [4.4] non-2-yl and the like.

The term "alkoxy" refers to an alkyl group attached via an oxygen linkage to the rest of the molecule, which may be optionally substituted by one or more substituents. Preferred alkoxy groups, without limitation, include —OCH$_3$, —OC$_2$H$_5$ and the like.

The term "alkylthio" refers to an alkyl group attached via a sulfur linkage to the rest of the molecule, which may be optionally substituted by one or more substituents. Preferred alkylthio groups, without limitation, include —SCH$_3$, —SC$_2$H$_5$ and the like.

The term "alkylamino" refers to an alkyl group as defined above attached via amino linkage to the rest of the molecule, which may be optionally substituted by one or more substituent's. Preferred alkylamino groups, without limitation include —NHCH$_3$, —N(CH$_3$)$_2$, and the like.

"Halo" or "Halogen", alone or in combination with any other term means halogens such as chloro (Cl), fluoro (F), bromo (Br) and iodo (I).

Furthermore, the compound of Formula (I) can be its derivatives, analogs, tautomeric forms, stereoisomers, diastereomers, geometrical isomers, polymorphs, solvates, intermediates, metabolites, prodrugs or pharmaceutically acceptable salts and compositions.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds. It is also understood that some isomeric form such as diastereomers, enantiomers and geometrical isomers can be separated by physical and/or chemical methods by those skilled in the art. Pharmaceutically acceptable solvates may be hydrates or comprising of other solvents of crystallization such as alcohols, ether, and the like.

The term "solvate", as used herein, refers to a crystal form of a substance which contains solvent.

The term "hydrate" refers to a solvate wherein the solvent is water.

The phrase "pharmaceutically acceptable" refers to compounds or compositions that are physiologically tolerable and do not typically produce allergic or similar untoward reaction, including but not limited to gastric upset or dizziness when administered to mammals.

Pharmaceutically acceptable salts forming part of this invention include salts derived from inorganic bases such as like Li, Na, K, Ca, Mg, Fe, Cu, Zn and Mn; salts of organic bases such as N, N'-diacetylethylenediamine, glucamine, triethylamine, choline, dicyclohexylamine, benzylamine, trialkylamine, thiamine, guanidine, diethanolamine, α-phenylethylamine, piperidine, morpholine, pyridine, hydroxyethylpyrrolidine, hydroxyethylpiperidine, and the like. Salts also include amino acid salts such as glycine, alanine, cystine, cysteine, lysine, arginine, phenylalanine, guanidine etc. Salts may include acid addition salts where appropriate which are sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates, ketoglutarates and the like.

As used herein, the term "substituted" is contemplated to include all permissible substituents of organic compounds.

In a broad aspect, the permissible substituents include acyclic and cyclic, branched and unbranched, carbocyclic and heterocyclic, aromatic and nonaromatic substituents of organic compounds. Illustrative substituents, for example, include those described herein above. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

The term "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, the route of administration, and like factors within the knowledge and expertise of the attending physician.

The compounds described herein can also be prepared in any solid or liquid physical form, for example the compound can be in a crystalline form, in amorphous form and have any particle size. Furthermore, the compound particles may be micronized or nanoized, or may be agglomerated, particulate granules, powders, oils, oily suspensions or any other form of solid or liquid physical forms.

The compounds described herein may also exhibit polymorphism. This invention further includes different polymorphs of the compounds of the present invention.

The term "polymorphs" refers to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice.

The term "prodrugs" refers to the precursor of the compound of Formula (I), which on administration undergoes chemical conversion by metabolic processes before becoming active pharmacological substances. In general, such prodrugs will be functional derivatives of a compound of the invention, which are readily convertible in vivo into a compound of the invention.

The present disclosure relates to a compound of Formula I

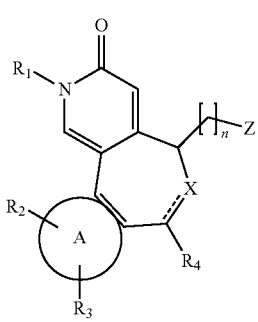

Formula I or its stereoisomers, pharmaceutically acceptable salts, complexes, hydrates, solvates, tautomers, polymorphs, racemic mixtures, optically active forms and pharmaceutically active derivative thereof,
wherein;
---- is absent or a single bond; X is selected from —O—, —N—, or —S—; n is 0-6; $R_1$ is selected from the group consisting of hydrogen, halogen, $C_{1-6}$ alkyl, $C_{1-6}$ alkoxy, $C_{1-6}$ haloalkyl, $C_{3-8}$ cycloalkyl, $C_{5-6}$ aryl, $C_{1-6}$ heteroaryl, $C_{1-6}$ alkoxyalkyl with heteroatoms selected from N, O, S; wherein $C_{1-6}$ alkyl, $C_{3-8}$ cycloalkyl, $C_{5-6}$ aryl, $C_{1-6}$ heteroaryl, is optionally substituted with one or more of the groups selected from hydrogen, $C_{1-6}$ alkyl, halogen, OH; $R_2$ and $R_3$ are independently selected from hydrogen, halogen, hydroxy, nitro, cyano, azido, nitroso, oxo (=O), thioxo (=S), —SO$_2$-amino, hydrazino, formyl, $C_{1-6}$ alkyl, haloalkyl, $C_{1-6}$ alkoxy, $C_{1-6}$ haloalkoxy; arylalkoxy; $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$^a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ or —SO$_2$R$_a$, wherein R$_a$, R$_b$ and R$_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{2-6}$ heteroarylalkyl; $R_4$ is selected from the group consisting of hydrogen, $C_{1-6}$ alkyl, $C_{1-6}$ haloalkyl, $C_{3-8}$ cycloalkyl, $C_{5-6}$ aryl, $C_{1-6}$ heteroaryl, $C_{1-6}$ alkoxyalkyl with heteroatoms selected from N, O, S; wherein $C_{1-6}$ alkyl, $C_{3-8}$ cycloalkyl, $C_{5-6}$ aryl, $C_{2-6}$ heteroaryl, is optionally substituted with one or more of the groups selected from hydrogen, $C_{1-6}$ alkyl, $C_{3-8}$ cycloalkyl, halogen, OH and cyano; ring A is selected from the group consisting of $C_{1-6}$ heteroaryl, $C_{3-8}$ cycloalkyl, $C_{3-10}$ cycloaryl, $C_{4-6}$ heterocycloalkyl, and $C_{4-10}$ heterocycloaryl with heteroatoms selected from N, O, S; Z is selected from —CH$_2$OR$_5$, —COOR$_5$ or —CONR$_5$R$_6$, —NR$_5$R$_6$, —NR$_5$CO—OR$_6$, —NR$_5$CO—NR$_6$R$_7$, —NR$_5$COR$_6$, —NSO$_2$R$_6$ or —O—CO—NR$_5$R$_6$; $R_5$, $R_6$ and $R_7$ are independently selected from hydrogen or substituted or unsubstituted $C_{5-6}$ aryl, $C_{1-6}$ heteroaryl, $C_{3-8}$ cycloalkyl and $C_{1-6}$ alkyl; wherein when, $R_5$, $R_6$ and $R_7$ are substituted, the one or more substituents are selected from hydrogen, halogen, hydroxy, nitro, cyano, azido, nitroso, oxo (=O), thioxo (=S), —SO$_2$—, amino, hydrazino, formyl, $C_{1-6}$ alkyl, haloalkyl, $C_{1-6}$ alkoxy, $C_{1-6}$ haloalkoxy; $C_{5-6}$ arylalkoxy, $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$^a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$OR$_b$—, —SR$_a$, —SOR$_a$ or —SO$_2$R$_a$, wherein R$_a$, R$_b$ and R$_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl.

According to an embodiment, the present disclosure relates to a compound of the Formula (I) or its stereoisomers, pharmaceutically acceptable salts, complexes, hydrates, solvates, tautomers, polymorphs, racemic mixtures, optically active forms and pharmaceutically active derivative thereof, wherein ---- is absent or a single bond; X is selected from —O—, or —N—; n is 0-6; $R_1$ is selected from the group consisting of hydrogen, halogen, $C_{1-6}$ alkyl, $C_{1-6}$ alkoxy, $C_{1-6}$ haloalkyl, $C_{3-8}$ cycloalkyl, $C_{5-6}$ aryl, $C_{1-6}$ heteroaryl, $C_{1-6}$ alkoxyalkyl with heteroatoms selected from N, O, S; wherein $C_{1-6}$ alkyl, $C_{3-8}$ cycloalkyl, $C_{5-6}$ aryl, $C_{1-6}$ heteroaryl, is optionally substituted with one or more of the groups selected from hydrogen, $C_{1-6}$ alkyl, halogen, OH; $R_2$ and $R_3$ are independently selected from hydrogen, halogen, hydroxy, nitro, cyano, azido, nitroso, oxo (=O), thioxo (=S), —$SO_2$—, amino, hydrazino, formyl, $C_{1-6}$ alkyl, haloalkyl, $C_{1-6}$ alkoxy, $C_{1-6}$ haloalkoxy; arylalkoxy; $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR^aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, $NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ or —$SO_2R_a$, wherein $R_a$, $R_b$ and $R_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{2-6}$ heteroarylalkyl; $R_4$ is selected from the group consisting of hydrogen, $C_{1-6}$ alkyl, $C_{1-6}$ haloalkyl, $C_{3-8}$ cycloalkyl, $C_{5-6}$ aryl, $C_{1-6}$ heteroaryl, $C_{1-6}$ alkoxyalkyl with heteroatoms selected from N, O, S; wherein $C_{1-6}$ alkyl, $C_{3-8}$ cycloalkyl, $C_{5-6}$ aryl, $C_{2-6}$ heterocyclyl, is optionally substituted with one or more of the groups selected from hydrogen, $C_{1-6}$ alkyl, $C_{3-8}$ cycloalkyl, halogen, OH and cyano; ring A is selected from the group consisting of $C_{1-6}$ heteroaryl, $C_{3-8}$ cycloalkyl, $C_{3-10}$ cycloaryl, $C_{4-6}$ heterocycloalkyl, and $C_{4-10}$ heterocycloaryl with heteroatoms selected from N, O, S; Z is selected from —$CH_2OR_5$, —$COOR_5$ or —$CONR_5R_6$, —$NR_5R_6$, —$NR_5CO—OR_6$, —$NR_5CO—NR_6R_7$, —$NR_5COR_6$, —$NSO_2R_6$ or —$O—CO—NR_5R_6$; $R_5$, $R_6$ and $R_7$ are independently selected from hydrogen or substituted or unsubstituted $C_{5-6}$ aryl, $C_{1-6}$ heteroaryl, $C_{3-8}$ cycloalkyl and $C_{1-6}$ alkyl; wherein when, $R_5$, $R_6$ and $R_7$ are substituted, the one or more substituents are selected from hydrogen, halogen, hydroxy, nitro, cyano, azido, nitroso, oxo (=O), thioxo (=S), —$SO_2$—, amino, hydrazino, formyl, $C_{1-6}$ alkyl, haloalkyl, $C_{1-6}$ alkoxy, $C_{1-6}$ haloalkoxy; $C_{5-6}$ arylalkoxy, $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR^aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, $NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ or —$SO_2R_a$, wherein $R_a$, $R_b$ and $R_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl.

According to another embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein, ---- is absent or a single bond; X is selected from —O— or —N—; n is 0-6; $R_1$ is selected from the group consisting of hydrogen, halogen, $C_{1-6}$ alkyl, $C_{1-6}$ alkoxy, $C_{1-6}$ haloalkyl, $C_{3-8}$ cycloalkyl, $C_{5-6}$ aryl, $C_{1-6}$ heteroaryl, alkoxyalkyl with heteroatoms selected from N, O, S; wherein $C_{1-6}$ alkyl, $C_{3-8}$ cycloalkyl, $C_{5-6}$ aryl, $C_{1-6}$ heteroaryl, is optionally substituted with one or more of the groups selected from hydrogen, $C_{1-6}$ alkyl, halogen, OH; $R_2$ and $R_3$ are independently selected from hydrogen, halogen, hydroxy, nitro, cyano, azido, nitroso, oxo (=O), thioxo (=S), —$SO_2$—, amino, hydrazino, formyl, $C_{1-6}$ alkyl, $C_{1-6}$ haloalkyl, $C_{1-6}$ alkoxy, $C_{1-6}$ haloalkoxy; arylalkoxy; $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR^aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, $NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ or —$SO_2R_a$, wherein $R_a$, $R_b$ and $R_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl.

According to an embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein, ---- is a single bond; X is —N—; n is 0-6; $R_1$ is $C_{1-6}$ alkyl, wherein $C_{1-6}$ alkyl, is optionally substituted with one or more of the groups selected from hydrogen, $C_{1-6}$ alkyl, halogen, OH; $R_2$ and $R_3$ are independently selected from hydrogen, halogen, hydroxy, $C_{1-6}$ alkyl, $C_{1-6}$ haloalkyl, $C_{1-6}$ alkoxy, or $C_{1-6}$ haloalkoxy; $R_4$ is selected from the group consisting of $C_{1-6}$ alkyl, haloalkyl, $C_{3-8}$ cycloalkyl, $C_{5-6}$ aryl, $C_{1-6}$ heteroaryl, alkoxyalkyl with heteroatoms selected from N, O, S; wherein $C_{1-6}$ alkyl, $C_{3-8}$ cycloalkyl, $C_{5-6}$ aryl, $C_{1-6}$ heteroaryl, is optionally substituted with one or more of the groups selected from hydrogen, $C_{1-6}$ alkyl, halogen, OH and cyano; ring A is selected from thienyl, thiazolyl, pyridinyl, pyrimidinyl, pyrrolyl, pyrazinyl, pyridazinyl, pyrazolyl, oxazolyl, imidazolyl, triazolyl, isoxazolyl, isothiazolyl, thiadiazolyl, or furyl; Z is selected from —$CH_2OR_5$, —$COOR_5$ or —$CONR_5R_6$, —$NR_5R_6$, —$NR_5CO—OR_6$, —$NR_5CO—NR_6R_7$, —$NR_5COR_6$, —$NSO_2R_6$ or —$O—CO—NR_5R_6$;

$R_5$, $R_6$ and $R_7$ are independently selected from hydrogen or substituted or unsubstituted $C_{5-6}$ aryl, $C_{1-6}$ heteroaryl, $C_{3-8}$ cycloalkyl and $C_{1-6}$ alkyl; wherein when, $R_5$, $R_6$ and $R_7$ are substituted, the one or more substituents are selected from hydrogen, halogen, hydroxy, nitro, cyano, azido, nitroso, oxo (=O), thioxo (=S), —SO$_2$—, amino, hydrazino, formyl, $C_{1-6}$ alkyl, haloalkyl, $C_{1-6}$ alkoxy, $C_{1-6}$ haloalkoxy; $C_{5-6}$ arylalkoxy; $C_{3-8}$ cycloalkyl, $C_{3-8}$ cycloalkyloxy, $C_{5-6}$ aryl, $C_{2-6}$ heterocyclyl, $C_{2-6}$ heteroaryl, alkylamino, —COOR$_a$, —C(O)R$_b$, —C(S)R$_a$, —C(O)NR$_a$R$_b$, —C(S)NR$_a$R$_b$, —NR$^a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$-OR$_b$—, —SR$_a$, —SOR$_a$ or —SO$_2$R$_a$, wherein R$_a$, R$_b$ and R$_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl.

According to an embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein, ---- is absent; X is —O—; n is 0-6; $R_1$ is $C_{1-6}$ alkyl, wherein $C_{1-6}$ alkyl, is optionally substituted with one or more of the groups selected from hydrogen, $C_{1-6}$ alkyl, halogen, OH; $R_2$ and $R_3$ are independently selected from hydrogen, halogen, hydroxy, $C_{1-6}$ alkyl, $C_{1-6}$ haloalkyl, $C_{1-6}$ alkoxy, or $C_{1-6}$ haloalkoxy; $R_4$ is selected from the group consisting of $C_{1-6}$ alkyl, haloalkyl, $C_{3-8}$ cycloalkyl, $C_{5-6}$ aryl, $C_{1-6}$ heteroaryl, alkoxyalkyl with heteroatoms selected from N, O, S; wherein $C_{1-6}$ alkyl, $C_{3-8}$ cycloalkyl, $C_{5-6}$ aryl, $C_{1-6}$ heteroaryl, is optionally substituted with one or more of the groups selected from hydrogen, $C_{1-6}$ alkyl, halogen, OH and cyano; ring A is selected from thienyl, thiazolyl, pyridinyl, pyrimidinyl, pyrrolyl, pyrazinyl, pyridazinyl, pyrazolyl, oxazolyl, triazolyl, imidazolyl, isoxazolyl, isothiazolyl, thiadiazolyl, or furyl; Z is selected from —CH$_2$OR$_5$, —COOR$_5$ or —CONR$_5$R$_6$, —NR$_5$R$_6$, —NR$_5$CO—OR$_6$, —NR$_5$CO—NR$_6$R$_7$, —NR$_5$COR$_6$, —NSO$_2$R$_6$ or —O—CO—NR$_5$R$_6$; $R_5$, $R_6$ and $R_7$ are independently selected from hydrogen or substituted or unsubstituted $C_{5-6}$ aryl, $C_{1-6}$ heteroaryl, $C_{3-8}$ cycloalkyl and $C_{1-6}$ alkyl; wherein when, $R_5$, $R_6$ and $R_7$ are substituted, the one or more substituents are selected from hydrogen, halogen, hydroxy, nitro, cyano, azido, nitroso, oxo (=O), thioxo (=S), —SO$_2$—, amino, hydrazino, formyl, $C_{1-6}$ alkyl, haloalkyl, $C_{1-6}$ alkoxy, $C_{1-6}$ haloalkoxy; $C_{5-6}$ arylalkoxy; $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$^a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$-OR$_b$—, —SR$_a$, —SOR$_a$ or —SO$_2$R$_a$, wherein R$_a$, R$_b$ and R$_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl.

According to an embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein, ---- is a single bond; X is —N—; n is 1-2; $R_1$ is $C_{1-4}$ alkyl; $R_2$ and $R_3$ are independently selected from hydrogen, $C_{1-4}$ alkyl, or $C_{1-4}$ alkoxy; $R_4$ is selected from the group consisting of $C_{3-8}$ cycloalkyl, or $C_{5-6}$ aryl, wherein $C_{3-8}$ cycloalkyl, or $C_{5-6}$ aryl, is substituted with one or more of the groups selected from hydrogen, $C_{1-6}$ alkyl, halogen, and cyano; ring A is selected from thienyl, thiazolyl, pyridinyl, pyrimidinyl, pyrrolyl, pyrazinyl, pyridazinyl, pyrazolyl, oxazolyl, triazolyl, imidazolyl, isoxazolyl, isothiazolyl, thiadiazolyl, or furyl; Z is selected from —CH$_2$OR$_5$, —COOR$_5$ or —CONR$_5$R$_6$, —NR$_5$R$_6$, —NR$_5$CO—OR$_6$, —NR$_5$CO—NR$_6$R$_7$, —NR$_5$COR$_6$, —NSO$_2$R$_6$ or —O—CO—NR$_5$R$_6$; $R_5$, $R_6$ and $R_7$ are independently selected from hydrogen or substituted or unsubstituted $C_{5-6}$ aryl, $C_{1-6}$ heteroaryl, $C_{3-8}$ cycloalkyl and $C_{1-6}$ alkyl; wherein when, $R_5$, $R_6$ and $R_7$ are substituted, the one or more substituents are selected from hydrogen, halogen, hydroxy, nitro, cyano, azido, nitroso, oxo (=O), thioxo (=S), —SO$_2$—, amino, hydrazino, formyl, $C_{1-6}$ alkyl, haloalkyl, $C_{1-6}$ alkoxy, $C_{1-6}$ haloalkoxy; $C_{5-6}$ arylalkoxy; $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —COOR$_a$, —C(O)R$_b$, —C(S)R$_a$, —C(O)NR$_a$R$_b$, —C(S)NR$_a$R$_b$, —NR$^a$C(O)NR$_b$R$_c$, NR$_a$C(S)NR$_b$R$_c$, —N(R$_a$)SOR$_b$, —N(R$_a$)SO$_2$R$_b$, —NR$_a$C(O)OR$_b$, —NR$_a$R$_b$, —NR$_a$C(O)R$_b$—, NR$_a$C(S)R$_b$—, —SONR$_a$R$_b$—, —SO$_2$NR$_a$R$_b$—, —OR$_a$, —OR$_a$C(O)OR$_b$—, —OC(O)NR$_a$R$_b$, OC(O)R$_a$, —OC(O)NR$_a$R$_b$—, —R$_a$NR$_b$R$_c$, —R$_a$-OR$_b$—, —SR$_a$, —SOR$_a$ or —SO$_2$R$_a$, wherein R$_a$, R$_b$ and R$_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl.

According to another embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein, ---- is absent; X is —S—; n is 1-2; $R_1$ is $C_{1-4}$ alkyl; $R_2$ and $R_3$ are independently selected from hydrogen, $C_{1-4}$ alkyl, or $C_{1-4}$ alkoxy; $R_4$ is selected from the group consisting of $C_{3-8}$ cycloalkyl, or $C_{5-6}$ aryl, wherein $C_{3-8}$ cycloalkyl, or $C_{5-6}$ aryl, is substituted with one or more of the groups selected from hydrogen, $C_{1-6}$ alkyl, halogen, and cyano; ring A is selected from thienyl, thiazolyl, pyridinyl, pyrimidinyl, pyrrolyl, pyrazinyl, pyridazinyl, pyrazolyl, oxazolyl, triazolyl, imidazolyl, isoxazolyl, isothiazolyl, thiadiazolyl, or furyl; Z is selected from —$CH_2OR_5$, —$COOR_5$ or —$CONR_5R_6$, —$NR_5R_6$, —$NR_5CO$—$OR_6$, —$NR_5CO$—$NR_6R_7$, —$NR_5COR_6$, —$NSO_2R_6$ or —O—CO—$NR_5R_6$; $R_5$, $R_6$ and $R_7$ are independently selected from hydrogen or substituted or unsubstituted $C_{5-6}$ aryl, $C_{1-6}$ heteroaryl, $C_{3-8}$ cycloalkyl and $C_{1-6}$ alkyl; wherein when, $R_5$, $R_6$ and $R_7$ are substituted, the one or more substituents are selected from hydrogen, halogen, hydroxy, nitro, cyano, azido, nitroso, oxo (=O), thioxo (=S), —$SO_2$—, amino, hydrazino, formyl, $C_{1-6}$ alkyl, haloalkyl, $C_{1-6}$ alkoxy, $C_{1-6}$ haloalkoxy; $C_{5-6}$ arylalkoxy; $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR^aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, $NR_aC(S)R_b$—, —$SONR_aR_b$—, —$SO_2NR_aR_b$—, —$OR_a$, —$OR_aC(O)OR_b$—, —OC(O)$NR_aR_b$, OC(O)$R_a$, —OC(O)$NR_aR_b$—, —$R_aNR_bR_c$, —$R_a$—$OR_b$—, —$SR_a$, —$SOR_a$ or —$SO_2R_a$, wherein $R_a$, $R_b$ and $R_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl or $C_{1-6}$ heteroarylalkyl.

According to an embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein, ---- is a single bond; X is —N—; n is 1-2; $R_1$ is $C_1$ alkyl; $R_2$ and $R_3$ are independently selected from hydrogen, $C_{1-2}$ alkyl, or $C_{1-2}$ alkoxy; $R_4$ is selected from the group consisting of $C_{3-8}$ cycloalkyl, or $C_{5-6}$ aryl, wherein $C_{3-8}$ cycloalkyl, or $C_{5-6}$ aryl, is substituted with one or more of the groups selected from hydrogen, $C_{1-6}$ alkyl, halogen, and cyano; ring A is selected from thienyl, thiazolyl, pyridinyl, pyrimidinyl, pyrrolyl, pyrazinyl, pyridazinyl, or pyrazolyl; Z is selected from —$CH_2OR_5$, —$COOR_5$, —$CONR_5R_6$, or —$NR_5R_6$; $R_5$, and $R_6$ are independently selected from hydrogen or substituted or unsubstituted $C_{5-6}$ aryl, and $C_{1-6}$ alkyl; wherein when, $R_5$, and $R_6$ are substituted, the substituents are selected from hydrogen, halogen, hydroxy, nitro, cyano or $C_{1-6}$ alkyl.

According to an embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein, ---- is absent; X is —O—; n is 1-2; $R_1$ is $C_1$ alkyl; $R_2$ and $R_3$ are independently selected from hydrogen, $C_{1-2}$ alkyl, or $C_{1-2}$ alkoxy; $R_4$ is selected from the group consisting of $C_{3-8}$ cycloalkyl, or $C_{5-6}$ aryl, wherein $C_{3-8}$ cycloalkyl, or $C_{5-6}$ aryl, is substituted with one or more of the groups selected from hydrogen, $C_{1-6}$ alkyl, halogen, and cyano; ring A is selected from thienyl, thiazolyl, pyridinyl, pyrimidinyl, pyrrolyl, pyrazinyl, pyridazinyl, or pyrazolyl; Z is selected from —$CH_2OR_5$, —$COOR_5$, —$CONR_5R_6$, or —$NR_5R_6$; $R_5$, and $R_6$ are independently selected from hydrogen or substituted or unsubstituted $C_{5-6}$ aryl, and $C_{1-6}$ alkyl; wherein when, $R_5$, and $R_6$ are substituted, the substituents are selected from hydrogen, halogen, hydroxy, nitro, cyano or $C_{1-6}$ alkyl.

According to an embodiment, the present disclosure relates to the compound of Formula (I) or its stereoisomers, pharmaceutically acceptable salts, complexes, hydrates, solvates, tautomers, polymorphs, racemic mixtures, optically active forms and pharmaceutically active derivative thereof, wherein, ---- is absent; X is —S—; n is 1-2; $R_1$ is $C_1$ alkyl; $R_2$ and $R_3$ are independently selected from hydrogen, $C_{1-2}$ alkyl, or $C_{1-2}$ alkoxy; $R_4$ is selected from the group consisting of $C_{3-8}$ cycloalkyl, or $C_{5-6}$ aryl, wherein $C_{3-8}$ cycloalkyl, or $C_{5-6}$ aryl, is substituted with one or more of the groups selected from hydrogen, $C_{1-6}$ alkyl, halogen, and cyano; ring A is selected from thienyl, thiazolyl, pyridinyl, pyrimidinyl, pyrrolyl, pyrazinyl, pyridazinyl, or pyrazolyl; Z is selected from —$CH_2OR_5$, —$COOR_5$, —$CONR_5R_6$, or —$NR_5R_6$; $R_5$, and $R_6$ are independently selected from hydrogen or substituted or unsubstituted $C_{5-6}$ aryl, and $C_{1-6}$ alkyl; wherein when, $R_5$, and $R_6$ are substituted, the substituents are selected from hydrogen, halogen, hydroxy, nitro, cyano or $C_{1-6}$ alkyl.

According to another embodiment, the present disclosure relates to the compound of the Formula (I),

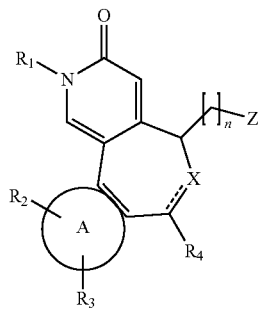

or its stereoisomers, pharmaceutically acceptable salts, complexes, hydrates, solvates, tautomers, polymorphs, racemic mixtures, optically active forms and pharmaceutically active derivative thereof, wherein ---- is absent or single bond; X is selected from —N—, —O—, or —S—; n is 1-2; $R_1$ is $C_1$ alkyl; $R_2$ and $R_3$ are independently selected from hydrogen, or $C_{1-2}$ alkyl; $R_4$ is selected from the group consisting of $C_{3-8}$ cycloalkyl, or $C_{5-6}$ aryl, wherein $C_{3-8}$ cycloalkyl, or $C_{5-6}$ aryl, is substituted with one or more of the groups selected from hydrogen, $C_{1-6}$ alkyl, halogen, and cyano; ring A is selected from thienyl, thiazolyl, pyridinyl, pyrimidinyl; Z is selected from —$CH_2OR_5$, —$COOR_5$, —$CONR_5R_6$, or —$NR_5R_6$; $R_5$, and $R_6$ are independently selected from hydrogen or substituted or unsubstituted $C_{5-6}$ aryl, and $C_{1-6}$ alkyl; wherein when, $R_5$, and $R_6$ are substituted, the substituents are selected from hydrogen, halogen, hydroxy, nitro, cyano or $C_{1-6}$ alkyl.

According to another embodiment, the present disclosure relates to the compound of the Formula (I),

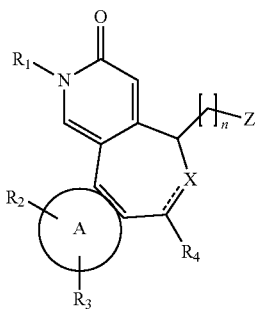

or its stereoisomers, pharmaceutically acceptable salts, complexes, hydrates, solvates, tautomers, polymorphs, racemic mixtures, optically active forms and pharmaceutically active derivative thereof, wherein ---- is absent or single bond; X is selected from —N— or —O—; n is 1-2; $R_1$ is $C_1$ alkyl; $R_2$ and $R_3$ are independently selected from hydrogen, or $C_{1-2}$ alkyl; $R_4$ is selected from the group consisting of $C_{3-8}$ cycloalkyl, or $C_{5-6}$ aryl, wherein $C_{3-8}$ cycloalkyl, or $C_{5-6}$ aryl, is substituted with one or more of the groups selected from hydrogen, $C_{1-6}$ alkyl, halogen, and cyano; ring A is selected from thienyl, thiazolyl, pyridinyl, pyrimidinyl; Z is selected from —$CH_2OR_5$, —$COOR_5$, —$CONR_5R_6$, or —$NR_5R_6$; $R_5$, and $R_6$ are independently selected from hydrogen or substituted or unsubstituted $C_{5-6}$ aryl, and $C_{1-6}$ alkyl; wherein when, $R_5$, and $R_6$ are substituted, the substituents are selected from hydrogen, halogen, hydroxy, nitro, cyano or $C_{1-6}$ alkyl.

According to an embodiment, the present disclosure relates to a compound of Formula I

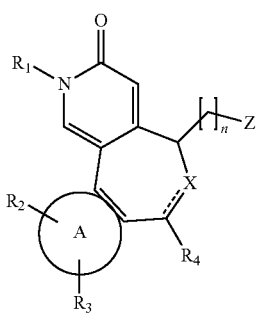

(I)

their analogs, tautomeric forms, stereoisomers, polymorphs, solvates, intermediates, pharmaceutically acceptable salts, pharmaceutical compositions, metabolites and prodrugs thereof;
wherein
$R_1$ represents substituted or unsubstituted alkyl or cycloalkyl; X represents —O— or —N—; A represents 5 or 6 membered heteroaryl ring such as thienyl, thiazolyl, pyridinyl, pyrimidinyl, pyrrolyl, pyrazinyl, pyridazinyl, oxazolyl, triazolyl, isoxazolyl, isothiazolyl, thiadiazolyl, furyl and the like; $R_4$ represent hydrogen or substituted or unsubstituted aryl, heteroaryl, cycloalkyl, alkyl and haloalkyl; Z represents —$CH_2OR_5$, —$COOR_5$ or —$CONR_5R_6$, —$NR_5R_6$, —$NR_5CO$—$OR_6$, —$NR_5CO$—$NR_6R_7$, —$NR_5COR_6$, —$NSO_2R_6$ and —O—CO—$NR_5R_6$; $R_5$, $R_6$ and $R_7$ represent hydrogen or substituted or unsubstituted aryl, heteroaryl, cycloalkyl and alkyl; n represents an integer from 0-6; $R_2$ and $R_3$ represent substitution which are independently selected from hydrogen, be one or more are selected from but not limited to halogens such as fluorine, chlorine, bromine, iodine; hydroxy, nitro, cyano, azido, nitroso, oxo (=O), thioxo (=S), —$SO_2$—, amino, hydrazino, formyl, alkyl, haloalkyl group such as trifluoromethyl, tribromomethyl, trichloromethyl and the like; alkoxy, haloalkoxy such as —$OCH_2Cl$ and the like; arylalkoxy such as benzyloxy, phenylethoxy and the like; cycloalkyl, cycloalkyloxy, aryl, heterocyclyl, heteroaryl, alkylamino, —$COOR_a$, —$C(O)R_b$, —$C(S)R_a$, —$C(O)NR_aR_b$, —$C(S)NR_aR_b$, —$NR^aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, $NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ in each of the above groups can be hydrogen, optionally substituted groups selected from alkyl, cycloalkyl, aryl, arylalkyl, heterocyclyl, heteroaryl and heteroarylalkyl. The substituents are optionally further substituted by one or more substituents as defined above; when the groups $R_4$, $R_5$, $R_6$ and $R_7$ are substituted, the substituents which may be one or more are selected from but not limited to halogens such as fluorine, chlorine, bromine, iodine; hydroxy, nitro, cyano, azido, nitroso, oxo (=O), thioxo (=S), —$SO_2$-amino, hydrazino, formyl, alkyl, haloalkyl group such as trifluoromethyl, tribromomethyl, trichloromethyl and the like; alkoxy, haloalkoxy such as —$OCH_2Cl$ and the like; arylalkoxy such as benzyloxy, phenylethoxy and the like; cycloalkyl, cycloalkyloxy, aryl, heterocyclyl, heteroaryl, alkylamino, —$COOR_a$, —$C(O)R_b$, —$C(S)R_a$, —$C(O)NR_aR_b$, —$C(S)NR_aR_b$, —$NR^aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$—, $NR_aC(S)R_b$—, —$SONR_aR_b$—, —$SO_2NR_aR_b$—, —$OR_a$, —$OR_aC(O)OR_b$—, —$OC(O)NR_aR_b$, $OC(O)R_a$, —$OC(O)NR_aR_b$—, —$R_aNR_bR_c$, —$R_aOR_b$—, —$SR_a$, —$SOR_a$ and —$SO_2R_a$, wherein $R_a$, $R_b$ and $R_c$ in each of the above groups can be hydrogen, optionally substituted groups selected from alkyl, cycloalkyl, aryl, arylalkyl, heterocyclyl, heteroaryl and heteroarylalkyl. The substituents are optionally further substituted by one or more substituents as defined above.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, $R_1$ is methyl.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, $R_2$ is hydrogen, methyl or methoxy.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, $R_3$ is methyl or hydrogen.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, $R_4$ is selected from, $C_3$ cycloalkyl or $C_6$ aryl, are independently unsubstituted or substituted with up to three substituents independently selected from, chlorine, methyl and cyano.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, X is —N—.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, X is —O—.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, wherein, n is 1 or 2.

According to an embodiment, the present disclosure relates to a compound of Formula I or its stereoisomers, pharmaceutically acceptable salts, complexes, hydrates, solvates, tautomers, polymorphs, racemic mixtures, optically active forms and pharmaceutically active derivative thereof, which is selected from a group consisting of:

a. ±Ethyl 2-(4-(4-chlorophenyl)-2,3,9-trimethyl-8-oxo-8,9-dihydro-6H-pyrido[4,3-c]thieno[2,3-e]azepin-6-yl)acetate
b. ±2-(4-(4-chlorophenyl)-2,3,9-trimethyl-8-oxo-8,9-dihydro-6H-pyrido[4,3-c]thieno[2,3-e]azepin-6-yl)-N-ethylacetamide
c. (S)-2-(4-(4-chlorophenyl)-2,3,9-trimethyl-8-oxo-8,9-dihydro-6H-pyrido[4,3-c]thieno[2,3-e]azepin-6-yl)-N-ethylacetamide
d. (R)-2-(4-(4-chlorophenyl)-2,3,9-trimethyl-8-oxo-8,9-dihydro-6H-pyrido[4,3-c]thieno[2,3-e]azepin-6-yl)-N-ethylacetamide
e. ±2-(4-(4-chlorophenyl)-2,3,9-trimethyl-8-oxo-8,9-dihydro-6H-pyrido[4,3-c]thieno[2,3-e]azepin-6-yl)acetamide
f. (S)-2-(4-(4-chlorophenyl)-2,3,9-trimethyl-8-oxo-8,9-dihydro-6H-pyrido[4,3-c]thieno[2,3-e]azepin-6-yl)acetamide
g. (R)-2-(4-(4-chlorophenyl)-2,3,9-trimethyl-8-oxo-8,9-dihydro-6H-pyrido[4,3-c]thieno[2,3-e]azepin-6-yl)acetamide
h. ±2-(4-(4-chlorophenyl)-2,3,9-trimethyl-8-oxo-8,9-dihydro-6H-pyrido[4,3-c]thieno[2,3-e]azepin-6-yl)-N-(4-hydroxyphenyl)acetamide
i. (S)-2-(4-(4-chlorophenyl)-2,3,9-trimethyl-8-oxo-8,9-dihydro-6H-pyrido[4,3-c]thieno[2,3-e]azepin-6-yl)-N-(4-hydroxyphenyl)acetamide
j. (R)-2-(4-(4-chlorophenyl)-2,3,9-trimethyl-8-oxo-8,9-dihydro-6H-pyrido[4,3-c]thieno[2,3-e]azepin-6-yl)-N-(4-hydroxyphenyl)acetamide
k. (R)-2-(4-(4-cyanophenyl)-2,3,9-trimethyl-8-oxo-8,9-dihydro-6H-pyrido[4,3-c]thieno[2,3-e]azepin-6-yl)-N-ethylacetamide.
l. ±Ethyl 2-(4-(4-chlorophenyl)-2,9-dimethyl-8-oxo-8,9-dihydro-6H-pyrido[4,3-c]thiazolo[5,4-e]azepin-6-yl)acetate
m. ±2-(4-(4-chlorophenyl)-2,9-dimethyl-8-oxo-8,9-dihydro-6H-pyrido[4,3-c]thiazolo[5,4-e]azepin-6-yl)-N-ethylacetamide
n. (R)-2-(4-(4-chlorophenyl)-2,9-dimethyl-8-oxo-8,9-dihydro-6H-pyrido[4,3-c]thiazolo[5,4-e]azepin-6-yl)-N-ethylacetamide
o. (S)-2-(4-(4-chlorophenyl)-2,9-dimethyl-8-oxo-8,9-dihydro-6H-pyrido[4,3-c]thiazolo[5,4-e]azepin-6-yl)-N-ethylacetamide
p. ±Ethyl 2-(5-(4-chlorophenyl)-10-methyl-9-oxo-9,10-dihydro-7H-dipyrido[3,2-c: 3',4'-e]azepin-7-yl)acetate.
q. ±ethyl 2-(4-(cyclopropylmethyl)-2,3,9-trimethyl-8-oxo-8,9-dihydro-6H-pyrido[4,3-c]thieno[2,3-e]azepin-6-yl)acetate
r. ±2-(4-(cyclopropylmethyl)-2,3,9-trimethyl-8-oxo-8,9-dihydro-6H-pyrido[4,3-c]thieno[2,3-e]azepin-6-yl)-N-ethylacetamide
s. ±Ethyl-2-(7-(4-chlorophenyl)-9-methoxy-2-methyl-3-oxo-3,5-dihydro-2H-dipyrido[4,3-c:3',4'-e]azepin-5-yl)acetate
t. ±2-(7-(4-chlorophenyl)-9-methoxy-2-methyl-3-oxo-3,5-dihydro-2H-dipyrido[4,3-c:3',4'-e]azepin-5-yl)-N-ethylacetamide
u. (S)-2-(7-(4-chlorophenyl)-9-methoxy-2-methyl-3-oxo-3,5-dihydro-2H-dipyrido[4,3-c:3',4'-e]azepin-5-yl)-N-ethylacetamide
v. (R)-2-(7-(4-chlorophenyl)-9-methoxy-2-methyl-3-oxo-3,5-dihydro-2H-dipyrido[4,3-c:3',4'-e]azepin-5-yl)-N-ethylacetamide
w. ±Ethyl 2-(4-(4-chlorophenyl)-3,9-dimethyl-8-oxo-3,6,8,9-tetrahydropyrazolo[3,4-c]pyrido[3,4-e]azepin-6-yl)acetate
x. ±2-(4-(4-chlorophenyl)-3,9-dimethyl-8-oxo-3,6,8,9-tetrahydropyrazolo[3,4-c]pyrido[3,4-e]azepin-6-yl)-N-ethylacetamide
y. (R)-2-(4-(4-chlorophenyl)-3,9-dimethyl-8-oxo-3,6,8,9-tetrahydropyrazolo[3,4-c]pyrido[3,4-e]azepin-6-yl)-N-ethylacetamide
z. (S)-2-(4-(4-chlorophenyl)-3,9-dimethyl-8-oxo-3,6,8,9-tetrahydropyrazolo[3,4-c]pyrido[3,4-e]azepin-6-yl)-N-ethylacetamide
aa. ±Ethyl-2-(4-(4-chlorophenyl)-2,3,9-trimethyl-8-oxo-4,6,8,9-tetrahydrothieno[2',3':5,6]oxepino[4,3-c]pyridin-6-yl)acetate
bb. ±2-(4-(4-chlorophenyl)-2,3,9-trimethyl-8-oxo-4,6,8,9-tetrahydrothieno[2',3':5,6]oxepino[4,3-c]pyridin-6-yl)-N-ethylacetamide
cc. 2-(4S,6S)(4-(4-chlorophenyl)-2,3,9-trimethyl-8-oxo-4,6,8,9-tetrahydrothieno[2',3':5,6]oxepino[4,3-c]pyridin-6-yl)-N-ethylacetamide
dd. 2-(4R,6R)(4-(4-chlorophenyl)-2,3,9-trimethyl-8-oxo-4,6,8,9-tetrahydrothieno[2',3':5,6]oxepino[4,3-c]pyridin-6-yl)-N-ethylacetamide
ee. ±2-(4-(4-chlorophenyl)-2,3,9-trimethyl-8-oxo-4,6,8,9-tetrahydrothieno[2',3':5,6]oxepino[4,3-c]pyridin-6-yl)acetamide
ff. 2-((4S,6S)-4-(4-chlorophenyl)-2,3,9-trimethyl-8-oxo-4,6,8,9-tetrahydrothieno[2',3':5,6]oxepino[4,3-c]pyridin-6-yl)acetamide
gg. 2-((4R,6R)-4-(4-chlorophenyl)-2,3,9-trimethyl-8-oxo-4,6,8,9-tetrahydrothieno[2',3':5,6]oxepino[4,3-c]pyridin-6-yl)acetamide
hh. ±4-(4-chlorophenyl)-6-(2-hydroxyethyl)-2,3,9-trimethyl-4,9-dihydrothieno[2',3':5,6]oxepino[4,3-c]pyridin-8(6H)-one
ii. (4S,6S)-4-(4-chlorophenyl)-6-(2-hydroxyethyl)-2,3,9-trimethyl-4,9-dihydrothieno[2',3':5,6]oxepino[4,3-c]pyridin-8(6H)-one jj. (4R,6R)-4-(4-chlorophenyl)-6-(2-hydroxyethyl)-2,3,9-trimethyl-4,9-dihydrothieno[2',3':5,6]oxepino[4,3-c]pyridin-8(6H)-one kk. ±ethyl 2-(4-(4-chlorophenyl)-3,9-dimethyl-8-oxo-3,6,8,9-tetrahydropyrazolo[3,4-c]pyrido[3,4-e]azepin-6-yl)acetate ll. ±2-(4-(4-chlorophenyl)-3,9-dimethyl-8-oxo-4,6,8,9-tetrahydro-3H-pyrazolo[4',3':5,6]oxepino[4,3-c]pyridin-6-yl)-N-ethylacetamide According to an embodiment, the present disclosure relates to a process of preparation of compound of Formula I or its stereoisomers, pharmaceutically acceptable salts, complexes, hydrates, solvates, tautomers, polymorphs, racemic mixtures, optically active forms and pharmaceutically active derivative thereof.

According to an embodiment, the present disclosure relates to a pharmaceutical composition including a compound of Formula (I), or its stereoisomers, pharmaceutically acceptable salts, complexes, hydrates, solvates, tautomers, polymorphs, racemic mixtures, optically active forms and pharmaceutically active derivative thereof, and at least one pharmaceutically acceptable carrier, diluent, or excipient.

According to an embodiment, the present disclosure relates to a pharmaceutical composition including a compound of Formula (I), or its stereoisomers, pharmaceutically acceptable salts, complexes, hydrates, solvates, tautomers, polymorphs, racemic mixtures, optically active forms and pharmaceutically active derivative thereof, with pharmaceutically acceptable carrier, optionally in combination with one or more other pharmaceutical compositions.

According to an embodiment, the present disclosure relates to a pharmaceutical composition including a compound of Formula (I), or its stereoisomers, pharmaceutically acceptable salts, complexes, hydrates, solvates, tautomers, polymorphs, racemic mixtures, optically active forms and pharmaceutically active derivative thereof, wherein the composition is in the form of a tablet, capsule, powder, syrup, solution, aerosol or suspension.

According to an embodiment, the present disclosure relates to the use of a compound of Formula (I) and pharmaceutical composition including a compound of Formula (I), or its stereoisomers, pharmaceutically acceptable salts, complexes, hydrates, solvates, tautomers, polymorphs, racemic mixtures, optically active forms and pharmaceutically active derivative thereof, in the manufacture of a medicament for the treatment and/or prevention of diseases and/or disorders in which aberrant, abnormal or deregulated activity of BET family of bromodomain containing proteins; in particular BRD2, BRD3, BRD4 and BRDT proteins.

According to an embodiment, the present disclosure relates to the use of a compound of Formula (I) and pharmaceutical composition including a compound of Formula (I) or its stereoisomers, pharmaceutically acceptable salts, complexes, hydrates, solvates, tautomers, polymorphs, racemic mixtures, optically active forms and pharmaceutically active derivative thereof, in the manufacture of a medicament for the production of an anti-cancer effect in a warm-blooded animal such as human.

According to an embodiment, the present disclosure relates to a method for treating a variety of diseases or conditions related to systemic or tissue inflammation, inflammatory responses to infection or hypoxia, cellular activation and proliferation, lipid metabolism, fibrosis and in the prevention and treatment of viral infections.

According to an embodiment, the present disclosure relates to a method for treating cancer in patients including administration of a therapeutically effective amount of a compound of Formula (I).

According to an embodiment, the present disclosure relates to a method for treating proliferative conditions or cancer, comprising administering to a subject suffering from proliferative conditions or cancer, a therapeutically effective amount of a compound of Formula (I), in the presence or absence of other clinically relevant cytotoxic agents or non-cytotoxic agents to a mammal in need thereof.

According to an embodiment, the present disclosure relates to a method for treating a disorder caused by, associated with or accompanied by disruptions of cell proliferation and/or angiogenesis and the subsequent metastasis including administration of a therapeutically effective amount of a compound of Formula (I).

According to an embodiment, the present disclosure relates to a method for treating cancer in patient including administration of effective amount of compounds of Formula (I). The cancer can be either a hematologic malignancy or solid tumor. Hematological malignancy is selected from the group consisting of B-cell lymphoma, T-cell lymphoma and leukemia. In the case of solid tumors, the tumors are selected from the group consisting of breast cancer, lung cancer, ovarian cancer, prostate cancer, head cancer, neck cancer, renal cancer, gastric cancer, colon cancer, pancreatic cancer and brain cancer.

According to an embodiment, the present disclosure relates to a method for treating and/or preventing a neurodegenerative disease or disorder comprising administering, to a patient in need of treatment, a therapeutically effectively amount of a composition comprising a compound of Formula I and a pharmaceutically acceptable carrier.

In one aspect of this embodiment, the invention provides a compound of Formula I for use in treating and/or preventing a neurodegenerative disorder or condition. In a related aspect, the invention provides for the use of a compound of Formula I for the manufacture of a medicament for treating and/or preventing a neurodegenerative disorder or condition.

According to an embodiment, the present disclosure relates to the compounds of Formula (I) useful for treating proliferative diseases. A proliferative disease includes, for example, a tumor disease and/or metastasis.

According to an embodiment, the compounds of the present disclosure are useful for treating a proliferative disease that is refractory to the treatment with other chemotherapeutics; or a tumor that is refractory to treatment with other therapeutics due to multidrug resistance.

According to an embodiment, the present disclosure relates to a method of treatment of cancer, said method comprising administering a combination of the compound or the pharmaceutical composition with other clinically relevant immune modulators to a mammal in need thereof.

According to an embodiment, the compounds of the present invention are able to slow tumor growth, stop tumor growth or bring about the regression of tumors and to prevent the formation of tumor metastasis (including micrometastatis) and the growth of metastasis (including micrometastatis). In addition, they can be used in epidermal hyper proliferation.

The compound of Formula I of the present invention can be used as a prophylactic or therapeutic agent for cancer. Examples of the cancer not restricted include breast cancer, prostate cancer, pancreatic cancer, gastric cancer, lung cancer, colon cancer, rectal cancer, esophagus cancer, duodenal cancer, tongue cancer, pharyngeal cancer, brain tumor, neurinoma, non-small cell lung cancer, small cell lung cancer, liver cancer, kidney cancer, bile duct cancer, uterine body cancer, cervical cancer, ovarian cancer, urinary bladder cancer, skin cancer, hemangioma, malignant lymphoma, malignant melanoma, thyroid cancer, bone tumor, vascular fibroma, retinoblastoma, penile cancer, pediatric solid cancer, lymphoma, myeloma and leukemia (including, for example acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL) or hairy cell leukemia).

The compound of Formula I of the present invention can be used as a prophylactic or therapeutic agent for various chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

In one embodiment, the invention provides a method of inhibiting bromodomain activity comprising administering, to a patient in need of treatment, an amount of a composition comprising a compound of Formula I and a pharmaceutically acceptable carrier sufficient to inhibit bromodomain activity.

In one aspect of this embodiment, the invention provides a compound of Formula I for use in inhibiting bromodomain. In a related aspect, the invention provides for the use of a compound of Formula I for the manufacture of a medicament for inhibiting bromodomain.

In one embodiment, the invention provides a method of treating and/or preventing a neurodegenerative disease or disorder comprising administering, to a patient in need of treatment, a therapeutically effectively amount of a composition comprising a compound of Formula I and a pharmaceutically acceptable carrier. In one aspect of this embodiment, the invention provides a compound of Formula I for use in treating and/or preventing a neurodegenerative disorder or condition. In a related aspect, the invention provides for the use of a compound of Formula I for the manufacture of a medicament for treating and/or preventing a neurodegenerative disorder or condition.

In another aspect, the compound may be administered in combination therapy by combining the compound of Formula (I) with one or more separate agents, not limited to targets such as DNA methyltransferase, heat shock proteins (e.g. HSP90) kinases, and other matrix metalloproteinases.

"Combination therapy" includes the administration of the subject compounds in further combination with other biologically active ingredients (such as vinblastine, afatinib, nilotinib, vemarafinib, aflibercept, axitinib, dasatinib, sorafenib, bosutinib, crizotinib, but are not limited to, different antineoplastic agent) and non-drug therapies (such as, but are not limited to, surgery or radiation treatment). The compounds described herein can be used in combination with other pharmaceutically active compounds, preferably, which will enhance the effect of the compounds of the invention. The compounds can be administered simultaneously or sequentially to the other drug therapy.

In another aspect, the subject compounds may be combined with the antineoplastic agents (e.g. small molecules, monoclonal antibodies, antisense RNA and fusion proteins) that inhibit one or more biological targets. Such combination may enhance therapeutic efficacy over the efficacy achieved by any of the agents alone and may prevent or delay the appearance of resistant variants.

In another aspect, the subject compounds may be combined with immunoncology drugs not restricting to PDL-1, IDO, TDO, CTLA4 or any other drugs which is involved in the immune modulation.

A term once described, the same meaning applies for it, throughout the patent.

Scheme:

According to an embodiment, the present disclosure relates to a process as shown in the following scheme-1, for the preparation of compounds of the Formula (I), wherein all the groups are as defined earlier.

Scheme 1

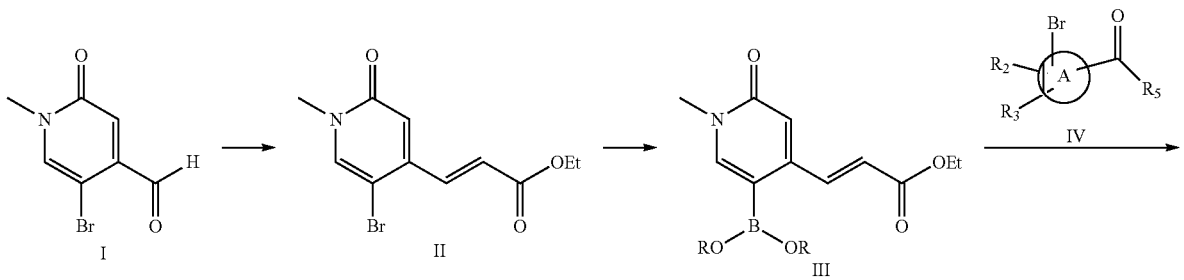

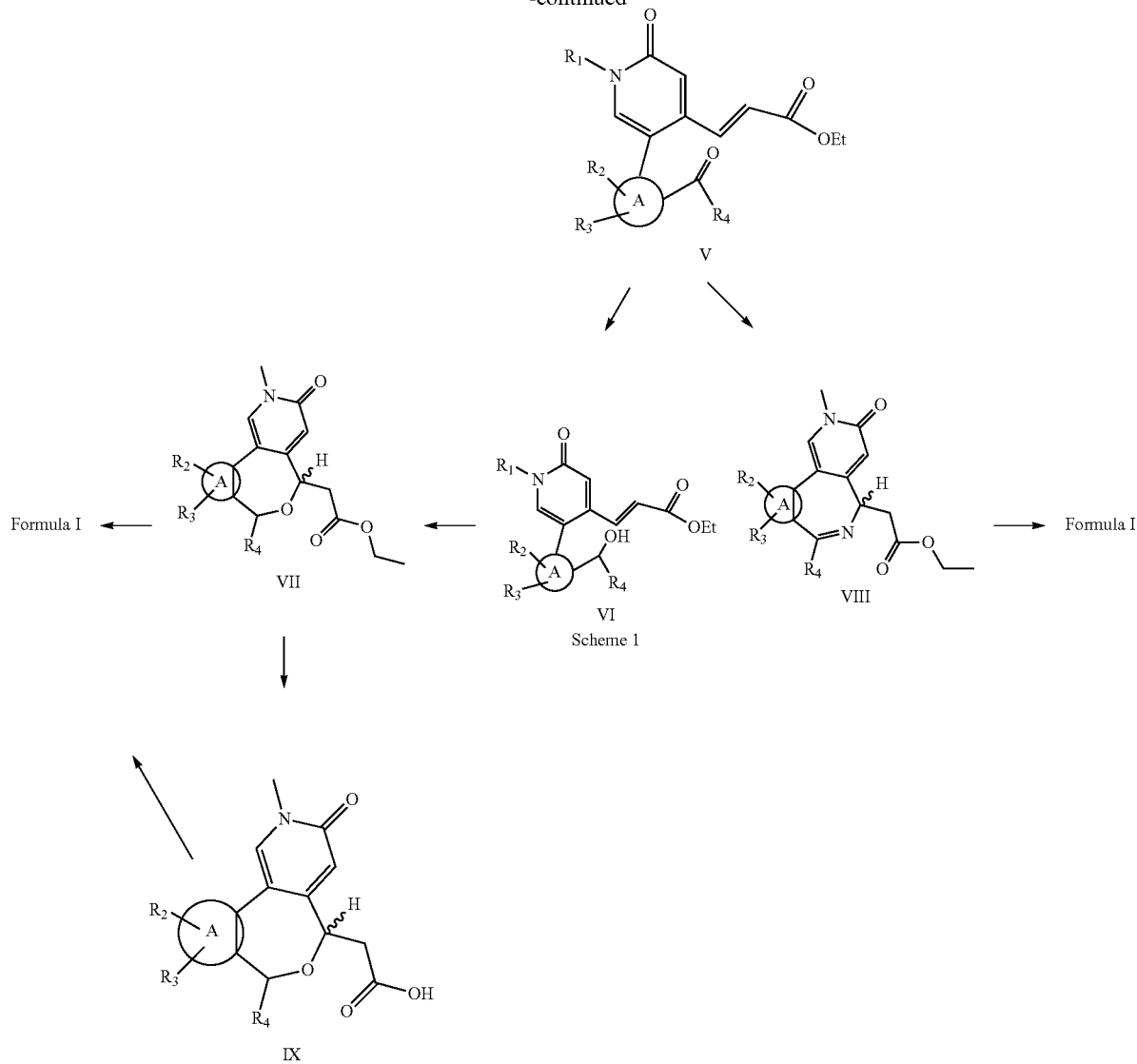

Scheme 1

The said process for the preparation of the compounds of formula (I) comprises of the following:

The compound I was converted to compound II under standard conditions either using malonic acid or wittig reagent. Compound II was treated with boron reagent in the presence of Pd catalyst and suitable ligand to form III. Reaction of III with the intermediate IV in the presence of Pd catalyst and suitable ligand yielded V. Compound IV under standard carbonyl reductions using sodium borohydride or sodium cyanoborohydride or like to give the corresponding alcohol VI. Intramolecular cyclization of VI using bases such as inorganic or organic bases yielded VII. Further exploration of VII gives compound of formula 1. Hydrolysis of VII with inorganic base such as NaOH and like gives the corresponding acid IX, which on further exploration gives compound of Formula I. Treating compound V with ammonium acetate or the like in polar protic solvent such as methanol, ethanol or the like gives VIII. Further exploration of VIII gives compound of Formula 1. Where in $R^1$, $R^2$, $R^3$, $R^4$ and Z are as described above.

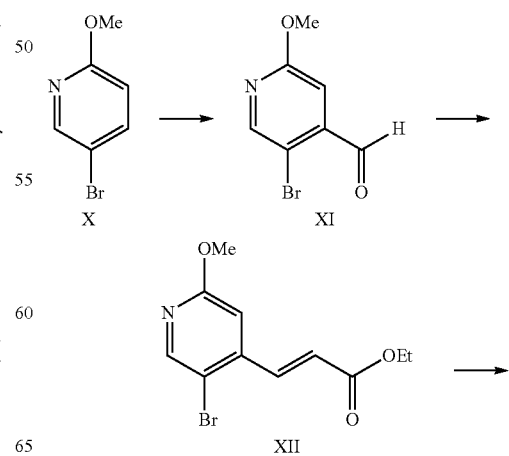

Scheme 2

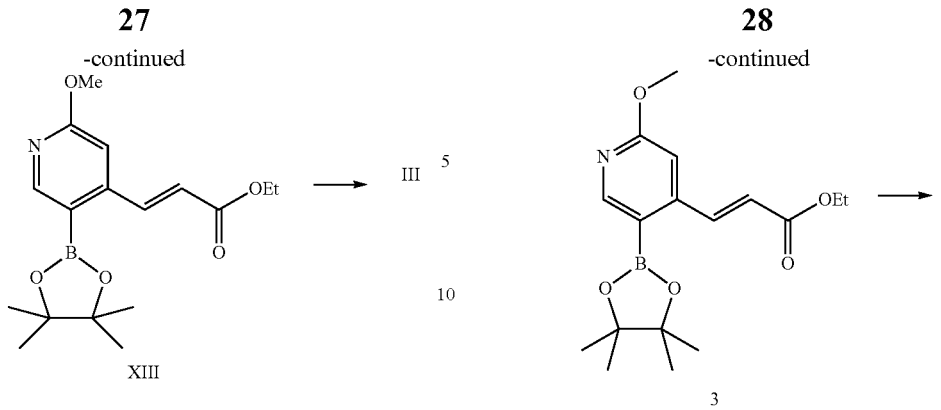

Compound X converted to XI by treating with base such as n-butyl lithium or the like and DMF or its equivalent. The compound XI was converted to compound XII under standard conditions either using malonic acid or witting reagent. Compound XII was treated with boron reagent in the presence of Pd catalyst and suitable ligand to form XIII. Reacting compound XIII with excess methyl iodide gave compound III (Scheme 2). Further compound III is converted to Formula I as described in Scheme 1.

The examples given below are provided by the way of illustration only and therefore should not be construed to limit the scope of the invention.

EXAMPLES

The following examples provide the details about the synthesis, activities, and applications of the compounds of the present disclosure. It should be understood the following is representative only, and that the invention is not limited by the details set forth in these examples.

Synthesis of Intermediate L1

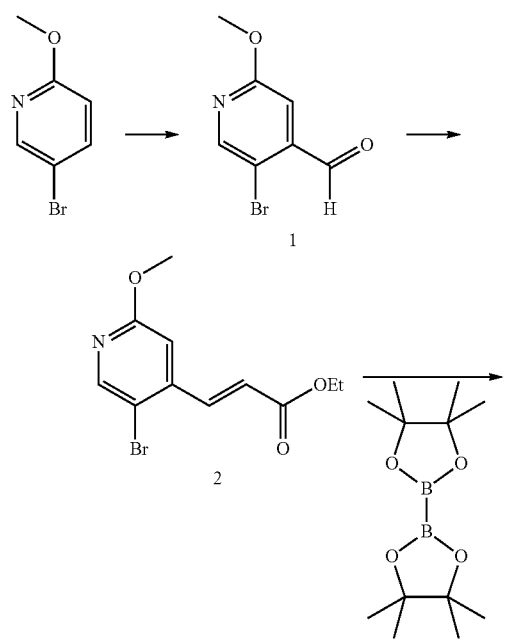

Preparation of 5-bromo-2-methoxyisonicotinaldehyde (1)

To a stirred solution of diisopropylamine (111.6 mL, 0.79 mol) in THF (200 mL) was cooled to −20° C. with dry ice acetone, slowly n-butyl lithium (192 mL, 0.32 mol, 1.6M) was added through cannula and stirred at same temperature for 30 minutes and the cooled to −78° C. 5-bromo-2-methoxypyridine (50 g, 0.27 mol) in THF (150 mL) was added through cannula for about 15 minutes and then stirred at same temperature. After 1 hr dry DMF (61.4 mL, 0.79 mol) was added and slowly warmed to room temperature and stirred. After 2 h the reaction mixture was quenched with sat. ammonium chloride. The organic layer was dried and concentrated to get solid. The solid was washed with cold hexane to obtain 5-bromo-2-methoxyisonicotinaldehyde (40 g, 69%) as a pale yellow color solid, $^1$H NMR (DMSO-$d_6$, 400 MHz) δ (ppm): 10.09 (s, 1H), 8.52 (s, 1H), 7.14 (s, 1H), 3.85 (s, 3H). MS (ESI): mass calcd. 216.2 for $C_7H_6BrNO_2$; m/z, found 218.03[M+H]$^+$.

Preparation of (E)-ethyl 3-(5-bromo-2-methoxypyridin-4-ul)acrylate (2)

To a stirred solution of methyl 5-bromo-2-methoxyisonicotinaldehyde (24 g, 0.11 mol) in dichloromethane (150 mL), cooled to 0° C. and ethyl 2-(triphenylphosphoranylidene) acetate (38.6 g, 0.11 mol) was dissolved in dichloromethane (150 mL) and added dropwise. After addition the reaction mixture was warmed to room temperature and stirred for 10 h and the reaction mixture was concentrated to get residue which was stirred with 5% ethyl acetate/hexane. The solid was filtered and the filtrate was concentrated to obtain (E)-ethyl 3-(5-bromo-2-methoxypyridin-4-yl) acrylate (23.6 g, 74%) as a white solid. (25 g, 95% yield), $^1$H NMR (DMSO-d$_6$, 400 MHz) δ (ppm): 8.40 (s, 1H), 7.68-7.64 (d, J=16 Hz, 1H), 6.90-6.87 (d, J =16 Hz, 1H), 4.25-4.19 (q, J=24 Hz, 2H), 3.84 (s, 3H), 1.28-1.24 (t, J=16 Hz, 3H). MS (ESI): mass calcd 286.3 for $C_{11}H_{12}BrNO_3$, m/z, found 288.16[M+2H]$^+$.

Preparation of (E)-ethyl 3-(2-methoxy-5-(4,4,5,5-tetramethyl-1,3,2-dioxaborolan-2-yl)pyridin-4-yl) acrylate (3)

To a stirring solution of (E)-methyl 3-(5-bromo-2-methoxypyridin-4-yl)acrylate (2, 28 g, 0.098 mol) in 1,4-dioxane (500 mL), bispinacolatodiboron (37.15 g, 0.146 mol), potassium acetate (19.18 g, 0.195 mol) were added and degassed with nitrogen for 15 min, tetrakis triphenylphosphine palladium (0) (3.4 g, 0.005 mol) was added and again degassed for 5 min. The resulting mixture was heated at 90° C. for 5 h. The reaction mixture was cooled to room temperature and filtered through celite bed. The filtrate was evaporated completely to get residue which was dissolved in 500 mL of ethyl acetate and washed with water (100 mL) and brine (100 mL). The organic layer was dried with anhydrous Na$_2$SO$_4$ and filtered. The filtrate was evaporated to get crude product. The crude product was purified by combiflash eluting (silica gel) with 0-100% ethyl acetate in hexane. The pure fractions containing required product concentrated to obtain (E)-ethyl 3-(2-methoxy-5-(4,4,5,5-tetramethyl-1,3,2-dioxaborolan-2-yl)pyridin-4-yl)acrylate (24.4 g, 75% yield). $^1$H NMR (DMSO-d$_6$, 400 MHz) δ (ppm): 8.57 (s, 1H), 8.37 (d, J=15, 6 Hz, 1H), 6.88 (s, 1H), 6.43-6.39 (d, J=16 Hz, 1H), 4.29-4.23 (q, J=7.6 Hz, 2H), 3.9 (s, 3H), 1.34-1.32 (t, J=6 Hz, 3H), 1.26 (s, 12H). MS (ESI): mass calcd 333.1 for $C_{17}H_{24}BNO_5$; m/z found, 334.2 [M+H]$^+$.

Preparation of (E)-ethyl 3-(1-methyl-2-oxo-5-(4,4,5,5-tetramethyl-1,3,2-dioxaborolan-2-yl)-1,2-dihydropyridin-4-yl)acrylate (L1)

To a stirring solution of (E)-ethyl 3-(2-methoxy-5-(4,4,5,5-tetramethyl-1,3,2-dioxaborolan-2-yl)pyridin-4-yl)acrylate (3, 20 g, 0.060 mol) in acetonitrile (14 mL) was added methyl iodide (8.52 mL, 0.14 mol) at 0° C. The resulting reaction mixture was heated at 90° C. in a sealed tube. After 12 h the reaction mixture was cooled to room temperature and evaporated off the solvent completely to get crude product. The crude was purified by combiflash eluting with 0-100% ethyl acetate in hexane. The pure fractions containing required product concentrated to obtain (E)-ethyl 3-(1-methyl-2-oxo-5-(4,4,5,5-tetramethyl-1,3,2-dioxaborolan-2-yl)-1,2-dihydropyridin-4-yl)acrylate as a (16 g, 80% yield) pale yellow solid. H NMR (DMSO-d$_6$, 400 MHz) δ (ppm): 8.17-8.12 (d, J=16 Hz, 1H), 7.79 (s, 1H), 6.72 (s, 1H), 6.342-6.36 (d, J=16 Hz, 1H), 4.27-4.22 (q, J=7.2 Hz, 2H), 3.55 (s, 3H), 1.34-1.31 (t, J=7.2 Hz, 3H), 1.31 (s, 12H). MS (ESI): mass calcd 333.1 for $C_{17}H_{24}BNO_5$; m/z found, 334.2 [M+H]$^+$.

Synthesis of Intermediate L2

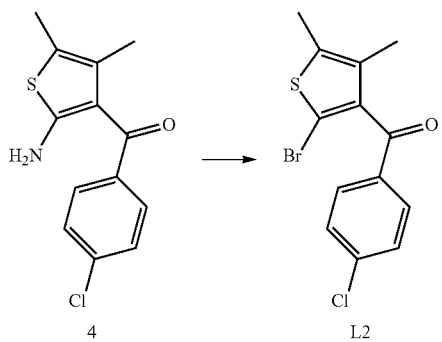 [SMILES: Cc1sc(N)c(C(=O)c2ccc(Cl)cc2)c1C ; Cc1sc(Br)c(C(=O)c2ccc(Cl)cc2)c1C]

Preparation of (2-bromo-4,5-dimethylthiophen-3-yl) (4-chlorophenyl)methanone (L2)

A solution of (2-amino-4,5-dimethylthiophen-3-yl)(4-chlorophenyl)methanone (4, 2 g, 7.55 mmol) in acetonitrile (50 mL) was taken and cooled to 0° C. and tert-butyl nitrite (0.86 g, 8.3 mmol) was added drop wise over 10 minutes. The solution was stirred for 20 minutes and then copper(II) bromide (2.52 g, 1.13 mmol) was added and stirred at the same temperature for 1 h. The mixture was warmed to room temperature and stirred for 2 h. The reaction mixture was diluted with dichloromethane (50 mL) and 2N hydrochloric acid. The organic layer was separated, dried with anhydrous Na$_2$SO$_4$, filtered and concentrated to give the crude product. The crude product was purified by combi-flash (silica gel) eluting with 0-10% ethyl acetate/hexane. The pure fractions were concentrated to obtain (2-bromo-4,5-dimethylthiophen-3-yl)(4-chlorophenyl)methanone as a pink color solid (0.55 g, 22%). $^1$HNMR: (400 MHz, DMSO-d$_6$) δ (ppm): 7.75 (d, J=8.4 Hz, 2H), 7.62 (d, J=8.4 Hz, 2H), 2.30 (s. 3H), 1.90 (s, 3H), MS (ESI): mass calcd 329.64 for $C_{13}H_{10}BrClOS$; m/z found, 331.28 [M+H]$^+$.

Synthesis of Intermediate L3

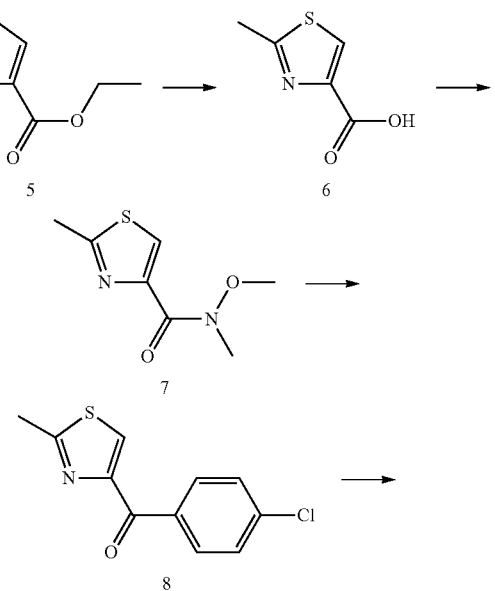

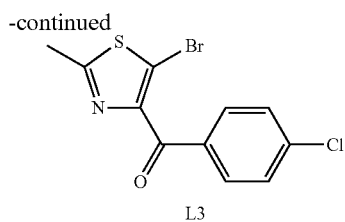

L3

Preparation of 2-methylthiazole-4-carboxylic acid (6)

To a stirred solution of ethyl 2-methylthiazole-4-carboxylate (5, 5.0 g, 29.23 mmol) in EtOH:H$_2$O (1:1, 20 mL) was added NaOH (3.58 g, 87.7 mmol) at 0-5° C. The mixture was stirred at room temperature for 16 h. Reaction mixture was concentrated to get solid residue. The residue was dissolved in water and acidified with 1N hydrochloric acid solution up to ~pH-5, pale pink solid obtained, filtered, dried under high vacuum (3.7 g, 88% yield). MS (ESI): mass calcd. for C$_5$H$_5$NO$_2$S, 143.16; m/z found, 144.1[M+H]$^+$.

Preparation of N-methoxy-N,2-dimethylthiazole-4-carboxamide (7)

To a stirred solution of 2-methylthiazole-4-carboxylic acid (6, 3.2 g, 22.35 mmol) in dichloromethane (50 mL), DIPEA (11.67 mL, 67.05 mmol), 1-[bis(dimethylamino)methylene]-1H-1,2,3-triazolo[4,5-b]pyridinium-3-oxohexafluorophosphate (HATU)(12.74 g, 33.52 mmol) at room temperature. The mixture was stirred for 10 minutes and N,O-dimethylhydroxylamine hydrochloride (4.36 g, 44.70 mmol) was added at 0° C. under nitrogen atmosphere. The mixture was stirred for 5 h at room temperature. The mixture was quenched with water. The residue was partitioned with dichloromethane and water. The organic layer was washed with cold water, dried over sodium sulphate, concentrated under reduced pressure. The crude product was purified by combiflash (Silica gel, 5-20% ethylacetate/hexane) to get the product as a colorless liquid. (2.6 g, 63% yield). MS (ESI): mass calcd. for C$_7$H$_{10}$N$_2$O$_2$S, 186.2; m/z, found 187.1[M+H]$^+$.

Preparation of (4-chlorophenyl)(2-methylthiazol-4-yl) methanone (8)

To the N-methoxy-N,2-dimethylthiazole-4-carboxamide (7, 2.6 g, 13.96 mmol) in dry diethylether (50 mL) under N$_2$ atmosphere at 0° C., 4-chlorophenylmagnesium bromide 1M solution in diethyl ether (18.14 mL, 18.14 mmol) was added dropwise. The reaction mixture was left stirring for 16 h at room temperature. The mixture was quenched with saturated ammonium chloride solution and diluted with ethyl acetate. The reaction mixture was filtered through celite bed. Organic layer was separated and washed with brine, dried over sodium sulphate, concentrated under reduced pressure. The crude product was purified by combiflash (silica gel, 5-60% ethylacetate/hexane) to yield as pale yellow solid (0.67 g, 20% yield). MS (ESI): mass calcd for C$_{11}$H$_8$ClNOS, 237.71; m/z, found: 238 [M+H]$^+$.

Preparation of (5-bromo-2-methylthiazol-4-yl)(4-chlorophenyl) methanone (L3)

To the (4-chlorophenyl)(2-methylthiazol-4-yl)methanone (8, 0.7 g, 2.94 mmol) in acetonitrile (10 mL) was added N-bromosuccinimide (1.82 g, 10.29 mmol) at room temperature. The reaction mixture was stirred at 80° C. for 12 h. The mixture was quenched with water. The residue was partitioned between ethyl acetate and water. The organic layer was washed with brine, dried over sodium sulphate, concentrated under reduced pressure. The crude product was purified by combiflash (silica gel, 5-20% ethylacetate/hexane) to get the product as a brown solid. (0.29 g, 31.5% yield). MS (ESI): mass calcd. for C$_{11}$H$_7$BrClNOS, 316.61; m/z found, 315.19 [M-1]$^-$.

Synthesis of Intermediate L4

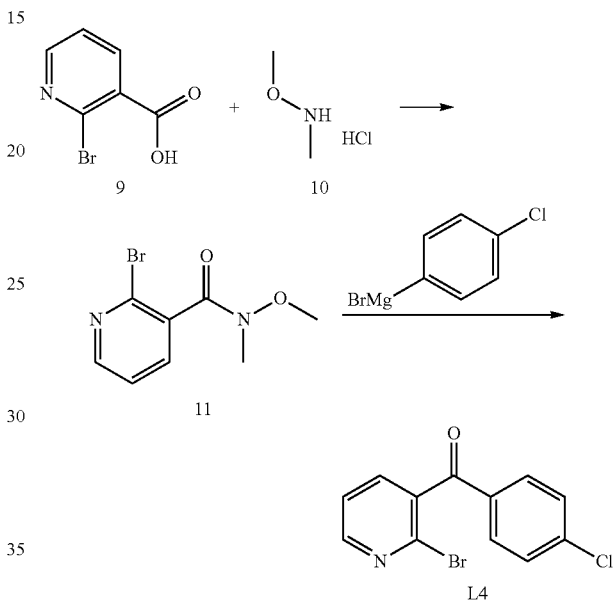

Preparation of 2-bromo-N-methoxy-N-methylnicotinamide (11)

To a stirred solution of 2-bromonicotinic acid (9, 5.0 g, 20.3 mmol) in dry dichloromethane (150 mL) was added DIPEA (8.6 mL, 49.5 mmol), N-[(dimethylamino)-1H-1,2,3-triazolo-[4,5-b]pyridin-1-ylmethylene]-N-ethyl methanaminium hexafluorophosphate N-oxide (HATU) (12.2 g, 32.1 mmol) and N,O-dimethylhydroxylamine hydrochloride (10, 3.14 g, 32.1 mmol) was added at 0° C. under N$_2$ atmosphere. The reaction mixture was stirred for 16 h at room temperature. The mixture was quenched with water and extracted with dichloromethane, dried over anhydrous sodium sulphate, concentrated under reduced pressure.

The crude product was purified by combiflash (silica gel, 15-25% ethylacetate/hexane) to get the product as a white solid (5.1 g, 83.0% yield). MS (ESI): mass calcd for C$_{10}$H$_{11}$BrNO$_3$, 245.11; m/z, found: 246.9 [M+H]$^+$.

Preparation of (2-bromopyridin-3-yl)(4-chlorophenyl)methanone (L4)

To a stirred solution of 2-bromo-N-methoxy-N-methylnicotinamide (11, 5.0 g, 20.3 mmol) in dry THF (100 mL) under N$_2$ atmosphere at 0° C., 4-chlorophenylmagnesium bromide 1.0 M solution in diethyl ether (23 mL, 22.4 mmol) was added drop wise. The reaction mixture was stirred for 3

Synthesis of Intermediate L5

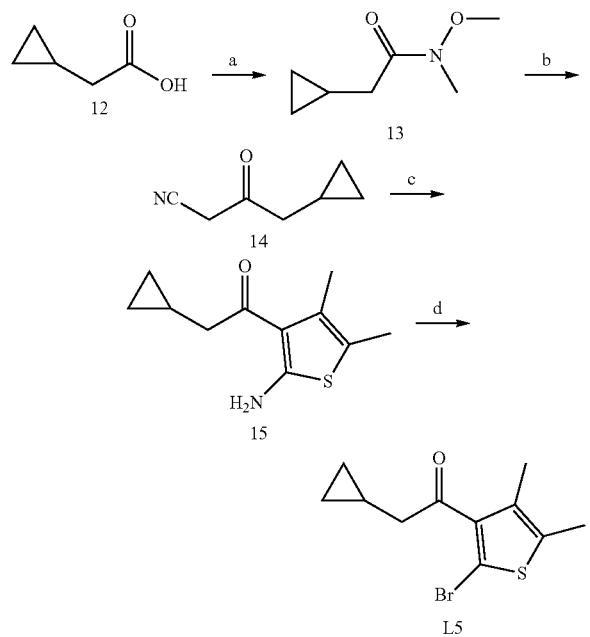

Preparation of
2-cyclopropyl-N-methoxy-N-methylacetamide (13)

HATU (5 g, 15.0 mmol) was added to a solution of 2-cyclopropylacetic acid (12, 1.0 g, 10.0 mmol) in DMF (5 mL) and stirred for 5 min, then diisopropylamine (11.5 mL, 70.0 mmol) was added followed by addition of N,O-dimethylhydroxylamine hydrochloride (4.87 g, 50.0 mmol). After 1 h the reaction mixture was diluted with ethylacetate and washed with water and brine solution. The organic layer was dried over anhydrous sodium sulphate and concentrated to give crude product. The crude product was purified by combi-flash (silica gel) eluting with 0-15% ethyl acetate in hexane. The pure fractions were concentrated to afford 2-cyclopropyl-N-methoxy-N-methylacetamide (1.2 g, 85% yield) as a white solid. $^1$HNMR: (400 MHz, DMSO-$d_6$) δ (ppm): 3.60 (s, 3H), 3.05 (s, 3H), 2.26 (d, J=8 Hz, 2H), 0.93-0.91 (m, 1H), 0.42-0.40 (m, 2H), 0.09-0.07 (m, 2H). MS (ESI): mass calcd for $C_7H_{13}NO_2$, 143.09; m/z found, 144.1 [M+H].

Preparation of 4-cyclopropyl-3-oxobutanenitrile (14)

n-Butyl lithium (33 mL, 52.0 mmol) was added to a solution of acetonitrile (3.4 mL, 66.0 mmol) in THF (30 mL) at −78° C. and stirred for 45 minutes. Then 2-cyclopropyl-N-methoxy-N-methylacetamide (13, 6.3 g, 44.0 mmol) was dissolved in THF (5 mL) and added slowly and stirred at −78° C. After 1 h the mixture was slowly warmed to 25° C. and stirred. After 2 h the reaction mixture was quenched with sat ammonium chloride solution. The organic layer was separated and dried with anhydrous $Na_2SO_4$, filtered and concentrated to get residue. The crude product was purified by combi-flash (silica gel) eluting with 0-20% ethyl acetate/hexane. The pure fractions were concentrated to afford 4-cyclopropyl-3-oxobutanenitrile (5.5 g, 98%, yield) white solid. $^1$HNMR: (400 MHz, $CDCl_3$) δ (ppm): 3.51 (s, 2H), 2.48 (d, J=8 Hz, 2H), 1.03-0.97 (m, 1H), 0.66-0.61 (m, 2H), 0.20-0.15 (m, 2H). MS (ESI): mass calcd for $C_7H_9NO$, 123.07; m/z, found: 124.1 [M+H].

Preparation of 1-(2-amino-4,5-dimethylthiophen-3-yl)-2-cyclopropylethan-1-one (15)

Sulfur (1.4 g, 6.9 mmol) was added as a solid to a solution of 4-cyclopropyl-3-oxobutanenitrile (14, 5.5 g, 44.7 mmol), 2-butanone (3.2 g, 44.7 mmol) and morpholine (3.8 mL, 44.7 mmol) in ethanol (150 mL) at 25° C. The mixture was then heated to 70° C. After 12 hours, the reaction mixture was cooled to 25° C. and poured into brine (100 mL). The aqueous layer was extracted with ethyl acetate (3×100 mL). The combined organic layers was washed with brine (150 mL), dried over anhydrous sodium sulphate, filtered, and was concentrated under reduced pressure. The crude product was purified by combi-flash (silica gel) eluting with 0-20% ethyl acetate/hexane. The pure fractions were concentrated to afford 1-(2-amino-4,5-dimethylthiophen-3-yl)-2-cyclopropylethan-1-one (6.3 g, 67% yield) yellow colored solid. $^1$HNMR: (400 MHz, DMSO-$d_6$) δ (ppm): 8.03 (bs, 2H), 2.59 (d, J=8 Hz, 2H), 2.10 (s, 3H) 2.05 (s, 3H), 1.01-0.98 (m, 1H), 0.44-0.39 (m, 2H), 0.09-0.05 (m, 2H). MS (ESI): mass calcd for $C_{11}H_{15}NOS$, 209.13; m/z, found: 210.1 [M+H].

Preparation of 1-(2-bromo-4,5-dimethylthiophen-3-yl)-2-cyclopropylethan-1-one (L5)

A solution of 1-(2-amino-4,5-dimethylthiophen-3-yl)-2-cyclopropylethan-1-one (15, 1.3 g, 6.22 mmol) in acetonitrile (30 mL) was taken and cooled to 0° C. and tert-butyl nitrite (0.83 g, 8.08 mmol) was added drop wise for 10 minutes. The solution was stirred for 20 minutes and then copper (II) bromide (2.08 g, 9.33 mmol) was added and stirred at same temperature for 1 h. After 1 h the mixture was warmed to room temperature and stirred for 2 h. Then the reaction mixture was diluted with DCM (50 mL) and 2N HCl. The organic layer was separated, dried with anhydrous $Na_2SO_4$, filtered and concentrated to get the crude product. The crude product was purified by combi-flash eluting with 0-10% ethyl acetate/hexane. The pure fractions were concentrated to obtain 1-(2-bromo-4,5-dimethylthiophen-3-yl)-2-cyclopropylethan-1-one (0.81 g, 47%, yield) as a orange color solid. $^1$HNMR: (400 MHz, DMSO-$d_6$) δ (ppm): 2.74 (d, J=8 Hz, 2H), 2.24 (s, 3H), 2.04 (s, 3H), 1.01-0.98 (m, 1H), 0.48-0.44 (m, 2H), 0.13-0.09 (m, 2H). MS (ESI): mass calcd for $C_{11}H_{13}BrOS$, 273.19; m/z found, 275.1 [M+2].

Synthesis of (4-chlorophenyl)(1-methyl-4-(4,4,5,5-tetramethyl-1,3,2-dioxaborolan-2-yl)-1H-pyrazol-5-yl)methanone-L6

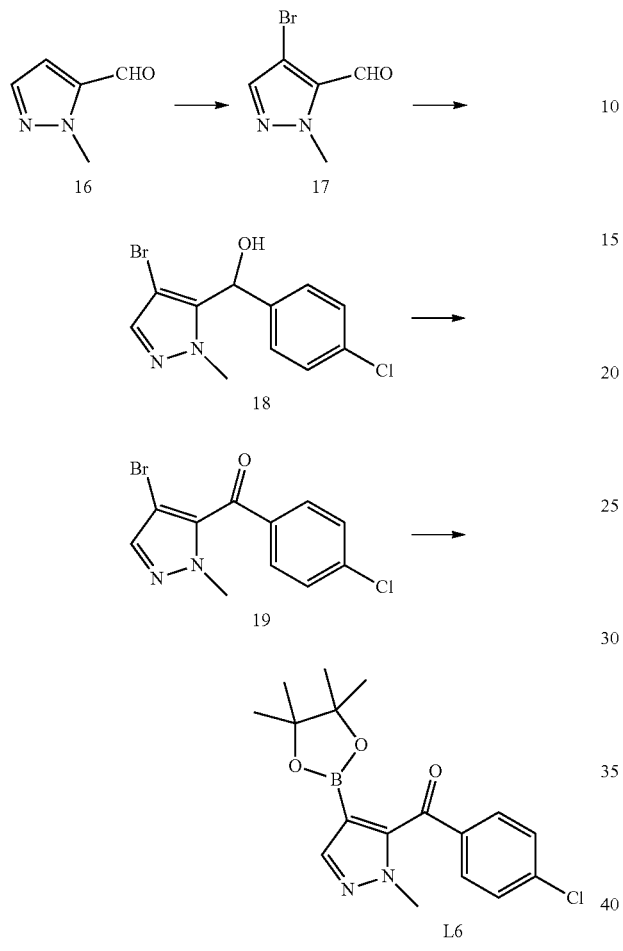

Preparation of 4-bromo-1-methyl-1H-pyrazole-5-carbaldehyde (17)

To a stirred solution 1-methyl-1H-pyrazole-5-carbaldehyde (5.00 g, 0.045 mol) in DMF (40 mL) was added NBS (8.1 g, 0.045 mol) of DMF solution slowly over a period of 10 min at 0° C. Reaction mixture was left for stirring overnight at room temperature. After completion of reaction, confirmed from TLC, crushed ice was added and extracted with ethyl acetate. The organic layer was washed with brine, dried over anhydrous sodium sulphate, Organic part was concentrated. Purification was done by combiflash (silica gel:ethyl acetate/hexane), desired compound was eluted in pure hexane. The column fractions containing required spot were collected and evaporated to get 4-bromo-1-methyl-1H-pyrazole-5-carbaldehyde with 99.58% purity. (6.5 g; 76% yield). MS (ESI): mass calcd. For C5H5BrN2O, 187.96; m/z found, 189.0[M+H]+.

Preparation of (4-bromo-1-methyl-1H-pyrazol-5-yl)(4-chlorophenyl)methanol (18)

To a stirred solution 4-bromo-1-methyl-1H-pyrazole-5-carbaldehyde (6.00 g, 0.032 mol) in THF (40 mL) was added 1.0 (M) solution of (4-chlorophenyl) magnesium bromide in diethyl ether (1.3 mL, 0.0415 mol) slowly over a period of 10 min at 0° C. Reaction mixture was left for stirring 30 min at 0° C. followed by 1 h stirring at rt. After completion of reaction, confirmed from TLC, crushed ice was added and extracted with ethyl acetate. The organic layer was washed with brine, dried over anhydrous sodium sulphate, Organic part was concentrated. Purification was done by n-pentane washing to get (4-bromo-1-methyl-1H-pyrazol-5-yl)(4-chlorophenyl)methanol with 70% purity. (10.0 g; quantitative). MS (ESI): mass calcd. For $C_{11}H_{10}BrClN_2O$, 299.97; m/z found, 311.0[M+H]$^{2+}$.

Preparation of (4-bromo-1-methyl-1H-pyrazol-5-yl)(4-chlorophenyl) Methanone (19)

To a stirred solution of (4-bromo-1-methyl-1H-pyrazol-5-yl)(4-chlorophenyl)methanol (10.0 g, 0.033 mol) in DCM (40 mL) was added pyridinium chlorochromate (10.0 g, 0.0462 mol) and left for stirring 1 h at rt. After completion of reaction, confirmed from TLC, sat. NaHCO3 solution was added and extracted with DCM. The organic layer was washed with brine, dried over anhydrous sodium sulphate, Organic part was concentrated. Purification was done by combiflash (silica gel:ethyl acetate/hexane), desire compound was eluted in 4% EA/hexane. The column fractions containing required spot were collected and evaporated to get (4-bromo-1-methyl-1H-pyrazol-5-yl)(4-chlorophenyl)methanone with 98.85% purity. (7.0 g; 70% yield). MS (ESI): mass calcd. For C11H8BrClN2O 297.95; m/z found, 299.0[M+H]+.

Preparation of (4-chlorophenyl)(1-methyl-4-(4,4,5,5-tetramethyl-1,3,2-dioxaborolan-2-yl)-1H-pyrazol-5-yl)methanone (L6)

To a stirred solution of (4-bromo-1-methyl-1H-pyrazol-5-yl)(4-chlorophenyl)methanone (10.0 g, 0.035 mol) in 1,4 Dioxane (100 mL) was added bis(pinacolato)diborane (15.18 g, 0.04385 mol) and potassium acetate (23.58 g, 0.28 mol) and de-gassing was done for 20 min. Then [1,1'-bis(diphenylphosphino)ferrocene]dichloropalladium(II) catalyst (2.4 g, 0.0070 mol) was added and further de-gassing was done. Reaction mixture was refluxed for 4 h. After completion of reaction, confirmed from TLC, filtration was done and reaction mixture was concentrated. Residue was dissolved in EA, washed with water, brine, dried over anhydrous sodium sulphate, Organic part was concentrated. Purification was done by combiflash (silica gel:ethyl acetate/hexane), desire compound was eluted in 60% EA/hexane. The column fractions containing required spot were collected and evaporated to get (4-chlorophenyl) (1-methyl-4-(4,4,5,5-tetramethyl-1,3,2-dioxaborolan-2-yl)-1H-pyrazol-5-yl)methanone with 81.45% purity. (4.5 g; 38% yield). MS (ESI): mass calcd. For C17H20BClN2O3, 346.13; m/z found, 347.1[M+H]+.

Example 1: ±Ethyl 2-(4-(4-chlorophenyl)-2,3,9-trimethyl-8-oxo-8,9-dihydro-6H-pyrido[4,3-c]thieno[2,3-e]azepin-6-yl)acetate

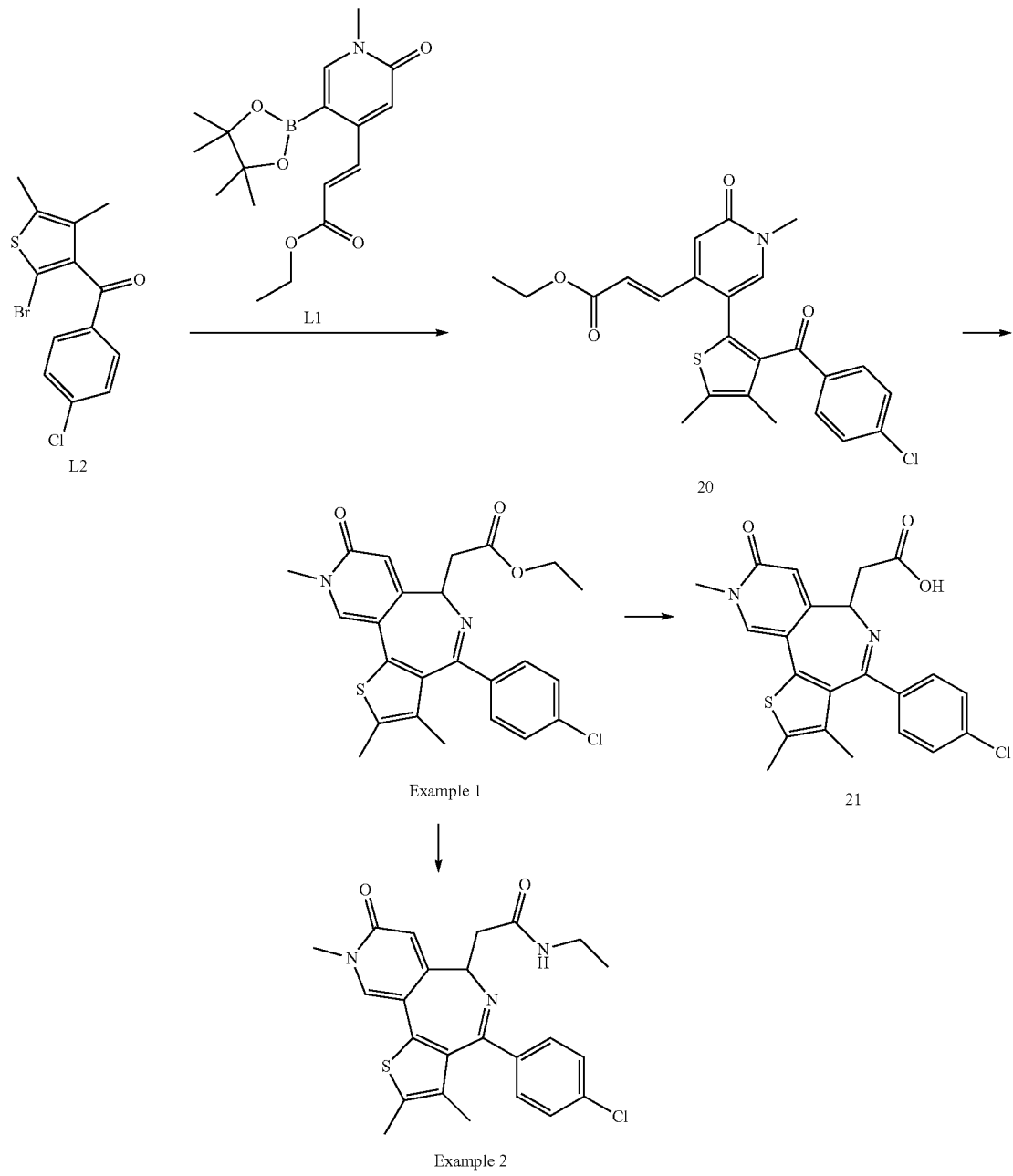

Preparation of (E)-ethyl 3-(5-(3-(4-chlorobenzoyl)-4,5-dimethylthiophen-2-yl)-1-methyl-2-oxo-1,2-dihydropyridin-4-yl)acrylate (20)

A mixture of (2-bromo-4,5-dimethylthiophen-3-yl)(4-chlorophenyl)methanone (Intermediate L2, 0.5 g, 1.5 mmol), (E)-ethyl 3-(1-methyl-2-oxo-5-(4,4,5,5-tetramethyl-1,3,2-dioxaborolan-2-yl)-1,2-dihydropyridin-4-yl)acrylate (Intermediate L1, 0.61 g, 1.80 mmol) and 2M aqueous sodium bicarbonate (0.25 g, 3.00 mmol) were taken in toluene (20 mL). The mixture was purged with nitrogen gas for 10 minutes. Then tetrakis(triphenylphosphine)palladium (0) (0.173 g, 0.15 mmol) was added and again nitrogen gas was purged for 5 minutes and the mixture was heated at 105° C. for 15 h. The reaction mixture was cooled to room temperature, diluted with water (100 mL) and extracted with ethyl acetate (100 mL). Organic layers were combined, washed with brine, dried over anhydrous sodium sulphate and concentrated to get the crude product. The crude product was purified by combi-flash eluting with 0-10% methanol in dichloromethane. The pure fractions were concentrated to obtain (E)-ethyl 3-(5-(3-(4-chlorobenzoyl)-4,5-dimethylthiophen-2-yl)-1-methyl-2-oxo-1,2-dihydropyridin-4-yl)acrylate (0.45 g, 65.2%) as a pale pink colored gum. $^1$HNMR: (400 MHz, DMSO-d$_6$) δ (ppm): 7.684 (s, 1H), 7.53 (d, J=12 Hz, d), 7.41 (d, J=12 Hz, 2H), 7.11 (d, J=16 Hz, 1H) 6.57 (s, 1H), 6.39 (d, J=16 Hz, 1H), 4.10 (q, J=8 Hz, 2H), 3.32 (s, 3H), 2.39 (s, 3H), 1.99 (s, 3H), 0.83 (t, J=8 Hz, 3H). MS (ESI): mass calcd for $C_{24}H_{22}ClNO_4S$, 455.10; m/z, found: 456.0, [M+H]⁻.

Preparation of ±Ethyl 2-(4-(4-chlorophenyl)-2,3,9-trimethyl-8-oxo-8,9-dihydro-6H-pyrido[4,3-c]thieno[2,3-e]azepin-6-yl)acetate A solution of (E)-ethyl 3-(5-(3-(4-chlorobenzoyl)-4,5-dimethylthiophen-2-yl)-1-methyl-2-oxo-1,2-dihydropyridin-4-yl)acrylate (20, 0.63 g, 0.14 mmol) in ethanol (12 mL), ammonium formate (1.7 g, 27.0 mmol) was added and heated to 90° C. After 24 h the reaction mixture was cooled to room temperature and diluted with ethyl acetate and washed with water and brine. The organic layer was dried over anhydrous sodium sulphate and concentrated to give a residue. The crude was purified by combi-flash eluting with 0-10% methanol in dichloromethane. The pure fractions were concentrated to afford the product (0.47 g. 74%) as a pale yellow colored solid. ¹HNMR: (400 MHz, DMSO-d₆) δ (ppm): 8.05 (s, 1H), 7.44 (d, J=8.4 Hz, 2H) 7.29 (d, J=8.4 Hz, 2H) 6.39 (d, J=16 Hz, 1H) 4.25-4.21 (m, 1H), 4.15 (q, J=4 Hz, 2H), 3.46 (s, 3H), 3.26 (d, J=8 Hz, 1H) 3.16 (d, J=8 Hz, 1H), 2.36 (s, 3H), 1.59 (s, 3H), 0.85 (t, J=8 Hz, 3H), MS (ESI): mass calcd for $C_{24}H_{23}ClN_2O_3S$, 454.11; m/z, found: 455.1 [M+H]⁻.

Preparation of 2-(4-(4-chlorophenyl)-2,3,9-trimethyl-8-oxo-8,9-dihydro-6H-pyrido[4,3-c]thieno[2,3-e]azepin-6-yl)acetic acid (21)

4N solution of sodium hydroxide (3.62 g, 90.6 mmol) was added to a solution of ethyl 2-(4-(4-chlorophenyl)-2,3,9-trimethyl-8-oxo-8,9-dihydro-6H-pyrido[4,3-c]thieno[2,3-e]azepin-6-yl)acetate (Example a, 2.07 g, 4.5 mmol) in methanol (30 mL) and solution was stirred at room temperature. After 5 h the mixture was concentrated to remove volatiles to get residue which was taken in water and acidified with 2N HCl to obtain a solid. The solid was filtered and dried to obtain 2-(4-(4-chlorophenyl)-2,3,9-trimethyl-8-oxo-8,9-dihydro-6H-pyrido[4,3-c]thieno[2,3-e]azepin-6-yl)acetic acid (1.65 g, 85%, yield) as a pale yellow colored solid. ¹H NMR: (400 MHz, DMSO) δ (ppm): 12.29 (s, 1H), 8.04 (s, 1H), 7.44 (d, J=8.0 Hz, 2H), 7.16 (d, J=8.0 Hz, 2H), 6.37 (s, 1H), 4.24 (t, J=8 Hz, 1H), 3.45 (s, 3H), 3.11-3.15 (m, 2H), 2.36 (s, 3H), 1.59 (s, 3H). MS (ESI): mass calcd. For $C_{22}H_{19}ClN_2O_3S$, 426.08; m/z, found: 427.2 [M+H].

Example 2: ±2-(4-(4-chlorophenyl)-2,3,9-trimethyl-8-oxo-8,9-dihydro-6H-pyrido[4,3-c]thieno[2,3-e]azepin-6-yl)-N-ethylacetamide

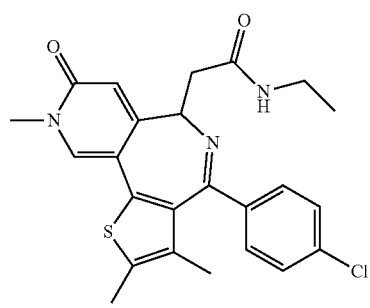 [SMILES: CCNC(=O)CC1N=C(c2ccc(Cl)cc2)c2c(sc(C)c2C)-c2cn(C)c(=O)cc21]

A solution of ethyl 2-(4-(4-chlorophenyl)-2,3,9-trimethyl-8-oxo-8,9-dihydro-6H-pyrido[4,3-c]thieno[2,3-e]azepin-6-yl)acetate (Example 1, 0.4 g, 0.88 mmol) ethylamine (2.1 mL, 2M solution in THF), cooled to 0° C. and trimethylaluminium (2.1 mL, 2M solution in THF) was added. After 30 min the mixture was warmed to room temperature and then heated at 80° C. After 1 h the reaction mixture was cooled to room temperature and mixture was quenched with sat ammonium chloride solution and extracted with ethyl acetate. The organic layer was dried over anhydrous sodium sulphate and concentrated to give the crude product. The crude product was purified by combi-flash eluting with 0-10% methanol in dichloromethane. The pure fractions were concentrated to afford 2-(4-(4-chlorophenyl)-2,3,9-trimethyl-8-oxo-8,9-dihydro-6H-pyrido[4,3-c]thieno[2,3-e]azepin-6-yl)-N-ethylacetamide (0.14 g, 35%) as a pale yellow color solid, ¹HNMR: (400 MHz, DMSO-d₆) δ (ppm): 8.12 (bs, 1H), 8.02 (s, 1H), 7.43 (d, J=8 Hz, 2H), 7.32 (d, J=8 Hz, 2H), 6.41 (s, 1H), 4.26 (t, J=8 Hz, 1H), 3.45 (s, 3H), 3.10-3.04 (m, 2H), 2.96-2.94 (m, 2H), 2.36 (s, 3H), 1.59 (s, 3H), 1.01 (t, J=8 Hz, 3H). MS (ESI): mass calcd for $C_{24}H_{24}ClN_3O_2S$, 453.13; m/z, found: 454.2[M+H].

Preparative Chiral HPLC Method for the Separation of Enantiomers 2a and 2b

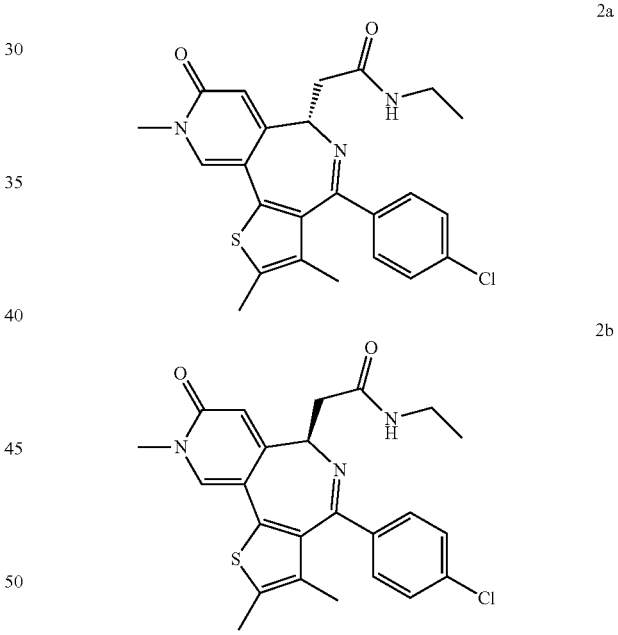

Preparative Chiral HPLC Method for the Separation of Enantiomers

Column: CHIRALPAK IA (250 mm×4.6 mm×5im)
Wavelength monitored 225 nm
Mobile phase: 100% MEOH

Example 2a: (S)-2-(4-(4-chlorophenyl)-2,3,9-trimethyl-8-oxo-8,9-dihydro-6H-pyrido[4,3-c]thieno[2,3-e]azepin-6-yl)-N-ethylacetamide ¹HNMR: (400 MHz, DMSO-d₆) δ (ppm): 8.12 (bs, 1H), 8.02 (s, 1H), 7.43 (d, J=8 Hz, 2H), 7.32 (d, J=8 Hz, 2H) 6.41 (s, 1H) 4.26 (t, J=8 Hz, 1H) 3.45 (s, 3H) 3.10-3.04 (m, 2H)

2.96-2.94 (m, 2H) 2.36 (s, 3H) 1.59 (s, 3H) 1.01 (t, J=8 Hz, 3H). MS (ESI): mass calcd for $C_{24}H_{24}ClN_3O_2S$, 453.13; m/z, found: 454.2[M+H]+.

Example 2b: (R)-2-(4-(4-chlorophenyl)-2,3,9-trimethyl-8-oxo-8,9-dihydro-6H-pyrido[4,3-c]thieno[2,3-e]azepin-6-yl)-N-ethylacetamide $^1$HNMR: (400 MHz, DMSO-$d_6$) δ (ppm): 8.12 (bs, 1H), 8.02 (s, 1H), 7.43 (d, J=8 Hz, 2H) 7.32 (d, J=8 Hz, 2H) 6.41 (s, 1H) 4.26 (t, J=8 Hz, 1H) 3.45 (s, 3H) 3.10-3.04 (m, 2H) 2.96-2.94 (m, 2H) 2.36 (s, 3H) 1.59 (s, 3H) 1.01 (t, J=8 Hz, 3H). MS (ESI): mass calcd for $C_{24}H_{24}ClN_3O_2S$, 453.13; m/z, found: 454.2[M+H]+.

Example 3: ±2-(4-(4-chlorophenyl)-2,3,9-trimethyl-8-oxo-8,9-dihydro-6H-pyrido[4,3-c]thieno[2,3-e]azepin-6-yl)acetamide

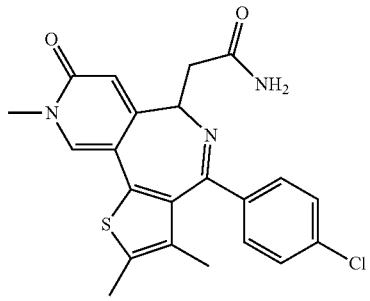

HATU (0.26 g, 0.699 mmol) was added to a solution of 2-(4-(4-chlorophenyl)-2,3,9-trimethyl-8-oxo-4,6,8,9-tetrahydrothieno[2',3':5,6]oxepino[4,3-c]pyridin-6-yl)acetic acid (21, 0.2 g, 0.47 mmol) in DMF (5 mL) and stirred for 5 minutes, then liquor ammonia (7 mL) was added. After 1 h the reaction mixture was diluted with ethyl acetate and washed with water and brine solution. The organic layer was dried over anhydrous sodium sulphate and concentrated to give residue. The crude product was purified by combi-flash eluting with 0-10% MeOH/DCM. The pure fractions were concentrated to afford 2-(4-(4-chlorophenyl)-2,3,9-trimethyl-8-oxo-4,6,8,9-tetrahydrothieno[2',3':5,6]oxepino[4,3-c]pyridin-6-yl)acetamide (145 mg, 56%, yield) as an off-white solid. $^1$H NMR (DMSO-$d_6$, 400 MHz) δ (ppm): 8.02 (s, 1H), 7.59 (s, 1H), 7.43 (d, J=8 Hz, 2H) 7.33 (d, J=8.0 Hz, 2H) 6.89 (s, 1H) 6.41 (s, 1H) 4.26 (t, J=4 Hz, 1H) 3.45 (s, 3H) 3.01-2.91 (m, 2H) 2.36 (s, 3H) 1.59 (s, 3H). MS (ESI): mass calcd. For $C_{22}H_{20}ClN_3O_2S$, 428.10; m/z found, 429.1 [M+1].

Preparative Chiral HPLC Method for the Separation of Enantiomers 3a and 3b

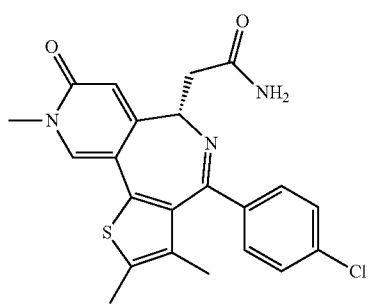 [SMILES: Cc1sc2c(c1C)C(c1ccc(Cl)cc1)=NC(CC(N)=O)c1cc(=O)n(C)cc1-2]

3a

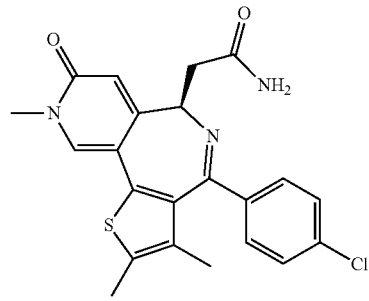

3b

Column: CHIRALPAK IA (250 mm×4.6 mm×5 m)
Wavelength monitored 265 nm
Mobile phase: 0.1% DEA in 100% MEOH Example 3a: (S)-2-(4-(4-chlorophenyl)-2,3,9-trimethyl-8-oxo-8,9-dihydro-6H-pyrido[4,3-c]thieno[2,3-e]azepin-6-yl)acetamide $^1$H NMR (DMSO-$d_6$, 400 MHz) δ (ppm): 8.02 (s, 1H), 7.59 (s, 1H), 7.43 (d, J=8 Hz, 2H), 7.33 (d, J=8.0 Hz, 2H), 6.89 (s, 1H), 6.41 (s, 1H), 4.26 (t, J=4 Hz, 1H), 3.45 (s, 3H), 3.01-2.91 (m, 2H), 2.36 (s, 3H), 1.59 (s, 3H). MS (ESI): mass calcd. For C22H20ClN3O2S, 428.10; m/z found, 429.1 [M+1].

Example 3b: (R)-2-(4-(4-chlorophenyl)-2,3,9-trimethyl-8-oxo-8,9-dihydro-6H-pyrido[4,3-c]thieno[2,3-e]azepin-6-yl)acetamide $^1$H NMR (DMSO-$d_6$, 400 MHz) δ (ppm): 8.02 (s, 1H), 7.59 (s, 1H), 7.43 (d, J=8 Hz, 2H), 7.33 (d, J=8.0 Hz, 2H), 6.89 (s, 1H), 6.41 (s, 1H), 4.26 (t, J=4 Hz, 1H), 3.45 (s, 3H), 3.01-2.91 (m, 2H), 2.36 (s, 3H), 1.59 (s, 3H). MS (ESI): mass calcd. For C22H20ClN3O2S, 428.10; m/z found, 429.1 [M+1].

Example 4: ±2-(4-(4-chlorophenyl)-2,3,9-trimethyl-8-oxo-8,9-dihydro-6H-pyrido[4,3-c]thieno[2,3-e]azepin-6-yl)-N-(4-hydroxyphenyl)acetamide

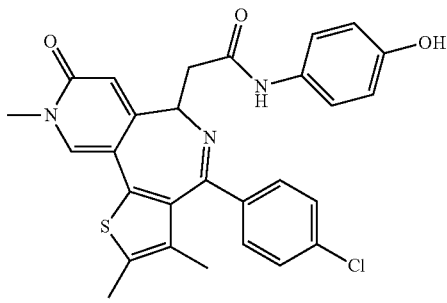 [SMILES: Cc1sc2c(c1C)C(c1ccc(Cl)cc1)=NC(CC(=O)Nc1ccc(O)cc1)c1cc(=O)n(C)cc1-2]

A solution of ethyl 2-(4-(4-chlorophenyl)-2,3,9-trimethyl-8-oxo-8,9-dihydro-6H-pyrido[4,3-c]thieno[2,3-e]azepin-6-yl)acetate (Example 1, 0.35 g, 0.76 mmol) and 4-aminophenol (0.41 g, 0.76 mmol) were taken in THF (3 mL), cooled to 0° C. and trimethylaluminium (1.81 mL, 2M solution in THF) was added. After 30 minutes the mixture was warmed to room temperature and then heated at 80° C. After 1 h the reaction mixture was cooled to room temperature and mixture was quenched with saturated ammonium chloride solution and extracted with ethyl acetate. The organic layer was dried over anhydrous sodium sulphate and concentrated to give the crude product. The crude product was purified by combi-flash eluting with 0-10% methanol in dichloromethane. The pure fractions were concentrated to afford 2-(4-(4-chlorophenyl)-2,3,9-trimethyl-8-oxo-8,9-dihydro-6H-pyrido[4,3-c]thieno[2,3-e]azepin-6-yl)-N-(4-hydroxyphenyl)acetamide (0.161 g, 41%) as a pale yellow color solid, $^1$HNMR: (400 MHz, DMSO-$d_6$) δ (ppm): 9.94 (s, 1H), 9.12 (s, 1H), 8.04 (bs, 1H), 7.42 (d, J =8 Hz, 2H), 7.34-7.30 (m, 4H), 6.66 (d, J=8.4 Hz, 2H), 6.47 (s, 1H), 4.34 (t, J=4 Hz, 1H), 3.45 (s, 3H), 3.18-3.16 (m, 2H), 2.36 (s, 3H) 1.59 (s, 3H). MS (ESI): mass calcd for $C_{28}H_{24}ClN_3O_3S$, 517.2; m/z, found: 518.1 [M+H]$^+$.

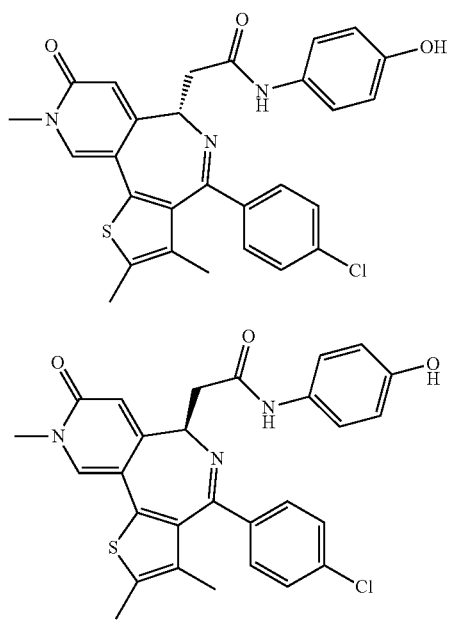

4a

4b

Preparative Chiral HPLC Method for the Separation of Enantiomers of Example 4

CHIRALPAK IA (250 mm×4.6 mm×5 m)
Wavelength monitored 254 nm
Mobile phase: 0.1% DEA in 100% MEOH Example 4a: (S)-2-(4-(4-chlorophenyl)-2,3,9-trimethyl-8-oxo-8,9-dihydro-6H-pyrido[4,3-c]thieno[2,3-e]azepin-6-yl)-N-(4-hydroxyphenyl)acetamide 1HNMR: (400 MHz, DMSO-$d_6$) δ (ppm): 9.94 (s, 1H), 9.12 (s, 1H), 8.04 (bs, 1H), 7.42 (d, J=8 Hz, 2H), 7.34-7.30 (m, 4H), 6.66 (d, J=8.4 Hz, 2H), 6.47 (s, 1H), 4.34 (t, J=4 Hz, 1H), 3.45 (s, 3H), 3.18-3.16 (m, 2H), 2.36 (s, 3H) 1.59 (s, 3H). MS (ESI): mass calcd for $C_{28}H_{24}ClN_3O_3S$, 517.2; m/z, found: 518.1 [M+H]$^+$.

Example 4b: (R)-2-(4-(4-chlorophenyl)-2,3,9-trimethyl-8-oxo-8,9-dihydro-6H-pyrido[4,3-c]thieno[2,3-e]azepin-6-yl)-N-(4-hydroxyphenyl)acetamide 1HNMR: (400 MHz, DMSO-$d_6$) δ (ppm): 9.94 (s, 1H), 9.12 (s, 1H), 8.04 (bs, 1H), 7.42 (d, J=8 Hz, 2H), 7.34-7.30 (m, 4H), 6.66 (d, J=8.4 Hz, 2H), 6.47 (s, 1H), 4.34 (t, J=4 Hz, 1H), 3.45 (s, 3H), 3.18-3.16 (m, 2H), 2.36 (s, 3H) 1.59 (s, 3H). MS (ESI): mass calcd for $C_{28}H_{24}ClN_3O_3S$, 517.2; m/z, found: 518.1 [M+H]$^+$.

Example 5: (R)-2-(4-(4-cyanophenyl)-2,3,9-trimethyl-8-oxo-8,9-dihydro-6H-pyrido[4,3-c]thieno[2,3-e]azepin-6-yl)-N-ethylacetamide

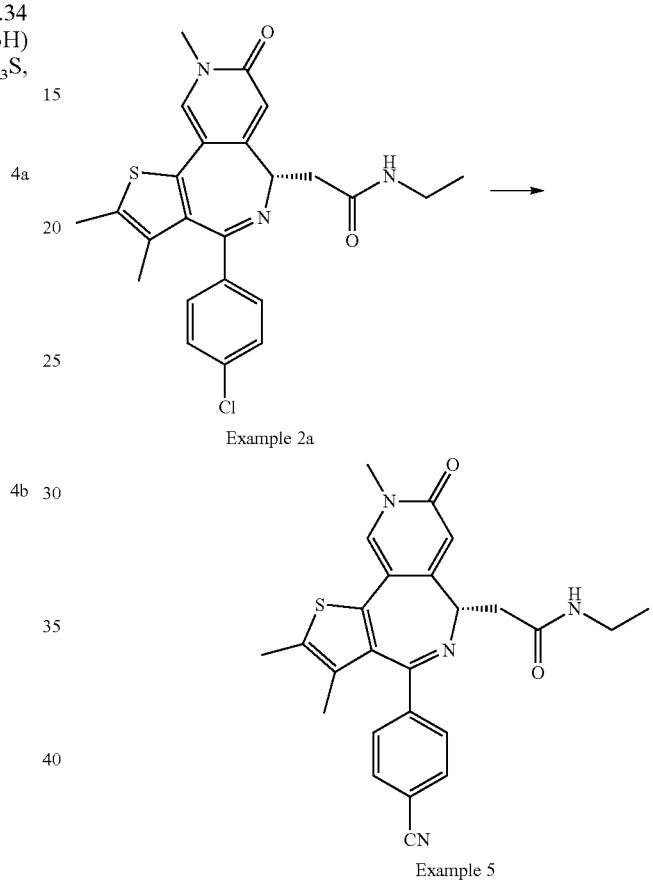

Example 2a

Example 5

To a stirred solution of (R)-2-(4-(4-chlorophenyl)-2,3,9-trimethyl-8-oxo-8,9-dihydro-6H-pyrido[4,3-c]thieno[2,3-e]azepin-6-yl)-N-ethylacetamide (0.1 g, 0.22 mmol, Example 2a) in DMF (2 mL), was added Zn(CN)$_2$ (0.04 g, 0.33 mmol) reaction mixture was purged with nitrogen gas for 15 minutes. To the reaction mixture was added dppf, (12 mg, 0.02 mmol) and Pd$_2$(dba)$_3$ (10 mg, 0.01 mmol). The reaction mixture was heated in a sealed tube at 130° C. for 16 h. The mixture was quenched with water and concentrated to remove DMF. To the residue was added 5% MeOH in DCM. The organic layer containing product was washed with cold water, dried over Na$_2$SO$_4$, concentrated under reduced pressure. The crude was purified by combiflash (elution with 1-5% MeOH/DCM) to give off white solid (0.018 g, 40% yield). $^1$H-NMR (DMSO-$d_6$, 400 MHz) δ (ppm): 8.13 (t, 1H), 8.04 (s, 1H), 7.43 (d, J=8.4 Hz, 2H), 7.47 (d, J=8.4 Hz, 2H), 6.42 (s, 1H), 4.3 (t, J=7.6 Hz, 1H), 3.45 (s, 3H), 3.11-3.04 (m, 2H), 2.98-2.96 (m, 2H), 2.36 (s, 3H), 1.56 (s, 3H), 1.01 (t, J=7.6 Hz, 3H). MS (ESI): mass calcd. for $C_{25}H_{24}N4O_2S$, 444.56; m/z found, 445.1 [M+H]$^+$.

Example 6: ±Ethyl 2-(4-(4-chlorophenyl)-2,9-dimethyl-8-oxo-8,9-dihydro-6H-pyrido[4,3-c]thiazolo[5,4-e]azepin-6-yl)acetate

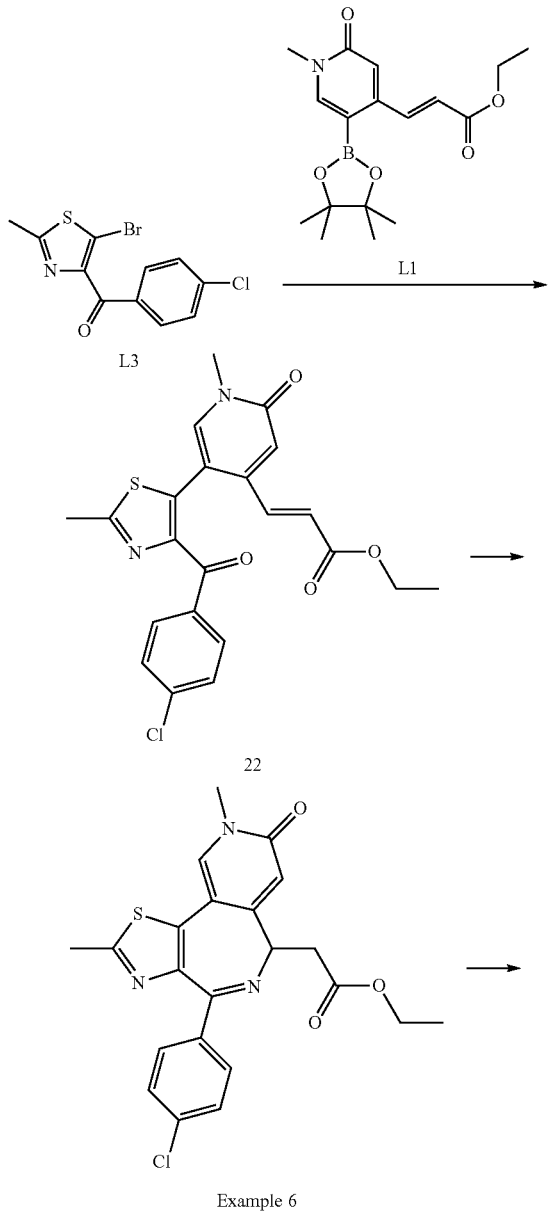

Example 6

Preparation of (E)-ethyl 3-(5-(4-(4-chlorobenzoyl)-2-methylthiazol-5-yl)-1-methyl-2-oxo-1,2-dihydropyridin-4-yl)acrylate (22)

To a stirred solution of (5-bromo-2-methylthiazol-4-yl)(4-chlorophenyl)methanone (Intermediate L3, 0.24 g, 0.75 mmol) in toluene (3 mL), (E)-ethyl 3-(1-methyl-2-oxo-5-(4,4,5,5-tetramethyl-1,3,2-dioxaborolan-2-yl)-1,2-dihydropyridin-4-yl)acrylate (Intermediate L1, 0.33 g, 0.99 mmol), 2N sodium bicarbonate (0.76 mL, 1.52 mmol) was added at room temperature and purged with nitrogen gas for 15 minutes, followed by Pd(PPh$_3$)$_4$(0.087 g, 0.075 mmol) was added under nitrogen atmosphere. The mixture was stirred for 12 h at 110° C. The reaction mixture was cooled to room temperature and concentrated the mixture under reduced pressure. The crude product was dissolved in ethyl acetate and was washed with brine, dried over anhydrous sodium sulphate, concentrated under reduced pressure. The crude was purified by combiflash (silica gel, 5-60% ethylacetate/hexane) to give brown solid (0.18 g, 53% yield). MS (ESI): mass calcd. for C$_{22}$H$_{19}$ClN$_2$O$_4$S, 442.92; m/z, found: 443.1 [M+H]$^+$.

Example 6: ±Ethyl 2-(4-(4-chlorophenyl)-2,9-dimethyl-8-oxo-8,9-dihydro-6H-pyrido[4,3-c]thiazolo[5,4-e]azepin-6-yl)acetate To a stirred solution of (E)-ethyl 3-(5-(4-(4-chlorobenzoyl)-2-methylthiazol-5-yl)-1-methyl-2-oxo-1,2-dihydropyridin-4-yl)acrylate (22, 0.18 g, 0.4 mmol) in EtOH (4 mL) was added ammonium formate (1.03 mL, 16.28 mmol) at room temperature. The mixture was stirred at 85° C. for 18 h. Reaction mixture was concentrated to get solid residue. The residue was dissolved in water and extracted with 10% MeOH/dichloromethane twice, washed with brine, dried over sodium sulphate, concentrated. The crude was purified by combiflash (Silica gel, 2-4% MeOH/dichloromethane) to get product as a off white solid. $^1$H NMR (DMSO-d$_6$, 400 MHz) δ (ppm): 8.16 (s, 1H), 7.51 (d, J=8.8 Hz, 2H), 7.43 (d, J=8.4 Hz, 2H), 6.43 (s, 1H), 4.29-4.26 (t, J=4.4 Hz, 1H), 4.1-4.07 (m, 2H), 3.46 (s, 3H), 3.38-3.33 (s, 3H), 3.12 (m, 2H), 1.18-1.15 (t, J=10.4 Hz, 3H), MS (ESI): mass calcd. for C$_{22}$H$_{20}$ClN$_3$O$_3$S, 441.94; m/z, found: 442.0 [M+H]$^+$.

Example 7: ±2-(4-(4-chlorophenyl)-2,9-dimethyl-8-oxo-8,9-dihydro-6H-pyrido[4,3-c]thiazolo[5,4-e]azepin-6-yl)-N-ethylacetamide To a stirred solution of Ethyl 2-(4-(4-chlorophenyl)-2,9-dimethyl-8-oxo-8,9-dihydro-6H-pyrido[4,3-c]thiazolo[5,4-e]azepin-6-yl)acetate (Example 6, 0.05 g, 0.113 mmol) in dry THF (100 mL), ethylamine (0.45 mL, 0.9 mmol, THF solution) followed by trimethyl aluminum (0.45 mL, 0.9 mmol) at 0° C. The mixture was stirred for 6 h at 90° C. The mixture was quenched with saturated ammonium chloride. The residue was partitioned between ethyl acetate and water. The organic layer was washed with brine, dried over sodium sulphate, concentrated under reduced pressure. The crude product was purified by combiflash purifier by using 2-3% MeOH/dichloromethane to get the product as off white solid. (0.02 g, 40% yield).
$^1$H NMR (DMSO-d$_6$, 400 MHz) δ (ppm): 8.14 (bs, 2H), 7.53 (d, J=8.8 Hz, 2H), 7.42 (d, J=8.4 Hz, 2H), 6.42 (s, 1H), 4.3 (t, J=6 Hz, 1H), 3.45 (s, 3H), 3.14-3.02 (m, 3H), 2.94-2.9 (m, 1H), 2.7 (s, 3H), 1.01 (t, J=7.2 Hz, 3H). MS (ESI): mass calcd. for C$_{22}$H$_{21}$ClN$_4$O$_2$S, 440.96; m/z, found: 441.1.

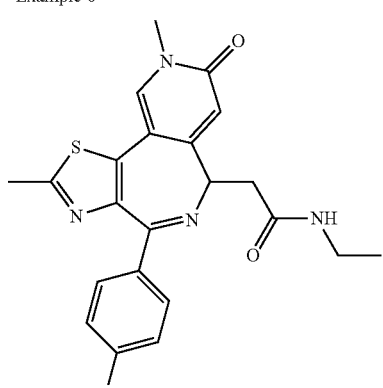

Example 7

Preparative Chiral HPLC Method for the Separation of Enantiomers of Example 7

CHIRALPAK IA (250 mm×4.6 mm×5 m)
Wavelength monitored 254 nm
Mobile phase: 0.1% DEA in 100% MEOH

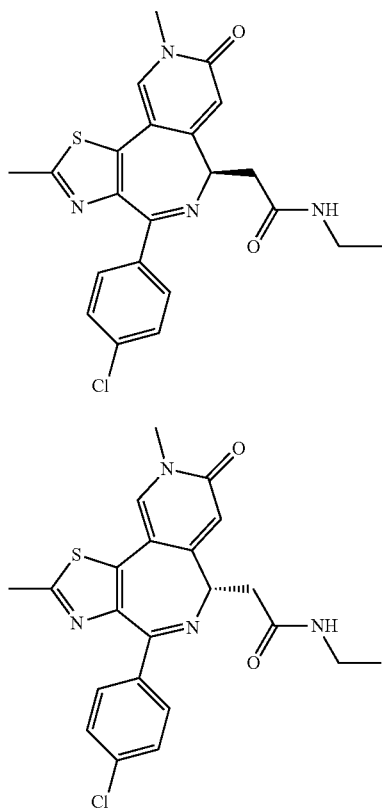

Example 7a

Example 7b

Example 7a: (R)-2-(4-(4-chlorophenyl)-2,9-dimethyl-8-oxo-8,9-dihydro-6H-pyrido[4,3-c]thiazolo[5,4-e]azepin-6-yl)-N-ethylacetamide 1H NMR (DMSO-$d_6$, 400 MHz) δ (ppm): 8.14 (bs, 2H), 7.53 (d, J=8.8 Hz, 2H), 7.42 (d, J=8.4 Hz, 2H), 6.42 (s, 1H), 4.3 (t, J=6 Hz, 1H), 3.45 (s, 3H), 3.14-3.02 (m, 3H), 2.94-2.90 (m, 1H), 2.7 (s, 3H), 1.01 (t, J=7.2 Hz, 3H). MS (ESI): mass calcd. for $C_{22}H_{21}ClN_4O_2S$, 440.96; m/z, found: 441.1.

Example 7b: (S)-2-(4-(4-chlorophenyl)-2,9-dimethyl-8-oxo-8,9-dihydro-6H-pyrido[4,3-c]thiazolo[5,4-e]azepin-6-yl)-N-ethylacetamide 1H NMR (DMSO-$d_6$, 400 MHz) δ (ppm): 8.14 (bs, 2H), 7.53 (d, J=8.8 Hz, 2H), 7.42 (d, J=8.4 Hz, 2H), 6.42 (s, 1H), 4.3 (t, J=6 Hz, 1H), 3.45 (s, 3H), 3.14-3.02 (m, 3H), 2.94-2.90 (m, 1H), 2.7 (s, 3H), 1.01 (t, J=7.2 Hz, 3H). MS (ESI): mass calcd. for $C_{22}H_{21}ClN_4O_2S$, 440.96; m/z, found: 441.1.

Example 8: ±ethyl 2-(5-(4-chlorophenyl)-10-methyl-9-oxo-9,10-dihydro-7H-dipyrido[3,2-c:3',4'-e]azepin-7-yl)acetate Intermediate L1 + Intermediate L4 ⟶

23

Example 8

Preparation of (E)-ethyl 3-(3-(4-chlorobenzoyl)-1'-methyl-6'-oxo-1',6'-dihydro-[2,3'-bipyridin]-4'-yl)acrylate (23)

To a stirred solution of (2-bromopyridin-3-yl)(4-chlorophenyl)methanone (Intermediate L4, 0.5 g, 1.5 mmol) in dimethoxy ethane/water (60:15 mL), was added (E)-ethyl 3-(1-methyl-2-oxo-5-(4,4,5,5-tetramethyl-1,3,2-dioxaborolan-2-yl)-1,2-dihydropyridin-4-yl)acrylate (Intermediate L1, 0.45 g, 1.5 mmol), sodium carbonate (0.5 g, 4.5 mmol) at room temperature and purged with nitrogen gas for 15 min, followed by Pd(PPh$_3$)$_4$(0.2 g, 0.15 mmol) was added under nitrogen atmosphere. The mixture was stirred for 1 h at 90° C. The reaction mixture was cooled to room temperature and concentrated under reduced pressure. The residue was partitioned with ethyl acetate and water. The organic layer was washed with brine, dried over sodium sulphate, concentrated under reduced pressure. The crude was purified by combiflash (silica gel, 60-70% ethylacetate/hexane) to give ~50% product. MS (ESI): mass calcd. for $C_{23}H_{19}ClN2O_4$, 422.8; m/z, found: 423 [M+H]$^+$.

Example 8: ±ethyl 2-(5-(4-chlorophenyl)-10-methyl-9-oxo-9,10-dihydro-7H-dipyrido[3,2-c:3',4'-e]azepin-7-yl)acetate To a stirred solution of (E)-ethyl 3-(3-(4-chlorobenzoyl)-1'-methyl-6'-oxo-1',6'-dihydro-[2,3'-bipyridin]-4'-yl)acrylate. (23, 0.3 g, 0.71 mmol) in EtOH (4 mL) was added ammonium formate (5.0 g, 32 mmol) at room temperature. The mixture was stirred at 85° C. for 18 h in an autoclave vessel. Reaction mixture was concentrated to get solid residue. The residue was dissolved in water and extracted with 10% MeOH/dichloromethane twice, washed with brine, dried over sodium sulphate, concentrated. The crude product was purified by combiflash (silica gel, 2-4% MeOH/dichloromethane) to get 40% product. MS (ESI): mass calcd. for $C_{23}H_{20}ClN_3O_3$, 421.92; m/z, found: 424.0 $[M+H]^+$.

Example 9: ±ethyl 2-(4-(cyclopropylmethyl)-2,3,9-trimethyl-8-oxo-8,9-dihydro-6H-pyrido[4,3-c]thieno[2,3-e]azepin-6-yl)acetate Intermediate L1 + Intermediate L5 ⟶

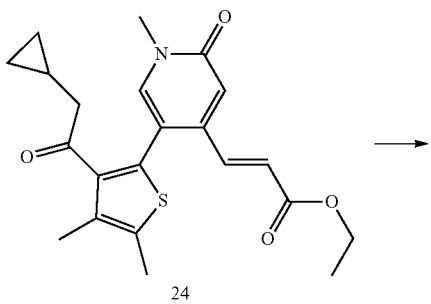

24

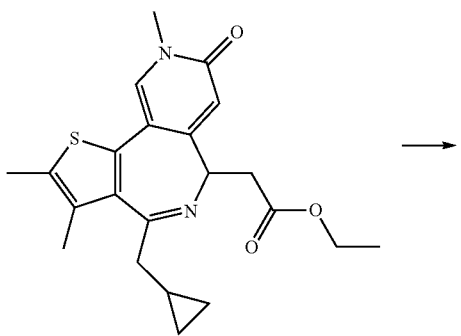

Example 9

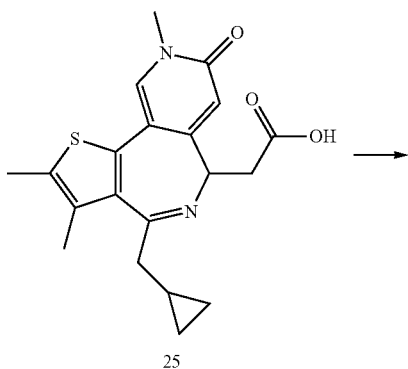

25

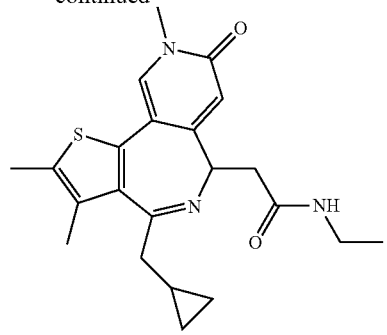

Example 10

Preparation of Ethyl (E)-3-(5-(3-(2-cyclopropylacetyl)-4,5-dimethylthiophen-2-yl)-1-methyl-2-oxo-1,2-dihydropyridin-4-yl)acrylate (24)

A mixture of 1-(2-bromo-4,5-dimethylthiophen-3-yl)-2-cyclopropylethan-1-one 0(0.8 g, 2.93 mmol, L5), ethyl (E)-3-(1-methyl-2-oxo-5-(4,4,5,5-tetramethyl-1,3,2-dioxaborolan-2-yl)-1,2-dihydropyridin-4-yl)acrylate (L1, 1.17 g, 3.51 mmol) and 2M sodium bicarbonate (0.98 g, 11.72 mmol) were mixed in toluene (30 mL). The mixture was purged with nitrogen gas for 10 minutes. Then added tetrakis (triphenylphosphine) palladium(0) (0.68 g, 0.58 mmol) to the mixture and again nitrogen gas was purged through the mixture for 5 minutes. The mixture was heated to 105° C. after 15 h reaction mixture was cooled to room temperature, diluted with water (100 mL) and extracted with ethyl acetate (100 mL). Organic layers were combined, washed with brine, dried over anhydrous sodium sulphate and concentrated to give a residue. The crude was purified by combiflash eluting with 0-10% MeOH/DCM. The pure fractions were concentrated to obtain to afford ethyl (E)-3-(5-(3-(2-cyclopropylacetyl)-4,5-dimethylthiophen-2-yl)-1-methyl-2-oxo-1,2-dihydropyridin-4-yl)acrylate (0.42 g, 36%, yield) as a pale pink colored liquid. $^1$HNMR: (400 MHz, DMSO-$d_6$) δ (ppm): 7.89 (s, 1H), 7.22 (d, J=36 Hz, 1H), 6.85 (s, 1H), 6.59 (d, J=16 Hz, 1H), 4.11 (q, J=8 Hz, 2H), 3.42 (s, 3H), 2.32 (s, 3H), 2.25 (d, J=8 Hz, 2H), 2.08 (s, 3H), 1.24 (t, J=8 Hz, 3H), 0.78 (m, 1H), 0.36-0.31 (m, 2H), 0.16-0.14 (m, 2H). MS (ESI): mass calcd for $C_{22}H_{25}NO_4S$, 399.15; m/z found, 400.1 [M+H].

Example 9: ±ethyl 2-(4-(cyclopropylmethyl)-2,3,9-trimethyl-8-oxo-8,9-dihydro-6H-pyrido[4,3-c]thieno[2,3-e]azepin-6-yl)acetate A solution of ethyl (E)-3-(5-(3-(2-cyclopropylacetyl)-4,5-dimethylthiophen-2-yl)-1-methyl-2-oxo-1,2-dihydropyridin-4-yl)acrylate (24, 0.2 g, 0.5 mmol) in ethanol (5 mL), ammonium formate (1.26 g, 20.0 mmol) was added and heated to 90° C. After 24 h the reaction mixture was cooled to room temperature and diluted with ethyl acetate and washed with water and brine. The organic layer was dried over anhydrous sodium sulphate and concentrated to give a residue. The crude was purified by combi-flash eluting with 0-10% MeOH:DCM. The pure fractions were concentrated to afford ethyl 2-(4-(cyclopropylmethyl)-2,3,9-trimethyl-8-oxo-8,9-dihydro-6H-pyrido[4,3-c]thieno[2,3-e]azepin-6-yl) acetate (0.145 g. 70%, yield) as a pale yellow colored solid. MS (ESI): mass calcd for $C_{22}H_{26}N_2O_3S$, 398.17; m/z, found: 399.2 [M+H].

Preparation of 2-(4-(cyclopropylmethyl)-2,3,9-trimethyl-8-oxo-8,9-dihydro-6H-pyrido[4,3-c]thieno[2,3-e]azepin-6-yl)acetic acid (25)

Ethyl 2-(4-(cyclopropylmethyl)-2,3,9-trimethyl-8-oxo-8,9-dihydro-6H-pyrido[4,3-c]thieno[2,3-e]azepin-6-yl)acetate (Example 9, 0.14 mg, 0.35 mmol) was dissolved in methanol (3 mL) to this 4N sodium hydroxide (0.28 g, 7.0 mmol) was added and stirred at room temperature. After 4 h the volatiles were removed and the residue was dissolved in water and acidified with 2N hydrochloric acid. The precipitation was collected by filtration and dried to obtain 2-(4-(cyclopropylmethyl)-2,3,9-trimethyl-8-oxo-8,9-dihydro-6H-pyrido[4,3-c]thieno[2,3-e]azepin-6-yl)acetic acid (0.11 g, 85%, yield) as a pale yellow color solid. MS (ESI): mass calcd for $C_{20}H_{22}N_2O_3S$, 370.14; m/z, found: 371.2 [M+H].

Example 10: ±2-(4-(cyclopropylmethyl)-2,3,9-trimethyl-8-oxo-8,9-dihydro-6H-pyrido[4,3-c]thieno[2,3-e]azepin-6-yl)-N-ethylacetamide A solution of 2-(4-(cyclopropylmethyl)-2,3,9-trimethyl-8-oxo-8,9-dihydro-6H-pyrido[4,3-c]thieno[2,3-e]azepin-6-yl)acetic acid (25, 0.105 g, 0.2 mmol) and HATU (0.161 g, 0.4 mmol) were taken in DMF (1 mL), stirred at 25° C. After 5 min ethylamine (0.1 mL, 1.0 mmol, THF solution) was added and stirred for 1 h at same temperature. The reaction mixture was diluted with ethyl acetate and washed with water. The organic layer was dried over anhydrous sodium sulphate and concentrated to give a residue. The crude was purified by combi-flash eluting with 0-10% MeOH/DCM. The pure fractions were concentrated to afford 2-(4-(cyclopropylmethyl)-2,3,9-trimethyl-8-oxo-8,9-dihydro-6H-pyrido[4,3-c]thieno[2,3-e]azepin-6-yl)-N-ethylacetamide (0.04 g, 35%, yield) as a pale yellow color solid. $^1$HNMR: (400 MHz, DMSO-$d_6$) δ (ppm): 8.04 (t, 1H), 7.93 (s, 1H), 6.36 (s, 1H), 4.09 (t, J=8 Hz, 1H), 3.44 (s, 3H), 3.04-3.00 (m, 2H), 2.96-2.87 (m, 1H), 2.78-2.73 (m, 1H), 2.65-2.47 (m, 1H), 2.35 (s, 3H), 2.25-2.19 (m, 1H), 2.16 (m, 3H), 0.96 (t, J=12 Hz, 3H), 0.61 (m, 1H), 0.20-0.14 (m, 2H), −0.09-0.13 (m, 2H). MS (ESI): mass calcd for $C_{22}H_{27}N_3O_2S$, 397.18; m/z found, 398.2[M+H].

Example 11: ±Ethyl-2-(7-(4-chlorophenyl)-9-methoxy-2-methyl-3-oxo-3,5-dihydro-2H-dipyrido[4,3-c:3',4'-e]azepin-5-yl)acetate

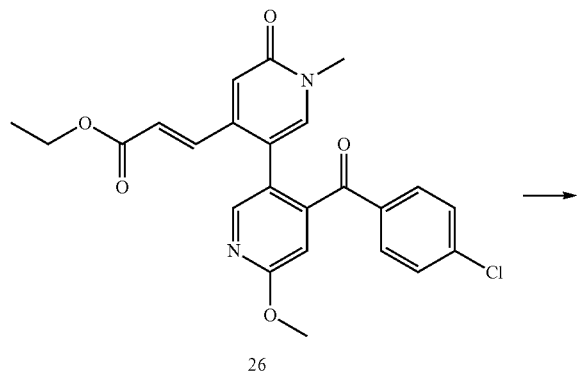

26

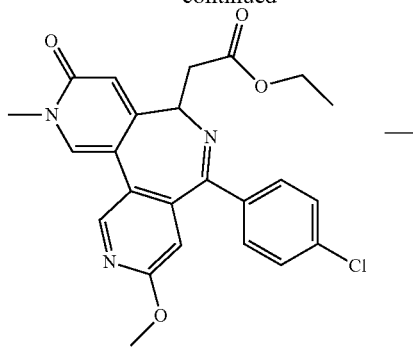

Example 11

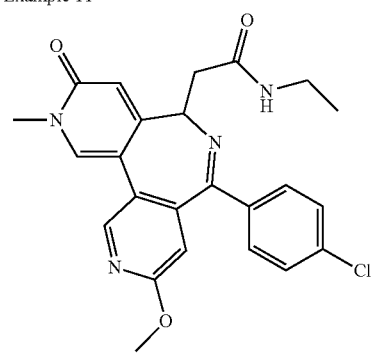

Example 12

Preparation of ±Ethyl-2-(7-(4-chlorophenyl)-9-methoxy-2-methyl-3-oxo-3,5-dihydro-2H-dipyrido[4,3-c:3',4'-e]azepin-5-yl)acetate A solution of ethyl (E)-3-(4'-(4-chlorobenzoyl)-6'-methoxy-1-methyl-6-oxo-1,6-dihydro-[3,3'-bipyridin]-4-yl)acrylate (26, 0.36 g, 0.79 mmol) in ethanol (5 mL) in seal tube, ammonium formate (1.0 g, 15.9 mmol) was added and heated to 90° C. After 15 h the reaction mixture was cooled to room temperature and diluted with ethyl acetate and washed with water and brine. The organic layer was dried over anhydrous sodium sulphate and concentrated to get residue. The crude was purified by combi-flash eluting with 0-10% MeOH/DCM. The pure fractions were concentrated to afford the title compound (0.33 g, 90%, yield) as a pale yellow colored solid. MS (ESI): mass calcd for $C_{24}H_{22}ClN_3O_4$, 451.13; m/z found, 452.1 [M+1].

Example 12: ±2-(7-(4-chlorophenyl)-9-methoxy-2-methyl-3-oxo-3,5-dihydro-2H-dipyrido[4,3-c:3',4'-e]azepin-5-yl)-N-ethylacetamide To a stirred solution of ethyl 2-(7-(4-chlorophenyl)-9-methoxy-2-methyl-3-oxo-3,5-dihydro-2H-dipyrido[4,3-c:3',4'-e]azepin-5-yl)acetate (Example 11, 0.33 g, 0.72 mmol) in dry THF (1 mL), ethyl amine (1.8 mL, 3.6 mmol) followed by trimethyl aluminum (1M, 4.6 mL, 3.6 mmol) at 0° C. in sealed tube. The mixture was stirred for 6 h at 90° C. The mixture was quenched with saturated ammonium chloride. The residue was partitioned between ethyl acetate and water. The organic layer was washed with brine, dried over sodium sulphate, concentrated under reduced pressure. The crude product was purified by combiflash (silica gel) by using 0-10% MeOH/DCM to afford 2-(7-(4-chlorophenyl)-9-methoxy-2-methyl-3-oxo-3,5-dihydro-2H-dipyrido[4,3-c:3', 4'-e]azepin-5-yl)-N-ethylacetamide (0.16 g, 45% yield) as off white solid. ¹HNMR: (400 MHz, DMSO-d₆) δ (ppm): 8.53 (s, 1H), 8.11-8.04 (m, 2H), 7.50-7.45 (m, 4H), 6.63 (s, 1H), 6.39 (s, 1H), 4.26 (t, 1H, J=8 Hz, 1H), 3.91 (s, 3H), 3.44 (s, 3H), 3.09-3.04 (m, 2H), 2.94-2.92 (m, 2H), 1.00 (t, J=7.4 Hz, 3H): MS (ESI): mass calcd for C₂₄H₂₃ClN₄O₃, 450.15; m/z found, 451.3 [M+1].

Preparative Chiral HPLC Method for the Separation of Enantiomers (u and v)

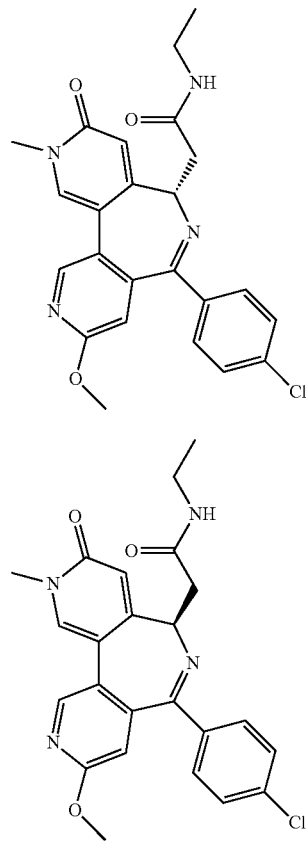

12a

12b

Column: CHIRALPAK IA (250 mm×4.6 mm×5 μm)
Wavelength monitored: 265 nm
Mobile phase: 0.1% DEA in 100% MEOH Example 12a: (S)-2-(7-(4-chlorophenyl)-9-methoxy-2-methyl-3-oxo-3,5-dihydro-2H-dipyrido[4,3-c:3',4'-e]azepin-5-yl)-N-ethylacetamide 1HNMR: (400 MHz, DMSO-d₆) δ (ppm): 8.53 (s, 1H), 8.11-8.04 (m, 2H), 7.50-7.40 (m, 4H), 6.63 (s, 1H), 6.39 (s, 1H), 4.26 (t, 1H, J=8 Hz, 1H), 3.91 (s, 3H), 3.44 (s, 3H), 3.09-3.04 (m, 2H), 2.94-2.92 (m, 2H), 1.00 (t, J=4 Hz, 3H): MS (ESI): mass calcd for C₂₄H₂₃ClN₄O₃, 450.15; m/z found, 451.3 [M+1].

Example 12b: (R)-2-(7-(4-chlorophenyl)-9-methoxy-2-methyl-3-oxo-3,5-dihydro-2H-dipyrido[4,3-c:3',4'-e]azepin-5-yl)-N-ethylacetamide ¹HNMR: (400 MHz, DMSO-d₆) δ (ppm): 8.53 (s, 1H), 8.11-8.04 (m, 2H), 7.45 (m, 4H), 6.63 (s, 1H), 6.39 (s, 1H), 4.26 (t, 1H, J=8 Hz, 1H), 3.91 (s, 3H), 3.44 (s, 3H), 3.09-3.04 (m, 2H), 2.94-2.92 (m, 2H), 1.00 (t, J=4 Hz, 3H): MS (ESI): mass calcd for C₂₄H₂₃ClN₄O₃, 450.15; m/z found, 451.3 [M+1].

Example 13: ±ethyl 2-(4-(4-chlorophenyl)-3,9-dimethyl-8-oxo-3,6,8,9-tetrahydropyrazolo[3,4-c]pyrido[3,4-e]azepin-6-yl)acetate

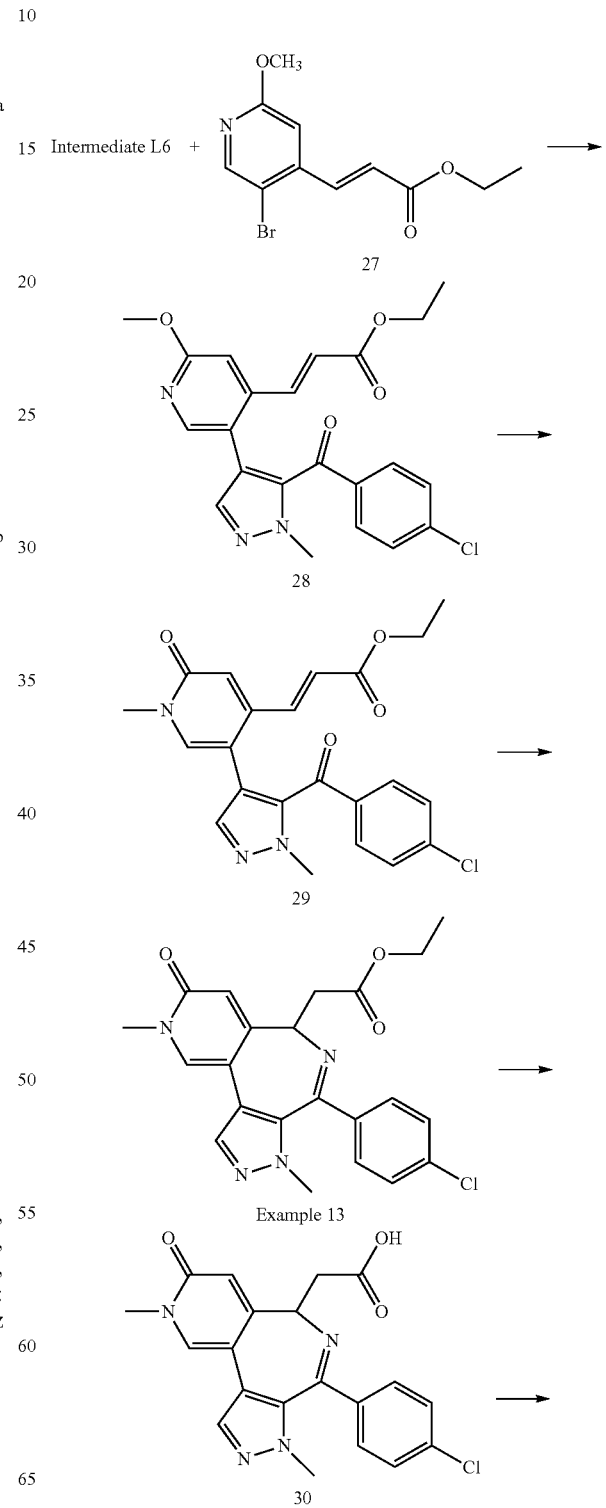

Example 13

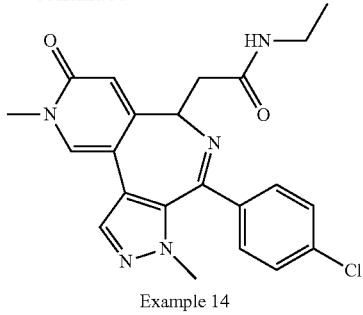

Example 14

Preparation of Ethyl (E)-3-(5-(5-(4-chlorobenzoyl)-1-methyl-1H-pyrazol-4-yl)-2-methoxypyridin-4-yl)acrylate (28)

To a stirred solution of ethyl (E)-3-(5-bromo-2-methoxypyridin-4-yl)acrylate (27, 3.0 g, 0.011 mol) in toluene (50 mL) was added (4-chlorophenyl)(1-methyl-4-(4,4,5,5-tetramethyl-1,3,2-dioxaborolan-2-yl)-1H-pyrazol-5-yl)methanone (Intermediate L6, 4.3 g, 0.013 mol) followed by aqueous sat. NaHCO3 solution (3.5 g, 0.042 mol) and de-gassing was done for 10 min. Then tetrakis(triphenylphosphine)palladium(0) catalyst (2. g, 0.002 mol) was added. Then reaction mixture was refluxed for overnight. After completion of reaction, confirmed by TLC, reaction mixture was filtered and concentrated. Residue was dissolved in ethyl acetate, washed with water, brine, dried over anhydrous sodium sulphate. Organic layer was concentrated and purified by combiflash (silica gel:ethyl acetate/hexane), desired compound was eluted in 13% EA/hexane. The column fractions containing required product were collected and evaporated to get the title compound (2.0 g, 45% yield). MS (ESI): mass calcd. For $C_{22}H_{20}ClN_3O_4$, 425.11; m/z, found: 426.1 [M+H]$^+$.

Preparation of ethyl (E)-3-(5-(5-(4-chlorobenzoyl)-1-methyl-1H-pyrazol-4-yl)-1-methyl-2-oxo-1,2-dihydropyridin-4-yl)acrylate (29)

To a stirring solution of ethyl (E)-3-(5-(5-(4-chlorobenzoyl)-1-methyl-1H-pyrazol-4-yl)-2-methoxypyridin-4-yl)acrylate (28, 2.0 g, 0.0047 mol) in acetonitrile (5 mL) was added methyl iodide (1.46 mL, 0.024 mol). Reaction mixture was heated at 90° C. for overnight in a sealed tube. After completion of reaction, confirmed by TLC, reaction mixture was concentrated and purified by combiflash (neutral alumina: MeOH/DCM). The column fractions containing required the product were collected and evaporated to get ethyl(E)-3-(5-(5-(4-chlorobenzoyl)-1-methyl-1H-pyrazol-4-yl)-1-methyl-2-oxo-1,2-dihydropyridin-4-yl)acrylate (1.0 g; 50% yield). MS (ESI): mass calcd. For $C_{22}H_{20}ClN_3O_4$, 425.11; m/z, found: 426.1[M+H]$^+$.

Example 13: ±ethyl (Z)-2-(4-(4-chlorophenyl)-3,9-dimethyl-8-oxo-8,9-dihydropyrazolo[3,4-c]pyrido[3,4-e]azepin-6(3H)-ylidene)acetate To a stirred solution of ethyl (E)-3-(5-(5-(4-chlorobenzoyl)-1-methyl-1H-pyrazol-4-yl)-1-methyl-2-oxo-1,2-dihydropyridin-4-yl)acrylate (29, 0.3 g, 0.007 mol) in EtOH (10 mL) was added ammonium formate (1.8 g, 0.0282 mol) and heated for overnight at 85° C. After completion of reaction, confirmed by TLC, ethanol was evaporated and the residue was dissolved in ethyl acetate was washed with brine, dried over anhydrous sodium sulphate and concentrated. The compound was purified by combiflash (neutral alumina: MeOH/DCM) desired compound was eluted in 5% MeOH/DCM. The column fractions containing required product were collected and evaporated to get the title compound (0.08 g; 26% yield). $^1$H NMR: (400 MHz, DMSO-d$_6$) δ (ppm): 8.15 (s, 1H), 7.96 (s, 1H), 7.51 (d, J=8.0 Hz, 2H), 7.34 (d, J=8.4 Hz, 2H), 6.41 (s, 1H), 4.25 (m, 1H), 4.23-4.04 (m, 2H), 3.45 (s, 6H), 3.33-3.19 (m, 2H), 1.16 (t, J=, 3H). MS (ESI): mass calcd. For $C_{22}H_{19}ClN_4O_3$, 424.13; m/z, found: 425.2[M+H]$^+$.

Preparation of 2-(4-(4-chlorophenyl)-3,9-dimethyl-8-oxo-3,6,8,9-tetrahydropyrazolo[3,4-c]pyrido[3,4-e]azepin-6-yl)acetic acid (30)

To a stirred solution of ethyl (Z)-2-(4-(4-chlorophenyl)-3,9-dimethyl-8-oxo-8,9-dihydropyrazolo[3,4-c]pyrido[3,4-e]azepin-6(3H)-ylidene)acetate (0.3 g; 0.007 mol) in MeOH (10 mL) was added 4N NaOH solution and stirred for 2 h at room temperature. After completion of reaction, confirmed by TLC, MeOH was evaporated and the residue was dissolved in ethyl acetate and extracted with water. The aqueous layer was acidified with 2N HCl to pH 3 and precipitate formed was filtered and washed with diethylether to get the title compound. (0.2 g, 70% yield). MS (ESI): mass calcd. For C20H15ClN4O3, 396.10; m/z, found: 397.1[M+H]$^+$.

Example 14: ±2-(4-(4-chlorophenyl)-3,9-dimethyl-8-oxo-3,6,8,9-tetrahydropyrazolo[3,4-c]pyrido[3,4-e]azepin-6-yl)-N-ethylacetamide To a stirred solution of (Z)-2-(4-(4-chlorophenyl)-3,9-dimethyl-8-oxo-8,9-dihydropyrazolo[3,4-c]pyrido[3,4-e]azepin-6(3H)-ylidene)acetic acid (30, 0.2 g, 0.5 mmol) in DMF (10 mL) was added HATU (0.29 g, 0.75 mmol). After 5 min of stirring ethylamine (0.113 g, 2.5 mmol) was added followed by DIPEA (0.16 mL, 0.1 mmol) and reaction mixture was left for stirring 30 min. After completion of reaction, confirmed by TLC, crushed ice was added into reaction mixture and extracted with ethyl acetate. The organic layer was washed with brine, dried over anhydrous sodium sulphate and concentrated. The compound was purified by combiflash (neutral alumina: MeOH/DCM) desired compound was eluted in 5% MeOH/DCM. The column fractions containing required product were collected and evaporated to get the product (0.21 g; 99% yield). MS (ESI): mass calcd. For $C_{22}H_{22}ClN_5O_2$, 423.15; m/z, found: 424.1 [M+H]$^+$.

Preparative Chiral HPLC method for the separation of enantiomers (14a and 14b):

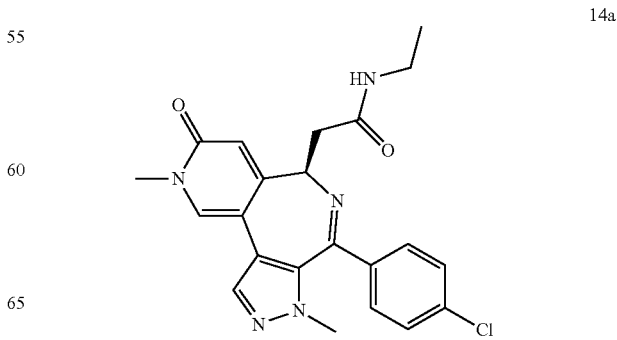

14a

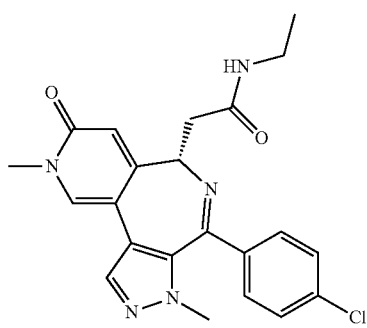

14b

Example 14a: (R)-2-(4-(4-chlorophenyl)-3,9-dimethyl-8-oxo-3,6,8,9-tetrahydropyrazolo[3,4-c]pyrido[3,4-e]azepin-6-yl)-N-ethylacetamide $^1$HNMR: (400 MHz, DMSO-d$_6$) δ (ppm): 8.16 (bs, 1H), 8.13 (s, 1H), 7.94 (s, 1H), 7.72 (d, J=8.4 Hz, 2H), 7.44 (d, J=8.4 Hz, 2H), 6.41 (s, 1H), 4.35 (bs, 1H), 4.00 (s, 3H), 2.89-2.84 (m, 1H), 1.00 (t, J=7.6 Hz, 3H). MS (ESI): mass calcd. For C$_{22}$H$_{22}$ClN$_5$O2, 423.15; m/z, found: 424.1 [M+H]$^+$.

Example 14b: (S)-2-(4-(4-chlorophenyl)-3,9-dimethyl-8-oxo-3,6,8,9-tetrahydropyrazolo[3,4-c]pyrido[3,4-e]azepin-6-yl)-N-ethylacetamide $^1$HNMR: (400 MHz, DMSO-d$_6$) δ (ppm): 8.16 (bs, 1H), 8.13 (s, 1H), 7.94 (s, 1H), 7.72 (d, J=8.4 Hz, 2H), 7.44 (d, J=8.4 Hz, 2H), 6.41 (s, 1H), 4.35 (bs, 1H), 4.00 (s, 3H), 2.89-2.84 (m, 1H), 1.00 (t, J=7.6 Hz, 3H). MS (ESI): mass calcd. For C$_{22}$H$_{22}$ClN$_5$O2, 423.15; m/z, found: 424.1 [M+H]$^+$.

Example 15: ±ethyl 2-(4-(4-chlorophenyl)-8-methoxy-2,3-dimethyl-4,6-dihydrothieno[2',3':5,6]oxepino[4,3-c]pyridin-6-yl)acetate

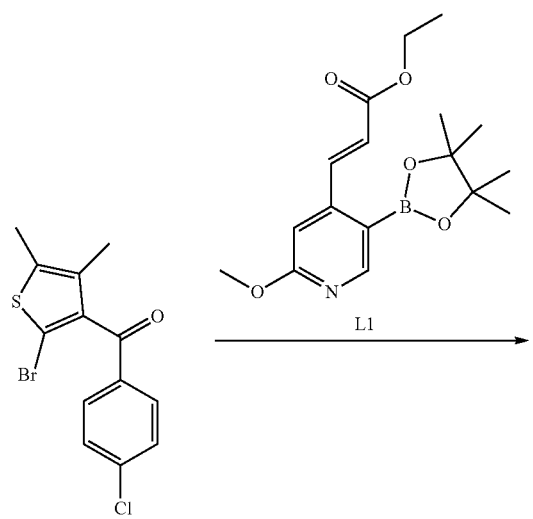

Intermediate L2

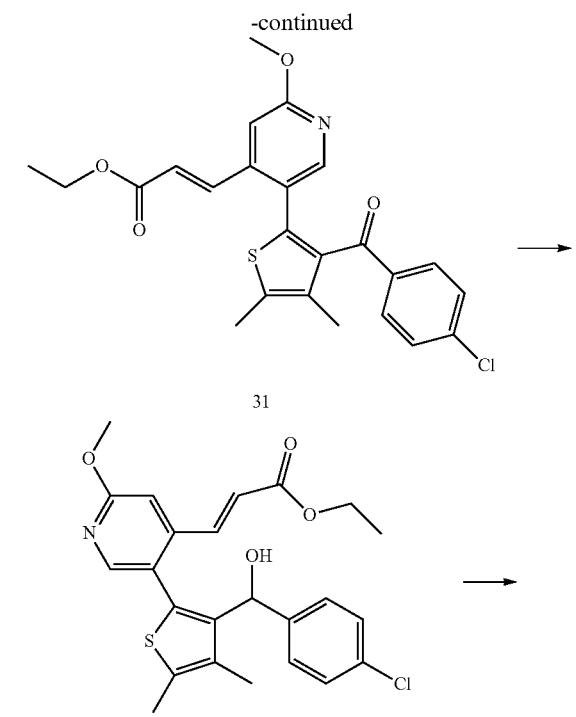

31

32

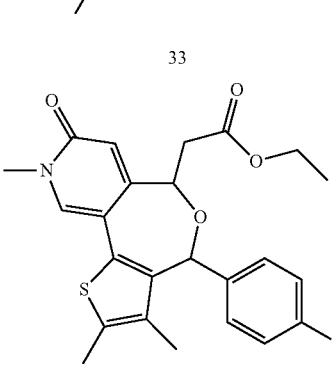

33

Example 15

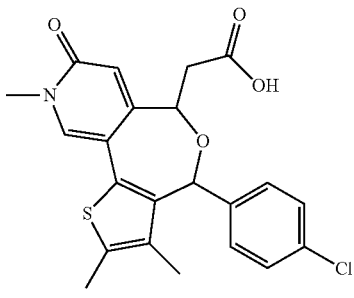

34

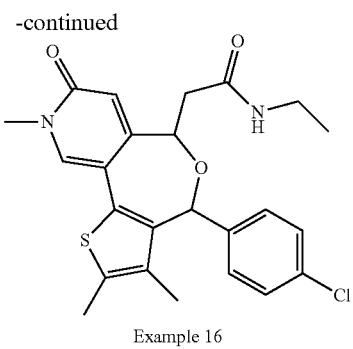

Example 16

Preparation of (E)-ethyl 3-(5-(3-(4-chlorobenzoyl)-4,5-dimethylthiophen-2-yl)-2-methoxypyridin-4-yl)acrylate (31)

A mixture of (2-bromo-4,5-dimethylthiophen-3-yl)(4-chlorophenyl)methanone (Intermediate L2, 0.35 g, 1.5 mmol), (E)-ethyl 3-(2-methoxy-5-(4,4,5,5-tetramethyl-1,3,2-dioxaborolan-2-yl)pyridin-4-yl)acrylate (Intermediate L1 0.425 g, 1.30 mmol) and 2M sodium bicarbonate (0.178 g, 2.12 mmol) were mixed in toluene (20 mL). The mixture was purged with nitrogen gas for 10 minutes. Then added tetrakis(triphenylphosphine)palladium(0) (0.12 g, 0.0106 mmol) to the mixture and again nitrogen gas was purged through the mixture for 5 minutes. The mixture was heated at 105° C. at 15 h. The reaction mixture was cooled to room temperature, diluted with water (100 mL) and extracted with ethyl acetate (100 mL). Organic layers were combined, washed with brine, dried over anhydrous sodium sulphate and concentrated to give a crude product. The crude product was purified by combi-flash (silica gel) eluting with 0-10% methanol in dichloromethane. The pure fractions were concentrated to obtain to afford the compound as a pale pink colored liquid (0.388 g, 80%). MS (ESI): mass calcd. For $C_{24}H_{22}ClNO_4S$, 455.11; m/z, found: 456.0 $[M+H]^+$.

Preparation of (E)-ethyl 3-(5-(3-((4-chlorophenyl)(hydroxy)methyl)-4,5-dimethylthiophen-2-yl)-2-methoxypyridin-4-yl)acrylate (32)

A solution of (E)-ethyl 3-(5-(3-(4-chlorobenzoyl)-4,5-dimethylthiophen-2-yl)-2 methoxypyridin-4-yl)acrylate (31, 0.34 g, 0.75 mmol) in methanol (20 mL), cerium(III) chloride heptahydrate (0.418 g, 1.12 mmol), was added and stirred at room temperature for 5 minutes and then sodium borohydride (0.041 g, 1.12 mmol) was added at 0° C. After 1 h the reaction mixture was diluted with water and ethyl acetate, the organic layer was separated and dried over sodium sulphate, and concentrated to obtain (E)-ethyl 3-(5-(3-((4-chlorophenyl)(hydroxy)methyl)-4,5-dimethylthiophen-2-yl)-2-methoxypyridin-4-yl)acrylate (0.27 g, 80%) as a pale yellow thick liquid. MS (ESI): mass calcd. for $C_{24}H_{24}ClNO_4S$, 457.11; m/z, found: 458.0 $[M+H]^+$.

Preparation of ±Ethyl 2-(4-(4-chlorophenyl)-8-methoxy-2,3-dimethyl-4,6-dihydrothieno[2',3':5,6]oxepino[4,3-c]pyridin-6-yl)acetate (33)

A solution of (E)-ethyl 3-(5-(3-((4-chlorophenyl)(hydroxy)methyl)-4,5-dimethylthiophen-2-yl)-2-methoxypyridin-4-yl)acrylate (32, 0.26 g, 0.57 mmol) and 1,8-diazabicycloundec-7-ene (0.432 g, 2.84 mmol) in THF (5 mL) was stirred at 25° C. After 24 h the reaction mixture was concentrated. The residue was purified by combi-flash eluting with 0-10% methanol in dichloromethane. The pure fractions were concentrated to obtain to afford ethyl 2-(4-(4-chlorophenyl)-8-methoxy-2,3-dimethyl-4,6-dihydrothieno[2',3':5,6]oxepino[4,3-c]pyridin-6-yl)acetate (0.21 g, 80%) as a pale pink colored liquid. $^1$HNMR: (400 MHz, DMSO-$d_6$) δ (ppm): 8.429 (s, 1H), 7.42 (d, J=8.4 Hz, 2H), 7.06 (d, J=8.4, 2H), 6.66 (s, 1H), 6.06 (s, 1H), 5.02-4.98 (m, 1H), 4.18 (q, J=8 Hz, 2H), 3.85 (s, 3H), 3.24-3.19 (m, 1H), 2.91-2.84 (m, 1H), 2.24-2.28 (m, 3H), 1.63 (s, 3H), 1.23 (t, J=8 Hz, 3H). MS (ESI): mass calcd. for $C_{24}H_{24}ClNO_4S$, 457.11; m/z, found: 458.1 $[M+H]^+$.

Example 15: ±ethyl 2-(4-(4-chlorophenyl)-2,3,9-trimethyl-8-oxo-4,6,8,9-tetrahydrothieno[2',3':5,6]oxepino[4,3-c]pyridin-6-yl)acetate To a solution of ethyl 2-(4-(4-chlorophenyl)-8-methoxy-2,3-dimethyl-4,6-dihydrothieno[2',3':5,6]oxepino[4,3-c]pyridin-6-yl)acetate (33, 0.2 g, 0.44 mmol), in acetonitrile (3 mL) to this methyl iodide (0.08 mL, 1.31 mmol) was added and heated to 80° C. in a sealed tube. After 15 h the mixture was cooled to room temperature and concentrated to get crude product. The crude product was purified by combi-flash (silica gel) eluting with 0-10% methanol in dichloromethane. The pure fractions were concentrated to obtain to afford ethyl 2-(4-(4-chlorophenyl)-2,3,9-trimethyl-8-oxo-4,6,8,9-tetrahydrothieno[2',3':5,6]oxepino[4,3-c]pyridin-6-yl)acetate (0.18 g, 90%) as a crystalline solid. MS (ESI): mass calcd. for $C_{24}H_{24}ClNO_4S$, 457.11; m/z, found: 458.1 $[M+H]^+$. NMR missing (not taken).

Preparation of ±2-(4-(4-chlorophenyl)-2,3,9-trimethyl-8-oxo-4,6,8,9-tetrahydrothieno[2',3':5,6]oxepino[4,3-c]pyridin-6-yl)acetic acid (34)

Ethyl 2-(4-(4-chlorophenyl)-2,3,9-trimethyl-8-oxo-4,6,8,9-tetrahydrothieno[2',3':5,6]oxepino[4,3-c]pyridin-6-yl)acetate (Example 15, 0.18 g, 0.42 mmol) was dissolved in methanol (5 mL), 4N sodium hydroxide (0.08 g, 2.02 mmol) was added and stirred at room temperature. After h the volatile was removed and the residue was dissolved in water and acidified with 2N hydrochloric acid. The precipitate was collected by filtration and dried to obtain 2-(4-(4-chlorophenyl)-2,3,9-trimethyl-8-oxo-4,6,8,9-tetrahydrothieno[2',3':5,6]oxepino[4,3-c]pyridin-6-yl)acetic acid (0.15 g, 89%) as a pale yellow color solid. MS (ESI): mass calcd. for $C_{22}H_{20}ClNO_4S$, 429.08; m/z, found: 430.0 $[M+H]^+$.

Example 16: +2-(4-(4-chlorophenyl)-2,3,9-trimethyl-8-oxo-4,6,8,9-tetrahydrothieno[2',3':5,6]oxepino[4,3-c]pyridin-6-yl)-N-ethylacetamide A solution of 2-(4-(4-chlorophenyl)-2,3,9-trimethyl-8-oxo-4,6,8,9-tetrahydrothieno[2',3':5,6]oxepino[4,3-c]pyridin-6-yl)acetic acid (34, 0.145 g, 0.34 mmol) and HATU (0.194 g, 0.51 mmol) were taken in DMF (1 mL), stirred at 25° C. After 5 min ethylamine solution (0.344 mL, 0.68 mmol, 2N in THF) was added and stirred for 1 h at the same temperature. The reaction mixture was diluted with ethyl acetate and washed with water. The organic layer was dried over anhydrous sodium sulphate and concentrated to give the crude product. The crude product was purified by combi-flash eluting with 0-10% methanol in dichloromethane. The pure fractions were concentrated to afford 2-(4-(4-chlorophenyl)-2,3,9-trimethyl-8-oxo-4,6,8,9-tetrahydrothieno[2',3':5,6]oxepino[4,3-c]pyridin-6-yl)-N-ethylacetamide (0.11 g, 71%) as a pale yellow color solid, ¹HNMR: (400 MHz, DMSO) δ (ppm): 7.99 (t, J=4 Hz, 1H), 7.94 (s, 1H), 7.34 (d, J=8 Hz, 2H), 7.07 (d, J=8 Hz, 1H), 6.18 (s, 1H), 8.89 (s, 1H), 4.96-4.92 (m, 1H), 3.47 (s, 3H), 3.19-3.09 (m, 2H), 2.78-2.73 (m, 1H), 2.58-2.54 (m, 1H), 2.23 (s, 3H) 1.58 (s, 3H), 1.06 (t, J=8 Hz, 3H). MS (ESI): mass calcd. for $C_{24}H_{25}ClN_2O_3S$, 456.13; m/z, found: 457.1 [M+H].

Preparative Chiral HPLC Method for the Separation of Enantiomers cc and dd

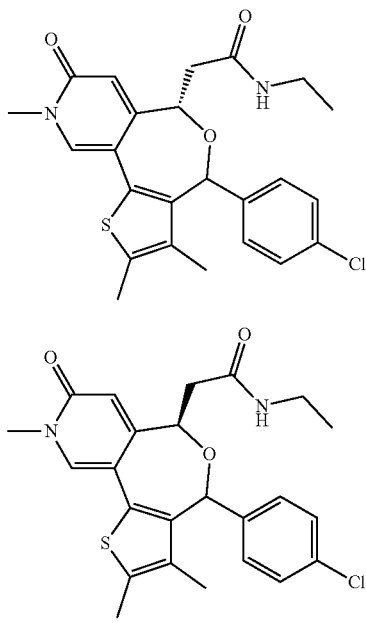

16a

16b

Preparative Chiral HPLC Method for the Separation of Enantiomers

Column: CHIRALPAK IA (250 mm×4.6 mm×5ìm)
Wavelength monitored 295 nm
Mobile phase: n-Hexane:0.1% DEA in Ethanol (50:50)

Example 16a: 2-((4S,6S)-4-(4-chlorophenyl)-2,3,9-trimethyl-8-oxo-4,6,8,9 tetrahydrothieno[2',3':5,6] oxepino[4,3-c]pyridin-6-yl)-N-ethylacetamide 1HNMR: (400 MHz, DMSO) δ (ppm): 7.99 (t, J=4 Hz, 1H), 7.94 (s, 1H), 7.34 (d, J =8 Hz, 2H), 7.07 (d, J=8 Hz, 1H), 6.18 (s, 1H), 8.89 (s, 1H), 4.96-4.92 (m, 1H), 3.47 (s, 3H), 3.19-3.09 (m, 2H), 2.78-2.73 (m, 1H), 2.58-2.54 (m, 1H), 2.23 (s, 3H) 1.58 (s, 3H), 1.06 (t, J=8 Hz, 3H). MS (ESI): mass calcd. for $C_{24}H_{25}ClN_2O_3S$, 456.13; m/z, found: 457.1 [M+H].

Example 16b: 2-(4R, 6R) (4-(4-chlorophenyl)-2,3, 9-trimethyl-8-oxo-4,6,8,9-tetrahydrothieno[2',3':5,6] oxepino[4,3-c]pyridin-6-yl)-N-ethylacetamide ¹HNMR: (400 MHz, DMSO) δ (ppm): 7.99 (t, J=4 Hz, 1H), 7.94 (s, 1H), 7.34 (d, J =8 Hz, 2H), 7.07 (d, J=8 Hz, 1H), 6.18 (s, 1H), 8.89 (s, 1H), 4.96-4.92 (m, 1H), 3.47 (s, 3H), 3.19-3.09 (m, 2H), 2.78-2.73 (m, 1H), 2.58-2.54 (m, 1H), 2.23 (s, 3H) 1.58 (s, 3H), 1.06 (t, J=8 Hz, 3H). MS (ESI): mass calcd. for $C_{24}H_{25}ClN_2O_3S$, 456.13; m/z, found: 457.1 [M+H].

Example 17: ±2-(4-(4-chlorophenyl)-2,3,9-trimethyl-8-oxo-4,6,8,9-tetrahydrothieno[2',3': 5,6]oxepino[4,3-c]pyridin-6-yl)acetamide

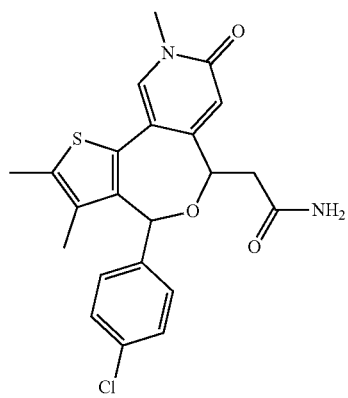 [SMILES: Cc1sc2c(c1C)C(c1ccc(Cl)cc1)OC(CC(N)=O)c1cc(=O)n(C)cc1-2]

HATU (0.26 g, 0.699 mmol) was added to a solution of 2-(4-(4-chlorophenyl)-2,3,9-trimethyl-8-oxo-4,6,8,9-tetrahydrothieno[2',3':5,6]oxepino[4,3-c]pyridin-6-yl)acetic acid (0.2 g, 0.466 mmol) in DMF (5 mL), stirred at 25° C. After 5 min liquor ammonia (7 mL) was added and stirred for 1 h at the same temperature. The reaction mixture was diluted with ethyl acetate and washed with water. The organic layer was dried over anhydrous sodium sulphate and concentrated to give the crude product. The crude product was purified by combi-flash eluting with 0-10% methanol in dichloromethane. The pure fractions were concentrated to afford 2-(4-(4-chlorophenyl)-2,3,9-trimethyl-8-oxo-4,6,8,9-tetrahydrothieno[2',3':5,6]oxepino[4,3-c]pyridin-6-yl)acetamide (0.280 g, 58%, yield) as a off-white solid. ¹HNMR: (400 MHz, DMSO) δ (ppm): 7.93 (s, 1H), 7.48 (s, 1H), 7.34 (d, J=8 Hz, 2H), 7.09 (d, J=8 Hz, 2H), 6.96 (s, 1H), 6.19 (s, 1H), 5.94 (s, 1H), 4.92 (t, J=8.0 Hz, 1H), 3.47 (s, 3H), 2.79-2.74 (m, 1H), 2.61-2.55 (m, 1H), 2.30 (s, 3H), 1.59 (s, 3H). MS (ESI): mass calcd for, $C_{22}H_{21}ClN_2O_3S$, 428.1 m/z found, 429.1 [M+1].

Preparative Chiral HPLC Method for the Separation of Enantiomers

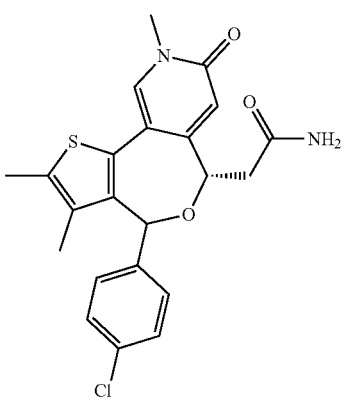

17a

-continued

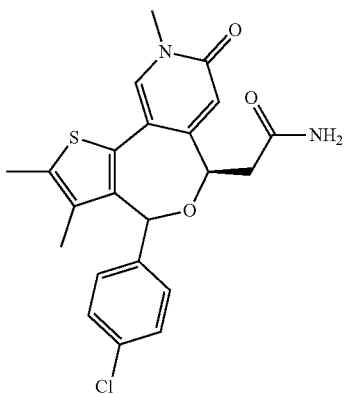

17b

Column: CHIRALPAK IA (250 mm×4.6 mm×5 μm)
UV: 265 nm
Mobile phase: n-Hexane: 0.1% DEA in IPA (70:30)

Example 17a: 2-((4S,6S)-4-(4-chlorophenyl)-2,3,9-trimethyl-8-oxo-4,6,8,9-tetrahydrothieno[2',3':5,6]oxepino[4,3-c]pyridin-6-yl)acetamide $^1$HNMR: (400 MHz, DMSO) δ (ppm): 7.93 (s, 1H), 7.48 (s, 1H), 7.34 (d, J=8 Hz, 2H), 7.09 (d, J=8 Hz, 2H), 6.96 (s, 1H), 6.19 (s, 1H), 5.94 (s, 1H), 4.92 (t, J=8.0 Hz, 1H), 3.47 (s, 3H), 2.79-2.74 (m, 1H), 2.61-2.55 (m, 1H), 2.30 (s, 3H), 1.59 (s, 3H). MS (ESI): mass calcd for, $C_{22}H_{21}ClN_2O_3S$, 428.1 m/z found, 429.1 [M+1].

Example 17b: 2-((4R,6R)-4-(4-chlorophenyl)-2,3,9-trimethyl-8-oxo-4,6,8,9-tetrahydrothieno[2',3':5,6]oxepino[4,3-c]pyridin-6-yl)acetamide $^1$HNMR: (400 MHz, DMSO) δ (ppm): 7.93 (s, 1H), 7.48 (s, 1H), 7.34 (d, J=8 Hz, 2H), 7.09 (d, J=8 Hz, 2H), 6.96 (s, 1H), 6.19 (s, 1H), 5.94 (s, 1H), 4.92 (t, J=8.0 Hz, 1H), 3.47 (s, 3H), 2.79-2.74 (m, 1H), 2.61-2.55 (m, 1H), 2.30 (s, 3H), 1.59 (s, 3H). MS (ESI): mass calcd for, $C_{22}H_{21}ClN_2O_3S$, 428.1 m/z found, 429.1 [M+1].

Example 18: ±4-(4-chlorophenyl)-6-(2-hydroxyethyl)-2,3,9-trimethyl-4,9-dihydrothieno[2',3':5,6]oxepino[4,3-c]pyridin-8(6H)-one

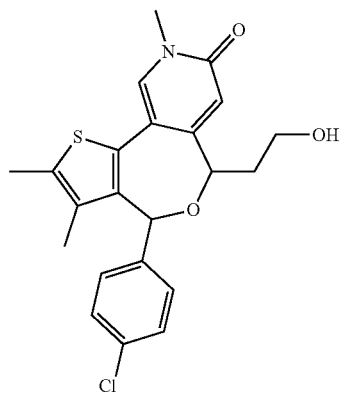

A solution of ethyl 2-(4-(4-chlorophenyl)-2,3,9-trimethyl-8-oxo-4,6,8,9-tetrahydrothieno[2',3':5,6]oxepino[4,3-c]pyridin-6-yl)acetate (15, 0.5 g, 0.11 mmol) in THF (5 mL) to this sodium borohydride (80 mg, 2.9 mmol) was added at rt and then the mixture was heated to 60° C. at this temperature methanol (3 mL) was added slowly. After 4 h the reaction mixture was cooled to room temperature and concentrated to get residue which was taken in ethyl acetate and washed with water. The organic layer was concentrated to obtain thick mass. The crude was purified by combi-flash eluting with 0-10% MeOH/DCM. The pure fractions were concentrated to afford 4-(4-chlorophenyl)-6-(2-hydroxyethyl)-2,3,9-trimethyl-4,9-dihydrothieno[2',3':5,6]oxepino[4,3-c]pyridin-8(6H)-one (0.2 g, 46%, yield) white color solid. $^1$HNMR: (400 MHz, DMSO) δ (ppm): 7.92 (s, 1H), 7.35 (d, J=8.0 Hz, 2H), 7.16 (d, J=8.0 Hz, 2H), 6.22 (s, 1H), 5.95 (s, 1H), 4.67-4.62 (m, 2H), 3.72-3.64 (m, 2H), 3.47 (s, 3H), 2.22 (s, 3H), 2.02-1.98 (m, 1H), 1.77-1.71 (m, 1H), 1.59 (s, 3H). MS (ESI): mass calcd for $C_{22}H_{22}ClNO_3S$, 415.10; m/z found, 416.1 [M+1].

Preparative Chiral HPLC Method for the Separation of Enantiomers Example 17

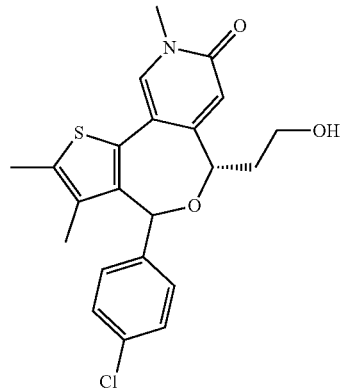 [SMILES: Cc1sc2c(c1C)C(c1ccc(Cl)cc1)OC(CCO)c1cc(=O)n(C)cc1-2]

18a

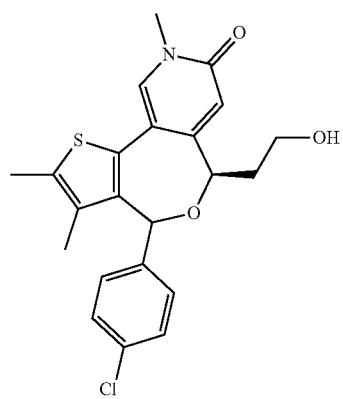

18b

Column: CHIRALPAK IA (250 mm×4.6 mm×5 μm)
UV: 265 nm
Mobile phase A: MTBE
Mobile phase B: Ethanol with 0.1% DEA Example 18a: (4S,6S)-4-(4-chlorophenyl)-6-(2-hydroxyethyl)-2,3,9-trimethyl-4,9-dihydrothieno[2',3':5,6]oxepino[4,3-c]pyridin-8(6H)-one $^1$HNMR: (400 MHz, DMSO) δ (ppm): 7.92 (s, 1H), 7.35 (d, J=8.0 Hz, 2H), 7.16 (d, J=8.0 Hz, 2H), 6.22 (s, 1H), 5.95

(s, 1H), 4.67-4.62 (m, 2H), 3.72-3.64 (m, 2H), 3.47 (s, 3H), 2.22 (s, 3H), 2.02-1.98 (m, 1H), 1.77-1.71 (m, 1H), 1.59 (s, 3H). MS (ESI): mass calcd for $C_{22}H_{22}ClNO_3S$, 415.10; m/z found, 416.1 [M+1].

Example 18b: (4R,6R)-4-(4-chlorophenyl)-6-(2-hydroxyethyl)-2,3,9-trimethyl-4,9-dihydrothieno[2',3':5,6]oxepino[4,3-c]pyridin-8(6H)-one $^1$HNMR: (400 MHz, DMSO) δ (ppm): 7.92 (s, 1H), 7.35 (d, J=8.0 Hz, 2H), 7.16 (d, J=8.0 Hz, 2H), 6.22 (s, 1H), 5.95 (s, 1H), 4.67-4.62 (m, 2H), 3.72-3.64 (m, 2H), 3.47 (s, 3H), 2.22 (s, 3H), 2.02-1.98 (m, 1H), 1.77-1.71 (m, 1H), 1.59 (s, 3H). MS (ESI): mass calcd for $C_{22}H_{22}ClNO_3S$, 415.10; m/z found, 416.1 [M+1].

Example 19: ±ethyl 2-(4-(4-chlorophenyl)-3,9-dimethyl-8-oxo-3,6,8,9-tetrahydropyrazolo[3,4-c]pyrido[3,4-e]azepin-6-yl)acetate

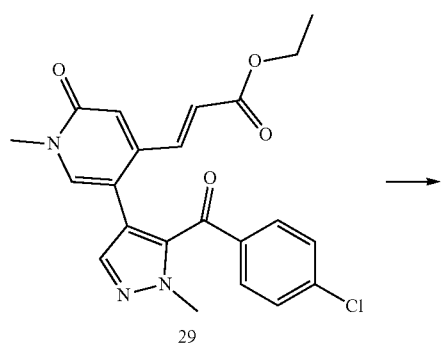

29

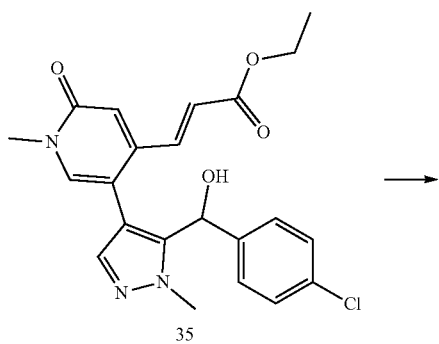

35

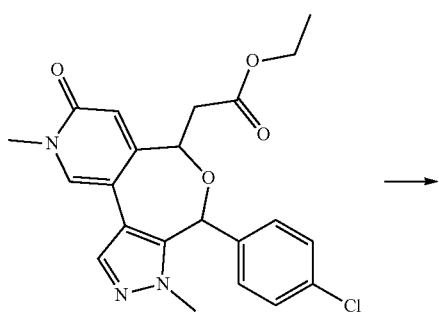

Example 19

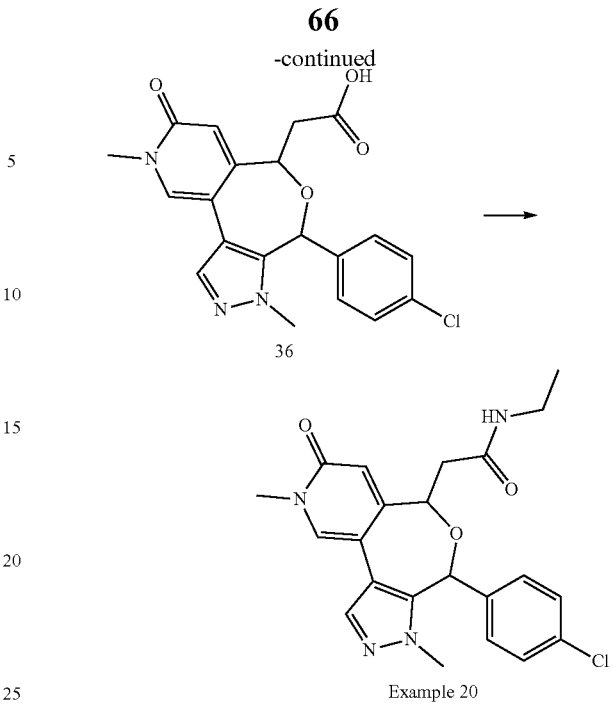

36

Example 20

To a stirred solution of ethyl (E)-3-(5-(5-(4-chlorobenzoyl)-1-methyl-1H-pyrazol-4-yl)-1-methyl-2-oxo-1,2-dihydropyridin-4-yl)acrylate (29, 1.00 g, 0.002 mol) in MeOH (20 mL) was added $CeCl_3.7H_2O$ (1.3 g, 0.0035 mol). Then reaction mixture was cooled down to temperature at ≤−10° C. Then $NaBH_4$ (0.284 g, 0.0075 mol) was added portion wise and reaction mixture was left for stirring 20 min. After completion of reaction, confirmed from TLC, reaction mixture was concentrated and extracted with ethyl acetate. The organic layer was washed with brine, dried over anhydrous sodium sulphate and concentrated. The compound was purified using combiflash (neutral alumina, eluent MeOH/DCM). The column fractions containing required product were collected and evaporated to get ethyl (E)-3-(5-(5-((4-chlorophenyl)(hydroxy)methyl)-1-methyl-1H-pyrazol-4-yl)-1-methyl-2-oxo-1,2-dihydropyridin-4-yl)acrylate (1.00 g, 99% yield). MS (ESI): mass calcd. For $C_{22}H_{22}ClN_3O_4$, 427.13; m/z, found: 428.1[M+H]$^+$.

Example 19: Ethyl 2-(4-(4-chlorophenyl)-3,9-dimethyl-8-oxo-4,6,8,9-tetrahydro-3H-pyrazolo[4',3':5,6]oxepino[4,3-c]pyridin-6-yl) acetate To a stirred solution of ethyl (E)-3-(5-(5-((4-chlorophenyl)(hydroxy)methyl)-1-methyl-1H-pyrazol-4-yl)-1-methyl-2-oxo-1,2-dihydropyridin-4-yl)acrylate (35, 1.00 g, 0.002 mol) in EtOH (20 mL) was added $K_2CO_3$ (1.6 g, 0.011 mol). After 5 min of stirring DBU (1 mL, 0.0070 mol) was added. Then reaction mixture was stirred for overnight at room temperature. The reaction mixture was concentrated and extracted with ethyl acetate and the organic layer was washed with brine, dried over anhydrous sodium sulphate and concentrated. The compound was purified using combiflash (silica gel, eluent MeOH/DCM). The column fractions containing required product were collected and evaporated to get ethyl2-(4-(4-chlorophenyl)-3,9-dimethyl-8-oxo-4,6,8,9-tetrahydro-3H-pyrazolo[4',3':5,6]oxepino[4,3-c]pyridin-6-yl)acetate purity. (0.3 g; 30% yield). MS (ESI): mass calcd. For $C_{22}H_{22}ClN_3O_4$, 427.13; m/z, found: 428.3 [M+H]$^+$.

Preparation of 2-(4-(4-chlorophenyl)-3,9-dimethyl-8-oxo-4,6,8,9-tetrahydro-3H-pyrazolo[4',3':5,6]oxepino[4,3-c]pyridin-6-yl)acetic acid. (36)

To a stirred solution of ethyl2-(4-(4-chlorophenyl)-3,9-dimethyl-8-oxo-4,6,8,9-tetrahydro-3H-pyrazolo[4',3':5,6] oxepino[4,3-c]pyridin-6-yl)acetate (0.3 g, 0.007 mol) in MeOH (10 mL) was added 4N NaOH solution and stirred for 2 h at room temperature. After completion of reaction, confirmed by TLC, MeOH was evaporated, residue was dissolved in ethyl acetate and extracted with water. The aqueous layer was acidified with 2N hydrochloric acid to pH 3. The precipitate was collected by filtration and dried to obtain 2-(4-(4-chlorophenyl)-3,9-dimethyl-8-oxo-4,6,8,9-tetrahydro-3H-pyrazolo[4',3': 5,6]oxepino[4,3-c]pyridin-6-yl)acetic acid with 90.43% purity. (0.28 g; 99% yield). MS (ESI): mass calcd. For $C_{20}H_{18}ClN_3O_4$ 399.10; m/z, found: 400.1[M+H]$^+$.

Example 20: 2-(4-(4-chlorophenyl)-3,9-dimethyl-8-oxo-4,6,8,9-tetrahydro-3H-pyrazolo[4',3':5,6]oxepino[4,3-c]pyridin-6-yl)-N-ethylacetamide To a stirred solution of 2-(4-(4-chlorophenyl)-3,9-dimethyl-8-oxo-4,6,8,9-tetrahydro-3H-pyrazolo[4',3':5,6]oxepino[4,3-c]pyridin-6-yl)acetic acid (0.1 g, 0.00025 mol) in DMF (10 mL) was added HATU (0.145 g, 0.00037 mol). After 5 min of stirring ethylamine (0.57 g, 0.00125 mol) was added followed by DIPEA (0.08 mL, 0.0005 mol) and reaction mixture was left for stirring 30 min. After completion of reaction, confirmed by TLC, crushed ice was added into reaction mixture and extracted with ethylacetate. The organic layer was washed with brine, dried over anhydrous sodium sulphate and concentrated. The crude compound was purified by prep RP-HPLC to get the title compound (0.010 g; 9.3% yield). $^1$HNMR: (400 MHz, DMSO) δ (ppm): 8.09 (s, 1H), 7.99 (m, 1H), 7.74 (s, 1H), 7.39 (d, J=8 Hz, 2H), 7.11 (d, J=8.4 Hz, 2H), 6.18 (s, 1H), 6.09 (s, 1H), 4.93-4.89 (m, 1H), 3.46 (s, 3H), 3.08-3.22 (m, 2H), 2.55-2.62 (m, 2H), 1.03 (t, J=7.2 Hz, 3H). MS (ESI): mass calcd. For $C_{22}H_{23}ClN_4O_3$, 426.15; m/z, found: 427.1 [M+H]$^+$.

BIOLOGICAL METHODS

Biological Methods
BRD4 AlphaLISA (Perkin Elmer)
Compounds were diluted by step-down dilution method (final concentration of DMSO was 1%) and added to the wells of a 384 well opti plate at desired concentrations. 5 nM BDR4-BD1 enzyme (produced in-house) and 12 nM of biotinylated substrate were added to the wells, covered and incubated at room temperature (RT) for 1 h. At the end of 1 h 250 ng of GSH acceptor beads were added to the well and incubated for 1 h at RT; then 500 ng of streptavidin donor beads were added and incubated again for 1 h at RT. Plates were read in a Pherastar reader at 680 nm excitation and 570 nm emission. As detailed above, compounds were tested for both BRD4 enzyme inhibitory activities and IC$_{50}$ were determined. The activities of selected compounds are listed in Table 1
Anticancer Activity: Alamar Blue Assay
The impact of the compounds on cancer cell proliferation was determined using the AML cell line MV4-11 (ATCC) in a 3-day proliferation assay. MV4-11 cells were maintained in RPMI supplemented with 10% FBS at 37° C., 5% CO$_2$. For compound testing, MV4-11 cells were plated in a 96-well black bottom plate at a density of 15,000 cells/well in 100 μL culture media and incubated at 37° C. overnight. Compound dilution series were prepared in DMSO via a 3-fold serial dilution from 100 μM to 0.005 μM. The DMSO dilution series were then diluted with media, with the final compound concentrations added to the wells ranging from 10 μM to 0.0005 μM. After the additions of compounds, the cells were incubated for 72 h and the numbers of viable cells were determined using the Alamar Blue assay (Invitrogen), according the manufacturer suggested protocol. The fluorescent readings from the Alamar Blue assay were normalized to the DMSO treated cells and analyzed using the GraphPad Prism software with sigmoidal curve fitting to obtain EC$_{50}$. The selected compounds activities are listed in Table 1.

TABLE 1

Selected list of compounds with BRD4-BD1 IC$_{50}$ and Anti-cancer activity

| Compound | BRD4_BD1 IC50_μM | MV4-11 EC50_μM |
|---|---|---|
| b | 0.0022 | 0.01 |
| e | 0.002 | 0.007 |
| h | 0.033 | ND |
| k | <0.0005 | 0.025 |
| l | 0.14 | 0.43 |
| m | 0.001 | 0.14 |
| r | 0.01 | 0.157 |
| t | 0.002 | 0.017 |
| w | 0.01 | 0.026 |
| z | 0.005 | 0.053 |
| bb | 0.001 | <0.0005 |
| ee | 0.002 | 0.007 |
| hh | 0.017 | ND |
| ll | 0.001 | <0.0005 |

Determination of Biomarker C-Myc and p21 in MV4-11 Cells.

MV4-11 cells were seeded in a 24-well plate at a density of 0.2×10$^6$ cells/ml and incubated at 37° C. overnight. The cells were treated with the compounds at the indicated concentrations and time points. The cells were harvested at the indicated time points and protein extraction was performed using the RIPA buffer. For the tumor samples, the protein was extracted by homogenizing a small piece of the tumor in RIPA buffer. 25-50 μg protein was resolved in SDS-PAGE and subjected to Western Blotting. The antibodies against cMYC and p21 were purchased from Cell Signaling. The antibody against P3-Actin was purchased from Sigma.
In Vivo Xenograft Model
The effects of the compounds to inhibit the growth of MV4-11 xenograft tumors were evaluated. Briefly, 5×10$^6$ cells of MV4-11 cells; diluted 1:1 with matrigel were injected subcutaneously on the upper flanks of female nude mice (Charles Rivers Labs). The total volume injected per animal was 200 μL. The mice were observed for approximately 15-20 days with concomitant tumor volume measurement. The treatment was initiated post-randomization when the average tumor volume was approximately 100 mm$^3$. The compounds were formulated in 0.02% tween-80, 0.5% methylcellulose and administered by oral gavage. The tumors were measured by a pair of calipers thrice a week starting at the time of size match, and tumor volumes were calculated according to the formula V=(L×W×H)×0.52 (V: volume, mm$^3$; L: length, mm; W: width, mm; H: height, mm). The tumor volume and body weight were measured for the duration of the experiment, until the mean tumor volume in each group reached an endpoint of >1000 mm³. Compounds of formula I showing greater 50% tumor growth inhibition are considered as active.

Although the subject matter has been described in considerable detail with reference to certain embodiments thereof, other embodiments are possible. As such, the spirit and scope of the invention should not be limited to the description of the embodiments contained herein.

We claim:

1. A compound of the Formula (I)

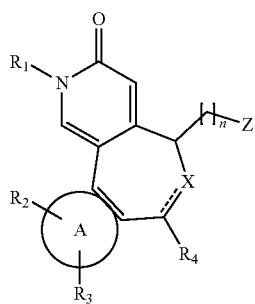

Formula (I)

wherein;
---- is absent or a single bond;
X is —O—;
n is 0-6;
$R_1$ is selected from the group consisting of hydrogen, halogen, $C_{1-6}$ alkyl, $C_{1-6}$ alkoxy, $C_{1-6}$ haloalkyl, $C_{3-8}$ cycloalkyl, $C_{5-6}$ aryl, $C_{1-6}$ heteroaryl with heteroatoms selected from N, O, and S, and $C_{1-6}$ alkoxyalkyl;
  wherein $C_{1-6}$ alkyl, $C_{3-8}$ cycloalkyl, $C_{5-6}$ aryl, or $C_{1-6}$ heteroaryl is optionally substituted with one or more of the groups selected from hydrogen, $C_{1-6}$ alkyl, halogen, and OH;
$R_2$ and $R_3$ are independently selected from hydrogen, halogen, hydroxy, nitro, cyano, azido, nitroso, oxo (=O), thioxo (=S), amino, hydrazino, formyl, $C_{1-6}$ alkyl, haloalkyl, $C_{1-6}$ alkoxy, $C_{1-6}$ haloalkoxy, arylalkoxy, $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$, —$NR_aC(S)R_b$, —$SONR_aR_b$, —$SO_2NR_aR_b$, —$OR_a$, —$OC(O)NR_aR_b$, —$OC(O)R_a$, —$SR_a$, —$SOR_a$, and —$SO_2R_a$, wherein $R_a$, $R_b$ and $R_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl, and $C_{2-6}$ heteroarylalkyl;
$R_4$ is selected from the group consisting of hydrogen, $C_{1-6}$ alkyl, $C_{1-6}$ haloalkyl, $C_{3-8}$ cycloalkyl, $C_{5-6}$ aryl, $C_{1-6}$ heteroaryl with heteroatoms selected from N, O, and S, and $C_{1-6}$ alkoxyalkyl;
  wherein $C_{1-6}$ alkyl, $C_{3-8}$ cycloalkyl, $C_{5-6}$ aryl, or $C_{2-6}$ heteroaryl is optionally substituted with one or more of the groups selected from hydrogen, $C_{1-6}$ alkyl, $C_{3-8}$ cycloalkyl, halogen, OH, and cyano;
  ring A is selected from the group consisting of $C_{1-6}$ heteroaryl, $C_{3-8}$ cycloalkyl, $C_{4-6}$ heterocycloalkyl, and $C_{4-10}$ heterocycloaryl with heteroatoms selected from N, O, and S;

Z is selected from —$CH_2OR_5$, —$COOR_5$, —$CONR_5R_6$, —$NR_5R_6$, —$NR_5CO$—$OR_6$, —$NR_5CO$—$NR_6R_7$, —$NR_5COR_6$, —$NR_5SO_2R_6$, and —O—CO—$NR_5R_6$;
$R_5$, $R_6$, and $R_7$ are independently selected from hydrogen, substituted or unsubstituted $C_{5-6}$ aryl, $C_{1-6}$ heteroaryl, $C_{3-8}$ cycloalkyl, and $C_{1-6}$ alkyl;
  wherein when $R_5$, $R_6$, and $R_7$ are substituted, the one or more substituents are selected from hydrogen, halogen, hydroxy, nitro, cyano, azido, nitroso, thioxo (=S), amino, hydrazino, formyl, $C_{1-6}$ alkyl, haloalkyl, $C_{1-6}$ alkoxy, $C_{1-6}$ haloalkoxy, $C_{5-6}$ arylalkoxy, $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, —$NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$, $NR_aC(S)R_b$, $SONR_aR_b$, —$SO_2NR_aR_b$, —$OR_a$, —$OC(O)NR_aR_b$, —$OC(O)R_a$, —$SR_a$, —$SOR_a$, and —$SO_2R_a$, wherein $R_a$, $R_b$ and $R_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl, and $C_{1-6}$ heteroarylalkyl.

2. A compound of the Formula (I)

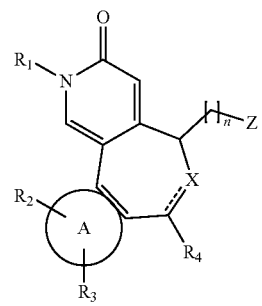

Formula (I)

wherein;
---- is absent or a single bond;
X is —O—;
n is 0-6;
$R_1$ is selected from the group consisting of hydrogen, halogen, $C_{1-6}$ alkyl, $C_{1-6}$ alkoxy, $C_{1-6}$ haloalkyl, $C_{3-8}$ cycloalkyl, $C_{5-6}$ aryl, $C_{1-6}$ heteroaryl with heteroatoms selected from N, O, and S, and alkoxyalkyl;
  wherein $C_{1-6}$ alkyl, $C_{3-8}$ cycloalkyl, $C_{5-6}$ aryl, or $C_{1-6}$ heteroaryl is optionally substituted with one or more of the groups selected from hydrogen, $C_{1-6}$ alkyl, halogen, and OH;
$R_2$ and $R_3$ are independently selected from hydrogen, halogen, hydroxy, nitro, cyano, azido, nitroso, oxo (=O), thioxo (=S), amino, hydrazino, formyl, $C_{1-6}$ alkyl, $C_{1-6}$ haloalkyl, $C_{1-6}$ alkoxy, $C_{1-6}$ haloalkoxy, arylalkoxy, $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, $NR_aC(O)OR_b$, —$NR_aR_b$, —$NR_aC(O)R_b$, —$NR_aC(S)R_b$, —$SONR_aR_b$, —$SO_2NR_aR_b$, —$OR_a$, —$OC(O)NR_aR_b$, —$OC(O)R_a$, —$SR_a$, —$SOR_a$, and —$SO_2R_a$, wherein $R_a$, $R_b$ and $R_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl, and $C_{1-6}$ heteroarylalkyl;

$R_4$ is selected from the group consisting of $C_{1-6}$ alkyl, haloalkyl, $C_{3-8}$ cycloalkyl, $C_{5-6}$ aryl, $C_{1-6}$ heteroaryl with heteroatoms selected from N, O, and S, and alkoxyalkyl;

wherein $C_{1-6}$ alkyl, $C_{3-8}$ cycloalkyl, $C_{5-6}$ aryl, or $C_{1-6}$ heteroaryl is optionally substituted with one or more of the groups selected from hydrogen, $C_{1-6}$ alkyl, halogen, OH, and cyano;

ring A is selected from thienyl, thiazolyl, pyridinyl, pyrimidinyl, pyrrolyl, pyrazinyl, pyridazinyl, pyrazolyl, oxazolyl, triazolyl, imidazolyl, isoxazolyl, isothiazolyl, thiadiazolyl, and furyl;

Z is selected from —$CH_2OR_5$, —$COOR_5$, —$CONR_5R_6$, —$NR_5R_6$, —$NR_5CO$—$OR_6$, —$NR_5CO$—$NR_6R_7$, —$NR_5COR_6$, —$NR_5SO_2R_6$, and —O—CO—$NR_5R_6$;

$R_5$, $R_6$, and $R_7$ are independently selected from hydrogen, substituted or unsubstituted $C_{5-6}$ aryl, $C_{1-6}$ heteroaryl, $C_{3-8}$ cycloalkyl, and $C_{1-6}$ alkyl;

wherein when $R_5$, $R_6$, and $R_7$ are substituted, the one or more substituents are selected from hydrogen, halogen, hydroxy, nitro, cyano, azido, nitroso, oxo (=O), thioxo (=S), amino, hydrazino, formyl, $C_{1-6}$ alkyl, haloalkyl, $C_{1-6}$ alkoxy, $C_{1-6}$ haloalkoxy, $C_{5-6}$ arylalkoxy, $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$, —$NR_aC(S)R_b$, —$SONR_aR_b$, —$SO_2NR_aR_b$, —$OR_a$, —$OC(O)NR_aR_b$, —$OC(O)R_a$, —$SR_a$, —$SOR_a$, and —$SO_2R_a$, wherein $R_a$, $R_b$ and $R_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl, and $C_{1-6}$ heteroarylalkyl.

3. A compound of the Formula (I)

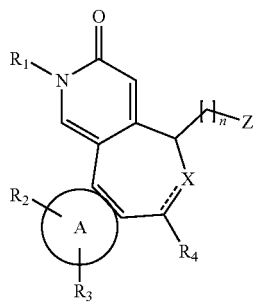

Formula (I)

wherein
---- is absent;
X is —O—;
n is 0-6;
$R_1$ is $C_{1-6}$ alkyl, wherein $C_{1-6}$ alkyl is optionally substituted with one or more of the groups selected from hydrogen, $C_{1-6}$ alkyl, halogen, and OH;
$R_2$ and $R_3$ are independently selected from hydrogen, halogen, hydroxy, $C_{1-6}$ alkyl, $C_{1-6}$ haloalkyl, $C_{1-6}$ alkoxy, and $C_{1-6}$ haloalkoxy;
$R_4$ is selected from the group consisting of $C_{1-6}$ alkyl, haloalkyl, $C_{3-8}$ cycloalkyl, $C_{5-6}$ aryl, $C_{1-6}$ heteroaryl with heteroatoms selected from N, O, and S, and alkoxyalkyl;

wherein $C_{1-6}$ alkyl, $C_{3-8}$ cycloalkyl, $C_{5-6}$ aryl, or $C_{1-6}$ heteroaryl is optionally substituted with one or more of the groups selected from hydrogen, $C_{1-6}$ alkyl, halogen, OH and cyano;

ring A is selected from thienyl, thiazolyl, pyridinyl, pyrimidinyl, pyrrolyl, pyrazinyl, pyridazinyl, pyrazolyl, oxazolyl, triazolyl, imidazolyl, isoxazolyl, isothiazolyl, thiadiazolyl, and furyl;

Z is selected from —$CH_2OR_5$, —$COOR_5$, —$CONR_5R_6$, —$NR_5R_6$, —$NR_5CO$—$OR_6$, —$NR_5CO$—$NR_6R_7$, —$NR_5COR_6$, —$NR_5SO_2R_6$, and —O—CO—$NR_5R_6$;

$R_5$, $R_6$, and $R_7$ are independently selected from hydrogen, substituted or unsubstituted $C_{5-6}$ aryl, $C_{1-6}$ heteroaryl, $C_{3-8}$ cycloalkyl, and $C_{1-6}$ alkyl;

wherein when $R_5$, $R_6$, and $R_7$ are substituted, the one or more substituents are selected from hydrogen, halogen, hydroxy, nitro, cyano, azido, nitroso, oxo (=O), thioxo (=S), amino, hydrazino, formyl, $C_{1-6}$ alkyl, haloalkyl, $C_{1-6}$ alkoxy, $C_{1-6}$ haloalkoxy, $C_{5-6}$ arylalkoxy, $C_{3-8}$ cycloalkyl, $C_{3-8}$ cycloalkyloxy, $C_{5-6}$ aryl, $C_{2-6}$ heterocyclyl, $C_{1-6}$ heteroaryl, alkylamino, —$COOR_a$, —$C(O)R_b$, —$C(S)R_a$, —$C(O)NR_aR_b$, —$C(S)NR_aR_b$, —$NR_aC(O)NR_bR_c$, $NR_aC(S)NR_bR_c$, —$N(R_a)SOR_b$, —$N(R_a)SO_2R_b$, —$NR_aC(O)OR_b$, —$NR_aR_b$, —$NR_aC(O)R_b$, —$NR_aC(S)R_b$, —$SONR_aR_b$, —$SO_2NR_aR_b$, —$OR_a$, —$OC(O)NR_aR_b$, —$OC(O)R_a$, —$SR_a$, —$SOR_a$, and —$SO_2R_a$, wherein $R_a$, $R_b$ and $R_c$ are independently selected from hydrogen, $C_{1-6}$ alkyl, $C_{3-8}$ cycloalkyl, $C_{5-6}$ aryl, $C_{5-6}$ arylalkyl, $C_{2-6}$ heterocyclyl, $C_{1-6}$ heteroaryl, and $C_{1-6}$ heteroarylalkyl.

4. A compound of the Formula (I)

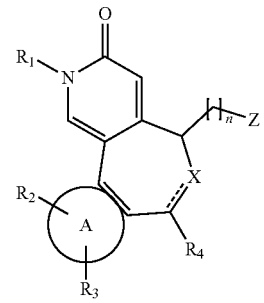

Formula (I)

wherein;
---- is absent;
X is —O—;
n is 1-2;
$R_1$ is $C_{1-4}$ alkyl;
$R_2$ and $R_3$ are independently selected from hydrogen, $C_{1-4}$ alkyl, and $C_{1-4}$ alkoxy;
$R_4$ is selected from the group consisting of $C_{3-8}$ cycloalkyl and $C_{5-6}$ aryl,
wherein $C_{3-8}$ cycloalkyl or $C_{5-6}$ aryl is substituted with one or more of the groups selected from hydrogen, $C_{1-6}$ alkyl, halogen, and cyano;
ring A is selected from thienyl, thiazolyl, pyridinyl, pyrimidinyl, pyrrolyl, pyrazinyl, pyridazinyl, pyrazolyl, oxazolyl, triazolyl, imidazolyl, isoxazolyl, isothiazolyl, thiadiazolyl, and furyl;
Z is selected from —$CH_2OR_5$, —$COOR_5$, —$CONR_5R_6$, —$NR_5R_6$, —$NR_5CO$—$OR_6$, —NR₅CO—NR₆R₇, —NR₅COR₆, —NR₅SO₂R₆, and —O—CO—NR₅R₆;

R₅, R₆, and R₇ are independently selected from hydrogen or substituted or unsubstituted C₅₋₆ aryl, C₁₋₆ heteroaryl, C₃₋₈ cycloalkyl, and C₁₋₆ alkyl;

wherein when R₅, R₆, and R₇ are substituted, the one or more substituents are selected from hydrogen, halogen, hydroxy, nitro, cyano, azido, nitroso, oxo (=O), thioxo (=S), amino, hydrazino, formyl, C₁₋₆ alkyl, haloalkyl, C₁₋₆ alkoxy, C₁₋₆ haloalkoxy, C₅₋₆ arylalkoxy, C₃₋₈ cycloalkyl, C₃₋₈ cycloalkyloxy, C₅₋₆ aryl, C₂₋₆ heterocyclyl, C₁₋₆ heteroaryl, alkylamino, —COORₐ, —C(O)Rᵦ, —C(S)Rₐ, —C(O)NRₐRᵦ, —C(S)NRₐRᵦ, —NRₐC(O)NRᵦRᶜ, NRₐC(S)NRᵦRᶜ, —N(Rₐ)SORᵦ, —N(Rₐ)SO₂Rᵦ, —NRₐC(O)ORᵦ, —NRₐRᵦ, —NRₐC(O)Rᵦ, —NRₐC(S)Rᵦ, —SONRₐRᵦ, —SO₂NRₐRᵦ, —ORₐ, —OC(O)NRₐRᵦ, —OC(O)Rₐ, —SRₐ, —SORₐ, and —SO₂Rₐ, wherein Rₐ, Rᵦ and Rᶜ are independently selected from hydrogen, C₁₋₆ alkyl, C₃₋₈ cycloalkyl, C₅₋₆ aryl, C₅₋₆ arylalkyl, C₂₋₆ heterocyclyl, C₁₋₆ heteroaryl, and C₁₋₆ heteroarylalkyl.

5. A compound of the Formula (I)

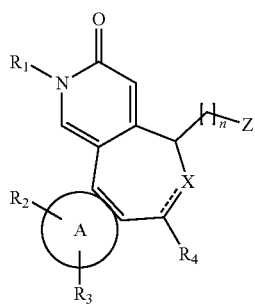

Formula (I)

wherein;

---- is absent;

X is —O—;

n is 1-2;

R₁ is C₁ alkyl;

R₂ and R₃ are independently selected from hydrogen, C₁₋₂ alkyl, and C₁₋₂ alkoxy;

R₄ is selected from the group consisting of C₃₋₈ cycloalkyl and C₅₋₆ aryl, wherein C₃₋₈ cycloalkyl or C₅₋₆ aryl is substituted with one or more of the groups selected from hydrogen, C₁₋₆ alkyl, halogen, and cyano;

ring A is selected from thienyl, thiazolyl, pyridinyl, pyrimidinyl, pyrrolyl, pyrazinyl, pyridazinyl, and pyrazolyl;

Z is selected from —CH₂OR₅, —COOR₅, —CONR₅R₆, and —NR₅R₆;

R₅ and R₆ are independently selected from hydrogen, substituted or unsubstituted C₅₋₆ aryl, and C₁₋₆ alkyl;

wherein when R₅ and R₆ are substituted, the substituents are selected from hydrogen, halogen, hydroxy, nitro, cyano and C₁₋₆ alkyl.

6. A compound of the Formula (I)

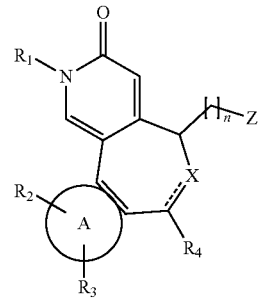

Formula (I)

wherein;

---- is absent or single bond;

X is —O—;

n is 1-2;

R₁ is C₁ alkyl;

R₂ and R₃ are independently selected from hydrogen and C₁₋₂ alkyl;

R₄ is selected from the group consisting of C₃₋₈ cycloalkyl and C₅₋₆ aryl, wherein C₃₋₈ cycloalkyl or C₅₋₆ aryl is substituted with one or more of the groups selected from hydrogen, C₁₋₆ alkyl, halogen, and cyano;

ring A is selected from thienyl, thiazolyl, pyridinyl, and pyrimidinyl;

Z is selected from —CH₂OR₅, —COOR₅, —CONR₅R₆, and —NR₅R₆;

R₅ and R₆ are independently selected from hydrogen, substituted or unsubstituted C₅₋₆ aryl, and C₁₋₆ alkyl;

wherein when R₅ and R₆ are substituted, the substituents are selected from hydrogen, halogen, hydroxy, nitro, cyano, and C₁₋₆ alkyl.

7. The compound as claimed in claim 1 having the Formula (I), which is selected from a group consisting of:

aa. ±Ethyl 2-(4-(4-chlorophenyl)-2,3,9-trimethyl-8-oxo-4,6,8,9-tetrahydrothieno[2',3':5,6]oxepino[4,3-c]pyridin-6-yl)acetate, bb. ±2-(4-(4-chlorophenyl)-2,3,9-trimethyl-8-oxo-4,6,8,9-tetrahydrothieno[2',3':5,6]oxepino[4,3-c]pyridin-6-yl)-N-ethylacetamide, cc. 2-(4S, 6S) (4-(4-chlorophenyl)-2,3,9-trimethyl-8-oxo-4,6,8,9-tetrahydrothieno[2',3':5,6]oxepino[4,3-c]pyridin-6-yl)-N-ethylacetamide, dd. 2-(4R, 6R) (4-(4-chlorophenyl)-2,3,9-trimethyl-8-oxo-4,6,8,9-tetrahydrothieno[2',3':5,6]oxepino[4,3-c]pyridin-6-yl)-N-ethylacetamide, ee. ±2-(4-(4-chlorophenyl)-2,3,9-trimethyl-8-oxo-4,6,8,9-tetrahydrothieno[2',3':5,6]oxepino[4,3-c]pyridin-6-yl)acetamide, ff. 2-((4S, 6S)-4-(4-chlorophenyl)-2,3,9-trimethyl-8-oxo-4,6,8,9-tetrahydrothieno[2',3':5,6]oxepino[4,3-c]pyridin-6-yl)acetamide, gg. 2-((4R, 6R)-4-(4-chlorophenyl)-2,3,9-trimethyl-8-oxo-4,6,8,9-tetrahydrothieno[2',3':5,6]oxepino[4,3-c]pyridin-6-yl)acetamide, hh. ±4-(4-chlorophenyl)-6-(2-hydroxyethyl)-2,3,9-trimethyl-4,9-dihydrothieno[2',3':5,6]oxepino[4,3-c]pyridin-8(6H)-one, ii. (4S,6S)-4-(4-chlorophenyl)-6-(2-hydroxyethyl)-2,3,9-trimethyl-4,9-dihydrothieno[2',3':5,6]oxepino[4,3-c]pyridin-8(6H)-one, jj. (4R,6R)-4-(4-chlorophenyl)-6-(2-hydroxyethyl)-2,3,9-trimethyl-4,9-dihydrothieno[2',3':5,6]oxepino[4,3-c]pyridin-8(6H)-one, kk. ±ethyl 2-(4-(4-chlorophenyl)-3,9-dimethyl-8-oxo-4,6,8,9-tetrahydro-3H-pyrazolo[4',3':5,6]oxepino[4,3-c]pyridin-6-yl)acetate, and ll. ±2-(4-(4-chlorophenyl)-3,9-dimethyl-8-oxo-4,6,8,9-tetrahydro-3H-pyrazolo[4',3':5,6]oxepino[4,3-c]pyridin-6-yl)-N-ethylacetamide.

8. A pharmaceutical composition comprising a compound of Formula (I) or a pharmaceutically acceptable salt thereof of as claimed in claim 1 together with a pharmaceutically acceptable carrier, optionally in combination with one or more other pharmaceutical compositions.

9. The pharmaceutical composition as claimed in claim 8, wherein the composition is in the form of a tablet, capsule, powder, syrup, solution, aerosol or suspension.

10. A method for the treatment of a cancer, comprising administering to a subject suffering from the cancer a therapeutically effective amount of the compound as claimed in claim 1 or the pharmaceutical composition as claimed in claim 8, wherein the cancer is lymphoma, myeloma, or leukemia.

\* \* \* \* \*